US012767987B2

(12) United States Patent
Su et al.

(10) Patent No.: US 12,767,987 B2
(45) Date of Patent: Oct. 20, 2026

(54) METHOD FOR SCREENING MULTIPLEX REVERSE TRANSCRIPTION PRIMER COMBINATIONS FOR QUANTIFYING MULTIPLE MIRNAS

(71) Applicant: MIRACLE BIOTECHNOLOGY INC., Houston, TX (US)

(72) Inventors: Chang Su, Clyde Hill, WA (US); Yuan Cao, Suzhou (CN); Mengjing Cao, Suzhou (CN); Demei Ma, Suzhou (CN)

(73) Assignee: MIRACLE BIOTECHNOLOGY INC., Houston, TX (US)

( * ) Notice: Subject to any disclaimer, the term of this patent is extended or adjusted under 35 U.S.C. 154(b) by 0 days.

(21) Appl. No.: 18/797,835

(22) Filed: Aug. 8, 2024

(65) Prior Publication Data

US 2024/0392377 A1 Nov. 28, 2024

Related U.S. Application Data

(63) Continuation of application No. PCT/US2023/067520, filed on May 26, 2023.

(30) Foreign Application Priority Data

May 6, 2023 (WO) ................ PCT/CN2023/092571

(51) Int. Cl.
*C12N 15/10* (2006.01)
*C12Q 1/6825* (2018.01)
(Continued)

(52) U.S. Cl.
CPC ....... *C12Q 1/6883* (2013.01); *C12N 15/1096* (2013.01); *C12Q 1/6825* (2013.01);
(Continued)

(58) Field of Classification Search
CPC .. C12Q 1/6883; C12Q 1/6851; C12Q 1/6825; C12N 15/1096
See application file for complete search history.

(56) References Cited

U.S. PATENT DOCUMENTS

2005/0266418 A1* 12/2005 Chen ........................ C12P 19/34
435/6.12
2014/0272993 A1 9/2014 Van Keuren-Jensen et al.
(Continued)

FOREIGN PATENT DOCUMENTS

CN 102108403 A 6/2011
CN 113005181 A 6/2021
(Continued)

OTHER PUBLICATIONS

Jet, T, Gines, G, Rondelez, Y, Taly, V. 2021 Advances in multiplexed techniques for the detection and quantification of microRNAs, Chem Soc Rev, 50, 4141-4161 (Year: 2021).*
(Continued)

*Primary Examiner* — Neil P Hammell
*Assistant Examiner* — Lisa Horth
(74) *Attorney, Agent, or Firm* — troutman pepper locke; Tim Tingkang Xia, Esq.

(57) ABSTRACT

A method for selecting and screening a multiplex reverse transcription primer combination for quantifying multiple target miRNAs simultaneously, and the application of the multiplex reverse transcription primer combination for determining a physiological or mental condition of a living subject.

17 Claims, 43 Drawing Sheets

Specification includes a Sequence Listing.

(51) Int. Cl.
*C12Q 1/6851* (2018.01)
*C12Q 1/6883* (2018.01)
*G01N 21/64* (2006.01)

(52) U.S. Cl.
CPC ....... *C12Q 1/6851* (2013.01); *G01N 21/6486* (2013.01); *C12Q 2600/178* (2013.01)

(56) References Cited

U.S. PATENT DOCUMENTS

| | | | |
|---|---|---|---|
| 2015/0292002 A1 | 10/2015 | Andersen et al. | |
| 2019/0017108 A1 | 1/2019 | Xu et al. | |
| 2022/0312707 A1* | 10/2022 | Skadhauge .......... | A01H 6/4624 |

FOREIGN PATENT DOCUMENTS

| | | | |
|---|---|---|---|
| EP | 2580355 | B1 | 3/2018 |
| EP | 4012047 | A1 | 6/2022 |
| KR | 20200127495 | A | 11/2020 |
| KR | 20230057233 | A | 4/2023 |
| WO | 2007117256 | A1 | 10/2007 |
| WO | 2017035090 | A1 | 3/2017 |
| WO | 2023023673 | A2 | 2/2023 |

OTHER PUBLICATIONS

Lao, K. et al., 2006, Multiplexing RT-PCR for the detection of multiple miRNA species in small samples, Biochemical and Biophysical Research Communications 343 85-89 (Year: 2006).*

Busk, P. 2014 A tool for design of primers for microRNA-specific quantitative RT-qPCR, BMC Bioinformatics 2014, 15:29 (Year: 2014).*

Suzuki, H., Mar. 2023, Roles of MicroRNAs in Disease Biology, Ma J. 2023;6(2): 104-113 (Year: 2023).*

Li, A. et al.(2007) Evolution of plant microRNA gene families Cell Research 17:212-218, (Year: 2007).*

Chen, C. et al. Real-time quantification of microRNAs by stem-loop RT-PCR, 2005, Nucleic Acids Research 33: 1-9 (Year: 2005).*

Mestdagh et al., High throughput stem-loop RT-qPCR miRNA expression profiling using minute amounts of input RNA, 2008, Nucleic Acids Research, 36: 1-8. (Year: 2008).*

Korean Intellectual Property Office (ISR/KR), "International Search Report for PCT/US2023/067520", Korea, Feb. 2, 2024.

Korean Intellectual Property Office (ISR/KR), "International Search Report for PCT/US2023/067522", Korea, Feb. 2, 2024.

Korean Intellectual Property Office (ISR/KR), "International Search Report for PCT/US2023/067524", Korea, Feb. 2, 2024.

Korean Intellectual Property Office (ISR/KR), "International Search Report for PCT/US2023/067528", Korea, Feb. 2, 2024.

Korean Intellectual Property Office (ISR/KR), "International Search Report for PCT/US2023/067531", Korea, Jan. 24, 2024.

He, F. et al., 'OUIIP: an optimized universal hairpin primer system for cost-effective and high-throughput RT-qPCR-based quantification of microRNA (miRNA) expression', Nucleic Acids Research, 2022, vol. 50, No.4, article No. e22, pp. 1-12.

Mei, Q. et al., 'A facile and specific assay for quantifying microRNA by an optimized RT-qPCR approach', 2012, vol. 7, No. 10, article No. e46890, pp. 1-10.

Sun, C. et al., 'The role of the microRNA regulatory network in Alzheimer's disease: a bioinformatics analysis', Arch. Med. Sci., 2022, vol. 18, No. 1, pp. 206-222.

Jung, S. et al., 'In-particle stem-loop RT-qPCR for specific and multiplex microRNA profiling', Biosensors and Bioelectronics, 2020, vol. 163, article No. 112301, pp. 1-7.

Yang, L.-H. et al., 'Universal Stem-Loop Primer Method for Screening and Quantification of MicroRNA', PLoS ONE, 2014, vol. 9, No. 12, article No. e115293, pp. 1-13.

Mao, Q. et al., 'Transcriptome analysis of microRNAs, circRNAs, and mRNAs in the dorsal root ganglia of paclitaxel-induced mice with neuropathic pain', Frontiers in Molecular Neuroscience, Aug. 31, 2022, vol. 15, article No. 990260, pp. 1-14.

* cited by examiner

SEQUENCE LISTING

```
Sequence total quantity: 264
SEQ ID NO: 1            moltype = RNA  length = 22
FEATURE                 Location/Qualifiers
```

-continued

```
source                1..22
                      mol_type = other RNA
                      organism = Homo sapiens
SEQUENCE: 1
tagcagcacg taaatattgg cg                                          22

SEQ ID NO: 2          moltype = RNA  length = 23
FEATURE               Location/Qualifiers
source                1..23
                      mol_type = other RNA
                      organism = Homo sapiens
SEQUENCE: 2
aggcagtgta gttagctgat tgc                                         23

SEQ ID NO: 3          moltype = RNA  length = 22
FEATURE               Location/Qualifiers
source                1..22
                      mol_type = other RNA
                      organism = Homo sapiens
SEQUENCE: 3
ataaagctag ataaccgaaa gt                                          22

SEQ ID NO: 4          moltype = RNA  length = 23
FEATURE               Location/Qualifiers
source                1..23
                      mol_type = other RNA
                      organism = Homo sapiens
SEQUENCE: 4
tctttggtta tctagctgta tga                                         23

SEQ ID NO: 5          moltype = DNA  length = 52
FEATURE               Location/Qualifiers
source                1..52
                      mol_type = other DNA
                      organism = synthetic construct
SEQUENCE: 5
gtcgtatcca gtgcagggtc cgaggtattc gcactggata cgaccgccaa ta         52

SEQ ID NO: 6          moltype = DNA  length = 57
FEATURE               Location/Qualifiers
source                1..57
                      mol_type = other DNA
                      organism = synthetic construct
SEQUENCE: 6
gtctgtatgg ttggataggg atgtgaacca gtcgtgaaca accatacaga cgcaatc    57

SEQ ID NO: 7          moltype = DNA  length = 50
FEATURE               Location/Qualifiers
source                1..50
                      mol_type = other DNA
                      organism = synthetic construct
SEQUENCE: 7
gttggctctg gtgcagggtc cgaggtattc gcaccagagc caacactttc            50

SEQ ID NO: 8          moltype = DNA  length = 69
FEATURE               Location/Qualifiers
source                1..69
                      mol_type = other DNA
                      organism = synthetic construct
SEQUENCE: 8
ggtcgtatgc aaagcagggt ccgaggtatc catcgcacgc atcgcactgc atacgacctc  60
atacagcta                                                          69

SEQ ID NO: 9          moltype = DNA  length = 44
FEATURE               Location/Qualifiers
source                1..44
                      mol_type = other DNA
                      organism = synthetic construct
SEQUENCE: 9
gtcgtatcca gtgcagggtc cgaggtattc gcactggata cgac                  44

SEQ ID NO: 10         moltype = DNA  length = 51
FEATURE               Location/Qualifiers
source                1..51
                      mol_type = other DNA
                      organism = synthetic construct
SEQUENCE: 10
gtctgtatgg ttggataggg atgtgaacca gtcgtgaaca accatacaga c          51
```

```
SEQ ID NO: 11           moltype = DNA  length = 44
FEATURE                 Location/Qualifiers
source                  1..44
                        mol_type = other DNA
                        organism = synthetic construct
SEQUENCE: 11
gttggctctg gtgcagggtc cgaggtattc gcaccagagc caac                  44

SEQ ID NO: 12           moltype = DNA  length = 58
FEATURE                 Location/Qualifiers
source                  1..58
                        mol_type = other DNA
                        organism = synthetic construct
SEQUENCE: 12
ggtcgtatgc aaagcagggt ccgaggtatc catcgcacgc atcgcactgc atacgacc    58

SEQ ID NO: 13           moltype =   length =
SEQUENCE: 13
000

SEQ ID NO: 14           moltype =   length =
SEQUENCE: 14
000

SEQ ID NO: 15           moltype =   length =
SEQUENCE: 15
000

SEQ ID NO: 16           moltype = DNA  length = 11
FEATURE                 Location/Qualifiers
source                  1..11
                        mol_type = other DNA
                        organism = synthetic construct
SEQUENCE: 16
tcatacagct a                                                      11

SEQ ID NO: 17           moltype = DNA  length = 19
FEATURE                 Location/Qualifiers
source                  1..19
                        mol_type = other DNA
                        organism = synthetic construct
SEQUENCE: 17
cgcgcgtctt tggttatct                                              19

SEQ ID NO: 18           moltype = DNA  length = 19
FEATURE                 Location/Qualifiers
source                  1..19
                        mol_type = other DNA
                        organism = synthetic construct
SEQUENCE: 18
gcgcgaggca gtgtagtta                                              19

SEQ ID NO: 19           moltype = DNA  length = 20
FEATURE                 Location/Qualifiers
source                  1..20
                        mol_type = other DNA
                        organism = synthetic construct
SEQUENCE: 19
ttgcgcgcat aaagctagat                                             20

SEQ ID NO: 20           moltype = DNA  length = 21
FEATURE                 Location/Qualifiers
source                  1..21
                        mol_type = other DNA
                        organism = synthetic construct
SEQUENCE: 20
cgcgcgtctt tggttatcta g                                           21

SEQ ID NO: 21           moltype = DNA  length = 16
FEATURE                 Location/Qualifiers
source                  1..16
                        mol_type = other DNA
                        organism = synthetic construct
SEQUENCE: 21
gtgcagggtc cgaggt                                                 16

SEQ ID NO: 22           moltype = DNA  length = 21
FEATURE                 Location/Qualifiers
source                  1..21
```

```
                         mol_type = other DNA
                         organism = synthetic construct
SEQUENCE: 22
ttggataggg atgtgaacca g                                            21

SEQ ID NO: 23            moltype = DNA  length = 16
FEATURE                  Location/Qualifiers
source                   1..16
                         mol_type = other DNA
                         organism = synthetic construct
SEQUENCE: 23
gtgcagggtc cgaggt                                                  16

SEQ ID NO: 24            moltype = DNA  length = 18
FEATURE                  Location/Qualifiers
source                   1..18
                         mol_type = other DNA
                         organism = synthetic construct
SEQUENCE: 24
agcagggtcc gaggtatc                                                18

SEQ ID NO: 25            moltype = DNA  length = 22
FEATURE                  Location/Qualifiers
source                   1..22
                         mol_type = other DNA
                         organism = synthetic construct
SEQUENCE: 25
tggcggtcgt atccagtgcg aa                                           22

SEQ ID NO: 26            moltype = DNA  length = 27
FEATURE                  Location/Qualifiers
source                   1..27
                         mol_type = other DNA
                         organism = synthetic construct
SEQUENCE: 26
ctgattgcgt ctgtatggtt gttcacg                                      27

SEQ ID NO: 27            moltype = DNA  length = 23
FEATURE                  Location/Qualifiers
source                   1..23
                         mol_type = other DNA
                         organism = synthetic construct
SEQUENCE: 27
accgaaagtg ttggctctgg tgc                                          23

SEQ ID NO: 28            moltype = DNA  length = 25
FEATURE                  Location/Qualifiers
source                   1..25
                         mol_type = other DNA
                         organism = synthetic construct
SEQUENCE: 28
tgtatgaggt cgtatgcagt gcgat                                        25

SEQ ID NO: 29            moltype = RNA  length = 22
FEATURE                  Location/Qualifiers
source                   1..22
                         mol_type = other RNA
                         organism = Homo sapiens
SEQUENCE: 29
ctgtgcgtgt gacagcggct ga                                           22

SEQ ID NO: 30            moltype = RNA  length = 22
FEATURE                  Location/Qualifiers
source                   1..22
                         mol_type = other RNA
                         organism = Homo sapiens
SEQUENCE: 30
tcgtaccgtg agtaataatg cg                                           22

SEQ ID NO: 31            moltype = RNA  length = 22
FEATURE                  Location/Qualifiers
source                   1..22
                         mol_type = other RNA
                         organism = Homo sapiens
SEQUENCE: 31
tccttcattc caccggagtc tg                                           22

SEQ ID NO: 32            moltype = RNA  length = 22
FEATURE                  Location/Qualifiers
```

-continued

```
source                  1..22
                        mol_type = other RNA
                        organism = Homo sapiens
SEQUENCE: 32
tcctgtactg agctgccccg ag                                          22

SEQ ID NO: 33           moltype = DNA  length = 52
FEATURE                 Location/Qualifiers
source                  1..52
                        mol_type = other DNA
                        organism = synthetic construct
SEQUENCE: 33
gtcgtatcca gtgcagggtc cgaggtattc gcactggata cgactcagcc gc         52

SEQ ID NO: 34           moltype = DNA  length = 50
FEATURE                 Location/Qualifiers
source                  1..50
                        mol_type = other DNA
                        organism = synthetic construct
SEQUENCE: 34
gtcgtatcca gtgcagggtc cgaggtattc gcactggata cgaccgcatt            50

SEQ ID NO: 35           moltype = DNA  length = 50
FEATURE                 Location/Qualifiers
source                  1..50
                        mol_type = other DNA
                        organism = synthetic construct
SEQUENCE: 35
gtcgtatcca gtgcagggtc cgaggtattc gcactggata cgaccagact            50

SEQ ID NO: 36           moltype = DNA  length = 52
FEATURE                 Location/Qualifiers
source                  1..52
                        mol_type = other DNA
                        organism = synthetic construct
SEQUENCE: 36
gtcgtatcca gtgcagggtc cgaggtattc gcactggata cgacctcggg gc         52

SEQ ID NO: 37           moltype = DNA  length = 44
FEATURE                 Location/Qualifiers
source                  1..44
                        mol_type = other DNA
                        organism = synthetic construct
SEQUENCE: 37
gtcgtatcca gtgcagggtc cgaggtattc gcactggata cgac                  44

SEQ ID NO: 38           moltype =   length =
SEQUENCE: 38
000

SEQ ID NO: 39           moltype =   length =
SEQUENCE: 39
000

SEQ ID NO: 40           moltype =   length =
SEQUENCE: 40
000

SEQ ID NO: 41           moltype =   length =
SEQUENCE: 41
000

SEQ ID NO: 42           moltype = DNA  length = 17
FEATURE                 Location/Qualifiers
source                  1..17
                        mol_type = other DNA
                        organism = synthetic construct
SEQUENCE: 42
atgcctgtgc gtgtgac                                                17

SEQ ID NO: 43           moltype = DNA  length = 16
FEATURE                 Location/Qualifiers
source                  1..16
                        mol_type = other DNA
                        organism = synthetic construct
SEQUENCE: 43
ttcgcgctcg taccgt                                                 16

SEQ ID NO: 44           moltype = DNA  length = 18
```

```
FEATURE                 Location/Qualifiers
source                  1..18
                        mol_type = other DNA
                        organism = synthetic construct
SEQUENCE: 44
ttgccgcctc cttcattc                                                18

SEQ ID NO: 45           moltype = DNA  length = 17
FEATURE                 Location/Qualifiers
source                  1..17
                        mol_type = other DNA
                        organism = synthetic construct
SEQUENCE: 45
gccgcctcct gtactga                                                 17

SEQ ID NO: 46           moltype = DNA  length = 16
FEATURE                 Location/Qualifiers
source                  1..16
                        mol_type = other DNA
                        organism = synthetic construct
SEQUENCE: 46
agcggctgag tcgtat                                                  16

SEQ ID NO: 47           moltype = DNA  length = 21
FEATURE                 Location/Qualifiers
source                  1..21
                        mol_type = other DNA
                        organism = synthetic construct
SEQUENCE: 47
agtaataatg cggtcgtatc c                                            21

SEQ ID NO: 48           moltype = DNA  length = 18
FEATURE                 Location/Qualifiers
source                  1..18
                        mol_type = other DNA
                        organism = synthetic construct
SEQUENCE: 48
ccggagtctg gtcgtatc                                                18

SEQ ID NO: 49           moltype = DNA  length = 17
FEATURE                 Location/Qualifiers
source                  1..17
                        mol_type = other DNA
                        organism = synthetic construct
SEQUENCE: 49
tgccccgagg tcgtatc                                                 17

SEQ ID NO: 50           moltype = DNA  length = 16
FEATURE                 Location/Qualifiers
source                  1..16
                        mol_type = other DNA
                        organism = synthetic construct
SEQUENCE: 50
gtgcagggtc cgaggt                                                  16

SEQ ID NO: 51           moltype = DNA  length = 55
FEATURE                 Location/Qualifiers
source                  1..55
                        mol_type = other DNA
                        organism = synthetic construct
SEQUENCE: 51
gtcgtatcca gtgcagggtc cgaggtattc gcactggata cgactcagcc gctgt       55

SEQ ID NO: 52           moltype = DNA  length = 50
FEATURE                 Location/Qualifiers
source                  1..50
                        mol_type = other DNA
                        organism = synthetic construct
SEQUENCE: 52
gtcgtatcca gtgcagggtc cgaggtattc gcactggata cgactcagcc             50

SEQ ID NO: 53           moltype = DNA  length = 48
FEATURE                 Location/Qualifiers
source                  1..48
                        mol_type = other DNA
                        organism = synthetic construct
SEQUENCE: 53
gtcgtatcca gtgcagggtc cgaggtattc gcactggata cgactcag               48
```

```
SEQ ID NO: 54          moltype = DNA  length = 55
FEATURE                Location/Qualifiers
source                 1..55
                       mol_type = other DNA
                       organism = synthetic construct
SEQUENCE: 54
gtcgtatcca gtgcagggtc cgaggtattc gcactggata cgaccgcatt attac       55

SEQ ID NO: 55          moltype = DNA  length = 48
FEATURE                Location/Qualifiers
source                 1..48
                       mol_type = other DNA
                       organism = synthetic construct
SEQUENCE: 55
gtcgtatcca gtgcagggtc cgaggtattc gcactggata cgaccgca              48

SEQ ID NO: 56          moltype = DNA  length = 55
FEATURE                Location/Qualifiers
source                 1..55
                       mol_type = other DNA
                       organism = synthetic construct
SEQUENCE: 56
gtcgtatcca gtgcagggtc cgaggtattc gcactggata cgaccagact ccggt       55

SEQ ID NO: 57          moltype = DNA  length = 52
FEATURE                Location/Qualifiers
source                 1..52
                       mol_type = other DNA
                       organism = synthetic construct
SEQUENCE: 57
gtcgtatcca gtgcagggtc cgaggtattc gcactggata cgaccagact cc          52

SEQ ID NO: 58          moltype = DNA  length = 48
FEATURE                Location/Qualifiers
source                 1..48
                       mol_type = other DNA
                       organism = synthetic construct
SEQUENCE: 58
gtcgtatcca gtgcagggtc cgaggtattc gcactggata cgaccaga              48

SEQ ID NO: 59          moltype = DNA  length = 55
FEATURE                Location/Qualifiers
source                 1..55
                       mol_type = other DNA
                       organism = synthetic construct
SEQUENCE: 59
gtcgtatcca gtgcagggtc cgaggtattc gcactggata cgacctcggg gcagc       55

SEQ ID NO: 60          moltype = DNA  length = 50
FEATURE                Location/Qualifiers
source                 1..50
                       mol_type = other DNA
                       organism = synthetic construct
SEQUENCE: 60
gtcgtatcca gtgcagggtc cgaggtattc gcactggata cgacctcggg            50

SEQ ID NO: 61          moltype = DNA  length = 48
FEATURE                Location/Qualifiers
source                 1..48
                       mol_type = other DNA
                       organism = synthetic construct
SEQUENCE: 61
gtcgtatcca gtgcagggtc cgaggtattc gcactggata cgacctcg              48

SEQ ID NO: 62          moltype = DNA  length = 55
FEATURE                Location/Qualifiers
source                 1..55
                       mol_type = other DNA
                       organism = synthetic construct
SEQUENCE: 62
gtcgtatcca gtgcagggtc cgaggtattc gcactggata cgaccgccaa tattt       55

SEQ ID NO: 63          moltype = DNA  length = 50
FEATURE                Location/Qualifiers
source                 1..50
                       mol_type = other DNA
                       organism = synthetic construct
SEQUENCE: 63
gtcgtatcca gtgcagggtc cgaggtattc gcactggata cgaccgccaa            50
```

```
SEQ ID NO: 64          moltype = DNA  length = 62
FEATURE                Location/Qualifiers
source                 1..62
                       mol_type = other DNA
                       organism = synthetic construct
SEQUENCE: 64
gtctgtatgg ttggataggg atgtgaacca gtcgtgaaca accatacaga cgcaatcagc  60
ta                                                                  62

SEQ ID NO: 65          moltype = DNA  length = 59
FEATURE                Location/Qualifiers
source                 1..59
                       mol_type = other DNA
                       organism = synthetic construct
SEQUENCE: 65
gtctgtatgg ttggataggg atgtgaacca gtcgtgaaca accatacaga cgcaatcag   59

SEQ ID NO: 66          moltype = DNA  length = 55
FEATURE                Location/Qualifiers
source                 1..55
                       mol_type = other DNA
                       organism = synthetic construct
SEQUENCE: 66
gttggctctg gtgcagggtc cgaggtattc gcaccagagc caacactttc ggtta       55

SEQ ID NO: 67          moltype = DNA  length = 52
FEATURE                Location/Qualifiers
source                 1..52
                       mol_type = other DNA
                       organism = synthetic construct
SEQUENCE: 67
gttggctctg gtgcagggtc cgaggtattc gcaccagagc caacactttc gg          52

SEQ ID NO: 68          moltype = DNA  length = 66
FEATURE                Location/Qualifiers
source                 1..66
                       mol_type = other DNA
                       organism = synthetic construct
SEQUENCE: 68
ggtcgtatgc aaagcagggt ccgaggtatc catcgcacgc atcgcactgc atacgacctc  60
atacag                                                              66

SEQ ID NO: 69          moltype = DNA  length = 64
FEATURE                Location/Qualifiers
source                 1..64
                       mol_type = other DNA
                       organism = synthetic construct
SEQUENCE: 69
ggtcgtatgc aaagcagggt ccgaggtatc catcgcacgc atcgcactgc atacgacctc  60
atac                                                                64

SEQ ID NO: 70          moltype = RNA  length = 23
FEATURE                Location/Qualifiers
source                 1..23
                       mol_type = other RNA
                       organism = Homo sapiens
SEQUENCE: 70
tgtagtgttt cctactttat gga                                           23

SEQ ID NO: 71          moltype = RNA  length = 22
FEATURE                Location/Qualifiers
source                 1..22
                       mol_type = other RNA
                       organism = Homo sapiens
SEQUENCE: 71
taacagtcta cagccatggt cg                                            22

SEQ ID NO: 72          moltype = RNA  length = 22
FEATURE                Location/Qualifiers
source                 1..22
                       mol_type = other RNA
                       organism = Homo sapiens
SEQUENCE: 72
tgagaactga attccatggg tt                                            22

SEQ ID NO: 73          moltype = RNA  length = 22
FEATURE                Location/Qualifiers
source                 1..22
```

```
                        mol_type = other RNA
                        organism = Homo sapiens
SEQUENCE: 73
aaaagctggg ttgagagggc ga                                                22

SEQ ID NO: 74           moltype = RNA  length = 22
FEATURE                 Location/Qualifiers
source                  1..22
                        mol_type = other RNA
                        organism = Homo sapiens
SEQUENCE: 74
gcctgctggg gtggaacctg gt                                                22

SEQ ID NO: 75           moltype = RNA  length = 21
FEATURE                 Location/Qualifiers
source                  1..21
                        mol_type = other RNA
                        organism = Homo sapiens
SEQUENCE: 75
gcagtccatg ggcatataca c                                                 21

SEQ ID NO: 76           moltype = RNA  length = 22
FEATURE                 Location/Qualifiers
source                  1..22
                        mol_type = other RNA
                        organism = Homo sapiens
SEQUENCE: 76
tcctgtactg agctgccccg ag                                                22

SEQ ID NO: 77           moltype = RNA  length = 23
FEATURE                 Location/Qualifiers
source                  1..23
                        mol_type = other RNA
                        organism = Homo sapiens
SEQUENCE: 77
aaaagtgctt acagtgcagg tag                                               23

SEQ ID NO: 78           moltype = RNA  length = 23
FEATURE                 Location/Qualifiers
source                  1..23
                        mol_type = other RNA
                        organism = Homo sapiens
SEQUENCE: 78
agcagcattg tacagggcta tga                                               23

SEQ ID NO: 79           moltype = RNA  length = 22
FEATURE                 Location/Qualifiers
source                  1..22
                        mol_type = other RNA
                        organism = Homo sapiens
SEQUENCE: 79
tcgtaccgtg agtaataatg cg                                                22

SEQ ID NO: 80           moltype = RNA  length = 22
FEATURE                 Location/Qualifiers
source                  1..22
                        mol_type = other RNA
                        organism = Homo sapiens
SEQUENCE: 80
tagcagcaca tcatggttta ca                                                22

SEQ ID NO: 81           moltype = RNA  length = 23
FEATURE                 Location/Qualifiers
source                  1..23
                        mol_type = other RNA
                        organism = Homo sapiens
SEQUENCE: 81
tctcacacag aaatcgcacc cgt                                               23

SEQ ID NO: 82           moltype = RNA  length = 23
FEATURE                 Location/Qualifiers
source                  1..23
                        mol_type = other RNA
                        organism = Homo sapiens
SEQUENCE: 82
agcagcattg tacagggcta tca                                               23

SEQ ID NO: 83           moltype = RNA  length = 22
FEATURE                 Location/Qualifiers
```

```
source                1..22
                      mol_type = other RNA
                      organism = Homo sapiens
SEQUENCE: 83
aacattcaac ctgtcggtga gt                                                22

SEQ ID NO: 84         moltype = RNA  length = 22
FEATURE               Location/Qualifiers
source                1..22
                      mol_type = other RNA
                      organism = Homo sapiens
SEQUENCE: 84
tagcttatca gactgatgtt ga                                                22

SEQ ID NO: 85         moltype = RNA  length = 23
FEATURE               Location/Qualifiers
source                1..23
                      mol_type = other RNA
                      organism = Homo sapiens
SEQUENCE: 85
cgcatcccct agggcattgg tgt                                               23

SEQ ID NO: 86         moltype = RNA  length = 21
FEATURE               Location/Qualifiers
source                1..21
                      mol_type = other RNA
                      organism = Homo sapiens
SEQUENCE: 86
ctagactgaa gctccttgag g                                                 21

SEQ ID NO: 87         moltype = RNA  length = 22
FEATURE               Location/Qualifiers
source                1..22
                      mol_type = other RNA
                      organism = Homo sapiens
SEQUENCE: 87
tagcaccatt tgaaatcggt ta                                                22

SEQ ID NO: 88         moltype = RNA  length = 22
FEATURE               Location/Qualifiers
source                1..22
                      mol_type = other RNA
                      organism = Homo sapiens
SEQUENCE: 88
aaaagctggg ttgagagggc aa                                                22

SEQ ID NO: 89         moltype = RNA  length = 22
FEATURE               Location/Qualifiers
source                1..22
                      mol_type = other RNA
                      organism = Homo sapiens
SEQUENCE: 89
tgaggtagta gtttgtgctg tt                                                22

SEQ ID NO: 90         moltype = RNA  length = 21
FEATURE               Location/Qualifiers
source                1..21
                      mol_type = other RNA
                      organism = Homo sapiens
SEQUENCE: 90
ttcaagtaat tcaggatagg t                                                 21

SEQ ID NO: 91         moltype = RNA  length = 21
FEATURE               Location/Qualifiers
source                1..21
                      mol_type = other RNA
                      organism = Homo sapiens
SEQUENCE: 91
aggggtgcta tctgtgattg a                                                 21

SEQ ID NO: 92         moltype = RNA  length = 22
FEATURE               Location/Qualifiers
source                1..22
                      mol_type = other RNA
                      organism = Homo sapiens
SEQUENCE: 92
tggcagtgtc ttagctggtt gt                                                22

SEQ ID NO: 93         moltype = RNA  length = 23
```

```
FEATURE               Location/Qualifiers
source                1..23
                      mol_type = other RNA
                      organism = Homo sapiens
SEQUENCE: 93
aggcagtgta gttagctgat tgc                                          23

SEQ ID NO: 94         moltype = RNA  length = 22
FEATURE               Location/Qualifiers
source                1..22
                      mol_type = other RNA
                      organism = Homo sapiens
SEQUENCE: 94
agtggggaac ccttccatga gg                                           22

SEQ ID NO: 95         moltype = RNA  length = 22
FEATURE               Location/Qualifiers
source                1..22
                      mol_type = other RNA
                      organism = Homo sapiens
SEQUENCE: 95
tattgcactt gtcccggcct gt                                           22

SEQ ID NO: 96         moltype = RNA  length = 22
FEATURE               Location/Qualifiers
source                1..22
                      mol_type = other RNA
                      organism = Homo sapiens
SEQUENCE: 96
ctatacgacc tgctgccttt ct                                           22

SEQ ID NO: 97         moltype = RNA  length = 22
FEATURE               Location/Qualifiers
source                1..22
                      mol_type = other RNA
                      organism = Homo sapiens
SEQUENCE: 97
ttcaagtaat ccaggatagg ct                                           22

SEQ ID NO: 98         moltype = RNA  length = 22
FEATURE               Location/Qualifiers
source                1..22
                      mol_type = other RNA
                      organism = Homo sapiens
SEQUENCE: 98
catgccttga gtgtaggacc gt                                           22

SEQ ID NO: 99         moltype = RNA  length = 21
FEATURE               Location/Qualifiers
source                1..21
                      mol_type = other RNA
                      organism = Homo sapiens
SEQUENCE: 99
gatctcactt tgttgcccag g                                            21

SEQ ID NO: 100        moltype = RNA  length = 22
FEATURE               Location/Qualifiers
source                1..22
                      mol_type = other RNA
                      organism = Homo sapiens
SEQUENCE: 100
tgaggtagta gattgtatag tt                                           22

SEQ ID NO: 101        moltype = RNA  length = 22
FEATURE               Location/Qualifiers
source                1..22
                      mol_type = other RNA
                      organism = Homo sapiens
SEQUENCE: 101
ttttgtgtct cccattcccc ag                                           22

SEQ ID NO: 102        moltype = RNA  length = 19
FEATURE               Location/Qualifiers
source                1..19
                      mol_type = other RNA
                      organism = Homo sapiens
SEQUENCE: 102
ggtcctgaca tccacggaa                                               19
```

```
SEQ ID NO: 103          moltype = RNA  length = 23
FEATURE                 Location/Qualifiers
source                  1..23
                        mol_type = other RNA
                        organism = Homo sapiens
SEQUENCE: 103
aaaagctggg ttgagagggc gaa                                          23

SEQ ID NO: 104          moltype = DNA  length = 52
FEATURE                 Location/Qualifiers
source                  1..52
                        mol_type = other DNA
                        organism = synthetic construct
SEQUENCE: 104
gtcgtatcca gtgcagggtc cgaggtattc gcactggata cgactccata aa          52

SEQ ID NO: 105          moltype = DNA  length = 52
FEATURE                 Location/Qualifiers
source                  1..52
                        mol_type = other DNA
                        organism = synthetic construct
SEQUENCE: 105
gtcgtatcca gtgcagggtc cgaggtattc gcactggata cgaccgacca tg          52

SEQ ID NO: 106          moltype = DNA  length = 52
FEATURE                 Location/Qualifiers
source                  1..52
                        mol_type = other DNA
                        organism = synthetic construct
SEQUENCE: 106
gtcgtatcca gtgcagggtc cgaggtattc gcactggata cgacaaccca tg          52

SEQ ID NO: 107          moltype = DNA  length = 52
FEATURE                 Location/Qualifiers
source                  1..52
                        mol_type = other DNA
                        organism = synthetic construct
SEQUENCE: 107
gtcgtatcca gtgcagggtc cgaggtattc gcactggata cgactcgccc tc          52

SEQ ID NO: 108          moltype = DNA  length = 52
FEATURE                 Location/Qualifiers
source                  1..52
                        mol_type = other DNA
                        organism = synthetic construct
SEQUENCE: 108
gtcgtatcca gtgcagggtc cgaggtattc gcactggata cgacaccagg tt          52

SEQ ID NO: 109          moltype = DNA  length = 52
FEATURE                 Location/Qualifiers
source                  1..52
                        mol_type = other DNA
                        organism = synthetic construct
SEQUENCE: 109
gtcgtatcca gtgcagggtc cgaggtattc gcactggata cgacgtgtat at          52

SEQ ID NO: 110          moltype = DNA  length = 52
FEATURE                 Location/Qualifiers
source                  1..52
                        mol_type = other DNA
                        organism = synthetic construct
SEQUENCE: 110
gtcgtatcca gtgcagggtc cgaggtattc gcactggata cgacctcggg gc          52

SEQ ID NO: 111          moltype = DNA  length = 52
FEATURE                 Location/Qualifiers
source                  1..52
                        mol_type = other DNA
                        organism = synthetic construct
SEQUENCE: 111
gtcgtatcca gtgcagggtc cgaggtattc gcactggata cgacctacct gc          52

SEQ ID NO: 112          moltype = DNA  length = 52
FEATURE                 Location/Qualifiers
source                  1..52
                        mol_type = other DNA
                        organism = synthetic construct
SEQUENCE: 112
gtcgtatcca gtgcagggtc cgaggtattc gcactggata cgactcatag cc          52
```

```
SEQ ID NO: 113          moltype = DNA  length = 50
FEATURE                 Location/Qualifiers
source                  1..50
                        mol_type = other DNA
                        organism = synthetic construct
SEQUENCE: 113
gtcgtatcca gtgcagggtc cgaggtattc gcactggata cgaccgcatt             50

SEQ ID NO: 114          moltype = DNA  length = 52
FEATURE                 Location/Qualifiers
source                  1..52
                        mol_type = other DNA
                        organism = synthetic construct
SEQUENCE: 114
gtcgtatcca gtgcagggtc cgaggtattc gcactggata cgactgtaaa cc          52

SEQ ID NO: 115          moltype = DNA  length = 52
FEATURE                 Location/Qualifiers
source                  1..52
                        mol_type = other DNA
                        organism = synthetic construct
SEQUENCE: 115
gtcgtatcca gtgcagggtc cgaggtattc gcactggata cgacacgggt gc          52

SEQ ID NO: 116          moltype = DNA  length = 52
FEATURE                 Location/Qualifiers
source                  1..52
                        mol_type = other DNA
                        organism = synthetic construct
SEQUENCE: 116
gtcgtatcca gtgcagggtc cgaggtattc gcactggata cgactgatag cc          52

SEQ ID NO: 117          moltype = DNA  length = 52
FEATURE                 Location/Qualifiers
source                  1..52
                        mol_type = other DNA
                        organism = synthetic construct
SEQUENCE: 117
gtcgtatcca gtgcagggtc cgaggtattc gcactggata cgacactcac cg          52

SEQ ID NO: 118          moltype = DNA  length = 52
FEATURE                 Location/Qualifiers
source                  1..52
                        mol_type = other DNA
                        organism = synthetic construct
SEQUENCE: 118
gtcgtatcca gtgcagggtc cgaggtattc gcactggata cgactcaaca tc          52

SEQ ID NO: 119          moltype = DNA  length = 52
FEATURE                 Location/Qualifiers
source                  1..52
                        mol_type = other DNA
                        organism = synthetic construct
SEQUENCE: 119
gtcgtatcca gtgcagggtc cgaggtattc gcactggata cgacacacca at          52

SEQ ID NO: 120          moltype = DNA  length = 52
FEATURE                 Location/Qualifiers
source                  1..52
                        mol_type = other DNA
                        organism = synthetic construct
SEQUENCE: 120
gtcgtatcca gtgcagggtc cgaggtattc gcactggata cgaccctcaa gg          52

SEQ ID NO: 121          moltype = DNA  length = 52
FEATURE                 Location/Qualifiers
source                  1..52
                        mol_type = other DNA
                        organism = synthetic construct
SEQUENCE: 121
gtcgtatcca gtgcagggtc cgaggtattc gcactggata cgactaaccg at          52

SEQ ID NO: 122          moltype = DNA  length = 52
FEATURE                 Location/Qualifiers
source                  1..52
                        mol_type = other DNA
                        organism = synthetic construct
SEQUENCE: 122
```

```
gtcgtatcca gtgcagggtc cgaggtattc gcactggata cgacttgccc tc          52

SEQ ID NO: 123          moltype = DNA  length = 52
FEATURE                 Location/Qualifiers
source                  1..52
                        mol_type = other DNA
                        organism = synthetic construct
SEQUENCE: 123
gtcgtatcca gtgcagggtc cgaggtattc gcactggata cgacaacagc ac          52

SEQ ID NO: 124          moltype = DNA  length = 52
FEATURE                 Location/Qualifiers
source                  1..52
                        mol_type = other DNA
                        organism = synthetic construct
SEQUENCE: 124
gtcgtatcca gtgcagggtc cgaggtattc gcactggata cgacacctat cc          52

SEQ ID NO: 125          moltype = DNA  length = 52
FEATURE                 Location/Qualifiers
source                  1..52
                        mol_type = other DNA
                        organism = synthetic construct
SEQUENCE: 125
gtcgtatcca gtgcagggtc cgaggtattc gcactggata cgactcaatc ac          52

SEQ ID NO: 126          moltype = DNA  length = 52
FEATURE                 Location/Qualifiers
source                  1..52
                        mol_type = other DNA
                        organism = synthetic construct
SEQUENCE: 126
gtcgtatcca gtgcagggtc cgaggtattc gcactggata cgacacaacc ag          52

SEQ ID NO: 127          moltype = DNA  length = 52
FEATURE                 Location/Qualifiers
source                  1..52
                        mol_type = other DNA
                        organism = synthetic construct
SEQUENCE: 127
gtcgtatcca gtgcagggtc cgaggtattc gcactggata cgacgcaatc ag          52

SEQ ID NO: 128          moltype = DNA  length = 52
FEATURE                 Location/Qualifiers
source                  1..52
                        mol_type = other DNA
                        organism = synthetic construct
SEQUENCE: 128
gtcgtatcca gtgcagggtc cgaggtattc gcactggata cgaccctcat gg          52

SEQ ID NO: 129          moltype = DNA  length = 52
FEATURE                 Location/Qualifiers
source                  1..52
                        mol_type = other DNA
                        organism = synthetic construct
SEQUENCE: 129
gtcgtatcca gtgcagggtc cgaggtattc gcactggata cgacacaggc cg          52

SEQ ID NO: 130          moltype = DNA  length = 52
FEATURE                 Location/Qualifiers
source                  1..52
                        mol_type = other DNA
                        organism = synthetic construct
SEQUENCE: 130
gtcgtatcca gtgcagggtc cgaggtattc gcactggata cgacagaaag gc          52

SEQ ID NO: 131          moltype = DNA  length = 52
FEATURE                 Location/Qualifiers
source                  1..52
                        mol_type = other DNA
                        organism = synthetic construct
SEQUENCE: 131
gtcgtatcca gtgcagggtc cgaggtattc gcactggata cgacagccta tc          52

SEQ ID NO: 132          moltype = DNA  length = 52
FEATURE                 Location/Qualifiers
source                  1..52
                        mol_type = other DNA
                        organism = synthetic construct
```

```
SEQUENCE: 132
gtcgtatcca gtgcagggtc cgaggtattc gcactggata cgacacggtc ct          52

SEQ ID NO: 133          moltype = DNA  length = 52
FEATURE                 Location/Qualifiers
source                  1..52
                        mol_type = other DNA
                        organism = synthetic construct
SEQUENCE: 133
gtcgtatcca gtgcagggtc cgaggtattc gcactggata cgaccctggg ca          52

SEQ ID NO: 134          moltype = DNA  length = 52
FEATURE                 Location/Qualifiers
source                  1..52
                        mol_type = other DNA
                        organism = synthetic construct
SEQUENCE: 134
gtcgtatcca gtgcagggtc cgaggtattc gcactggata cgacaactat ac          52

SEQ ID NO: 135          moltype = DNA  length = 52
FEATURE                 Location/Qualifiers
source                  1..52
                        mol_type = other DNA
                        organism = synthetic construct
SEQUENCE: 135
gtcgtatcca gtgcagggtc cgaggtattc gcactggata cgacctgggg aa          52

SEQ ID NO: 136          moltype = DNA  length = 52
FEATURE                 Location/Qualifiers
source                  1..52
                        mol_type = other DNA
                        organism = synthetic construct
SEQUENCE: 136
gtcgtatcca gtgcagggtc cgaggtattc gcactggata cgacttccgt gg          52

SEQ ID NO: 137          moltype = DNA  length = 52
FEATURE                 Location/Qualifiers
source                  1..52
                        mol_type = other DNA
                        organism = synthetic construct
SEQUENCE: 137
gtcgtatcca gtgcagggtc cgaggtattc gcactggata cgacttcgcc ct          52

SEQ ID NO: 138          moltype = DNA  length = 18
FEATURE                 Location/Qualifiers
source                  1..18
                        mol_type = other DNA
                        organism = synthetic construct
SEQUENCE: 138
gccgcctgta gtgtttcc                                                18

SEQ ID NO: 139          moltype = DNA  length = 18
FEATURE                 Location/Qualifiers
source                  1..18
                        mol_type = other DNA
                        organism = synthetic construct
SEQUENCE: 139
cgccgcctaa cagtctac                                                18

SEQ ID NO: 140          moltype = DNA  length = 18
FEATURE                 Location/Qualifiers
source                  1..18
                        mol_type = other DNA
                        organism = synthetic construct
SEQUENCE: 140
cgcgcgtgag aactgaat                                                18

SEQ ID NO: 141          moltype = DNA  length = 16
FEATURE                 Location/Qualifiers
source                  1..16
                        mol_type = other DNA
                        organism = synthetic construct
SEQUENCE: 141
ccgcgaaaag ctgggt                                                  16

SEQ ID NO: 142          moltype = DNA  length = 15
FEATURE                 Location/Qualifiers
source                  1..15
                        mol_type = other DNA
```

```
                        organism = synthetic construct
SEQUENCE: 142
ttcgcctgct ggggt                                                15

SEQ ID NO: 143          moltype = DNA  length = 15
FEATURE                 Location/Qualifiers
source                  1..15
                        mol_type = other DNA
                        organism = synthetic construct
SEQUENCE: 143
tccgccgcag tccat                                                15

SEQ ID NO: 144          moltype = DNA  length = 17
FEATURE                 Location/Qualifiers
source                  1..17
                        mol_type = other DNA
                        organism = synthetic construct
SEQUENCE: 144
gccgcctcct gtactga                                              17

SEQ ID NO: 145          moltype = DNA  length = 19
FEATURE                 Location/Qualifiers
source                  1..19
                        mol_type = other DNA
                        organism = synthetic construct
SEQUENCE: 145
gccgccaaaa gtgcttaca                                            19

SEQ ID NO: 146          moltype = DNA  length = 16
FEATURE                 Location/Qualifiers
source                  1..16
                        mol_type = other DNA
                        organism = synthetic construct
SEQUENCE: 146
cgcgcagcag cattgt                                               16

SEQ ID NO: 147          moltype = DNA  length = 16
FEATURE                 Location/Qualifiers
source                  1..16
                        mol_type = other DNA
                        organism = synthetic construct
SEQUENCE: 147
ttcgcgctcg taccgt                                               16

SEQ ID NO: 148          moltype = DNA  length = 16
FEATURE                 Location/Qualifiers
source                  1..16
                        mol_type = other DNA
                        organism = synthetic construct
SEQUENCE: 148
cgcgctagca gcacat                                               16

SEQ ID NO: 149          moltype = DNA  length = 17
FEATURE                 Location/Qualifiers
source                  1..17
                        mol_type = other DNA
                        organism = synthetic construct
SEQUENCE: 149
gcgcgctctc acacaga                                              17

SEQ ID NO: 150          moltype = DNA  length = 18
FEATURE                 Location/Qualifiers
source                  1..18
                        mol_type = other DNA
                        organism = synthetic construct
SEQUENCE: 150
cgcgcgagca gcattgta                                             18

SEQ ID NO: 151          moltype = DNA  length = 18
FEATURE                 Location/Qualifiers
source                  1..18
                        mol_type = other DNA
                        organism = synthetic construct
SEQUENCE: 151
cgcgcgaaca ttcaacct                                             18

SEQ ID NO: 152          moltype = DNA  length = 19
FEATURE                 Location/Qualifiers
source                  1..19
```

```
                        mol_type = other DNA
                        organism = synthetic construct
SEQUENCE: 152
gcgcgcgtag cttatcaga                                                19

SEQ ID NO: 153          moltype = DNA  length = 15
FEATURE                 Location/Qualifiers
source                  1..15
                        mol_type = other DNA
                        organism = synthetic construct
SEQUENCE: 153
gcggcgcatc cccta                                                    15

SEQ ID NO: 154          moltype = DNA  length = 17
FEATURE                 Location/Qualifiers
source                  1..17
                        mol_type = other DNA
                        organism = synthetic construct
SEQUENCE: 154
cgccgcccta gactgaa                                                  17

SEQ ID NO: 155          moltype = DNA  length = 17
FEATURE                 Location/Qualifiers
source                  1..17
                        mol_type = other DNA
                        organism = synthetic construct
SEQUENCE: 155
gccgcctagc accattt                                                  17

SEQ ID NO: 156          moltype = DNA  length = 17
FEATURE                 Location/Qualifiers
source                  1..17
                        mol_type = other DNA
                        organism = synthetic construct
SEQUENCE: 156
ccgccaaaag ctgggtt                                                  17

SEQ ID NO: 157          moltype = DNA  length = 18
FEATURE                 Location/Qualifiers
source                  1..18
                        mol_type = other DNA
                        organism = synthetic construct
SEQUENCE: 157
gcgcgtgagg tagtagtt                                                 18

SEQ ID NO: 158          moltype = DNA  length = 20
FEATURE                 Location/Qualifiers
source                  1..20
                        mol_type = other DNA
                        organism = synthetic construct
SEQUENCE: 158
gcgcgcgttc aagtaattca                                               20

SEQ ID NO: 159          moltype = DNA  length = 16
FEATURE                 Location/Qualifiers
source                  1..16
                        mol_type = other DNA
                        organism = synthetic construct
SEQUENCE: 159
tcgcgagggg tgctat                                                   16

SEQ ID NO: 160          moltype = DNA  length = 15
FEATURE                 Location/Qualifiers
source                  1..15
                        mol_type = other DNA
                        organism = synthetic construct
SEQUENCE: 160
cgcgtggcag tgtct                                                    15

SEQ ID NO: 161          moltype = DNA  length = 18
FEATURE                 Location/Qualifiers
source                  1..18
                        mol_type = other DNA
                        organism = synthetic construct
SEQUENCE: 161
ttccggaggc agtgtagt                                                 18

SEQ ID NO: 162          moltype = DNA  length = 16
FEATURE                 Location/Qualifiers
```

-continued

```
source                1..16
                      mol_type = other DNA
                      organism = synthetic construct
SEQUENCE: 162
gcggcggagt ggggaa                                                   16

SEQ ID NO: 163        moltype = DNA  length = 18
FEATURE               Location/Qualifiers
source                1..18
                      mol_type = other DNA
                      organism = synthetic construct
SEQUENCE: 163
cggcggtatt gcacttgt                                                 18

SEQ ID NO: 164        moltype = DNA  length = 16
FEATURE               Location/Qualifiers
source                1..16
                      mol_type = other DNA
                      organism = synthetic construct
SEQUENCE: 164
gcgcgctata cgacct                                                   16

SEQ ID NO: 165        moltype = DNA  length = 21
FEATURE               Location/Qualifiers
source                1..21
                      mol_type = other DNA
                      organism = synthetic construct
SEQUENCE: 165
cgcgcgcgtt caagtaatcc a                                             21

SEQ ID NO: 166        moltype = DNA  length = 16
FEATURE               Location/Qualifiers
source                1..16
                      mol_type = other DNA
                      organism = synthetic construct
SEQUENCE: 166
cgcgcatgcc ttgagt                                                   16

SEQ ID NO: 167        moltype = DNA  length = 16
FEATURE               Location/Qualifiers
source                1..16
                      mol_type = other DNA
                      organism = synthetic construct
SEQUENCE: 167
cgcgcggatc tcactt                                                   16

SEQ ID NO: 168        moltype = DNA  length = 18
FEATURE               Location/Qualifiers
source                1..18
                      mol_type = other DNA
                      organism = synthetic construct
SEQUENCE: 168
cggcggtgag gtagtaga                                                 18

SEQ ID NO: 169        moltype = DNA  length = 18
FEATURE               Location/Qualifiers
source                1..18
                      mol_type = other DNA
                      organism = synthetic construct
SEQUENCE: 169
ttcggcggtt ttgtgtct                                                 18

SEQ ID NO: 170        moltype = DNA  length = 15
FEATURE               Location/Qualifiers
source                1..15
                      mol_type = other DNA
                      organism = synthetic construct
SEQUENCE: 170
gcggcggtcc tgaca                                                    15

SEQ ID NO: 171        moltype = DNA  length = 17
FEATURE               Location/Qualifiers
source                1..17
                      mol_type = other DNA
                      organism = synthetic construct
SEQUENCE: 171
ggcggaaaag ctgggtt                                                  17

SEQ ID NO: 172        moltype = DNA  length = 20
```

```
FEATURE                Location/Qualifiers
source                 1..20
                       mol_type = other DNA
                       organism = synthetic construct
SEQUENCE: 172
ctttatggag tcgtatccag                                             20

SEQ ID NO: 173         moltype = DNA  length = 15
FEATURE                Location/Qualifiers
source                 1..15
                       mol_type = other DNA
                       organism = synthetic construct
SEQUENCE: 173
gccatggtcg gtcgt                                                  15

SEQ ID NO: 174         moltype = DNA  length = 17
FEATURE                Location/Qualifiers
source                 1..17
                       mol_type = other DNA
                       organism = synthetic construct
SEQUENCE: 174
tccatgggtt gtcgtat                                                17

SEQ ID NO: 175         moltype = DNA  length = 16
FEATURE                Location/Qualifiers
source                 1..16
                       mol_type = other DNA
                       organism = synthetic construct
SEQUENCE: 175
tgagagggcg agtcgt                                                 16

SEQ ID NO: 176         moltype = DNA  length = 15
FEATURE                Location/Qualifiers
source                 1..15
                       mol_type = other DNA
                       organism = synthetic construct
SEQUENCE: 176
ggaacctggt gtcgt                                                  15

SEQ ID NO: 177         moltype = DNA  length = 16
FEATURE                Location/Qualifiers
source                 1..16
                       mol_type = other DNA
                       organism = synthetic construct
SEQUENCE: 177
gggcatatac acgtcg                                                 16

SEQ ID NO: 178         moltype = DNA  length = 17
FEATURE                Location/Qualifiers
source                 1..17
                       mol_type = other DNA
                       organism = synthetic construct
SEQUENCE: 178
tgccccgagg tcgtatc                                                17

SEQ ID NO: 179         moltype = DNA  length = 17
FEATURE                Location/Qualifiers
source                 1..17
                       mol_type = other DNA
                       organism = synthetic construct
SEQUENCE: 179
gtgcaggtag gtcgtat                                                17

SEQ ID NO: 180         moltype = DNA  length = 17
FEATURE                Location/Qualifiers
source                 1..17
                       mol_type = other DNA
                       organism = synthetic construct
SEQUENCE: 180
acagggctat gagtcgt                                                17

SEQ ID NO: 181         moltype = DNA  length = 21
FEATURE                Location/Qualifiers
source                 1..21
                       mol_type = other DNA
                       organism = synthetic construct
SEQUENCE: 181
agtaataatg cggtcgtatc c                                           21
```

```
SEQ ID NO: 182         moltype = DNA  length = 21
FEATURE                Location/Qualifiers
source                 1..21
                       mol_type = other DNA
                       organism = synthetic construct
SEQUENCE: 182
tggtttacag tcgtatccag t                                              21

SEQ ID NO: 183         moltype = DNA  length = 17
FEATURE                Location/Qualifiers
source                 1..17
                       mol_type = other DNA
                       organism = synthetic construct
SEQUENCE: 183
tcgcacccgt gtcgtat                                                   17

SEQ ID NO: 184         moltype = DNA  length = 18
FEATURE                Location/Qualifiers
source                 1..18
                       mol_type = other DNA
                       organism = synthetic construct
SEQUENCE: 184
cagggctatc agtcgtat                                                  18

SEQ ID NO: 185         moltype = DNA  length = 17
FEATURE                Location/Qualifiers
source                 1..17
                       mol_type = other DNA
                       organism = synthetic construct
SEQUENCE: 185
gtcggtgagt gtcgtat                                                   17

SEQ ID NO: 186         moltype = DNA  length = 21
FEATURE                Location/Qualifiers
source                 1..21
                       mol_type = other DNA
                       organism = synthetic construct
SEQUENCE: 186
ctgatgttga gtcgtatcca g                                              21

SEQ ID NO: 187         moltype = DNA  length = 17
FEATURE                Location/Qualifiers
source                 1..17
                       mol_type = other DNA
                       organism = synthetic construct
SEQUENCE: 187
gggcattggt gtgtcgt                                                   17

SEQ ID NO: 188         moltype = DNA  length = 16
FEATURE                Location/Qualifiers
source                 1..16
                       mol_type = other DNA
                       organism = synthetic construct
SEQUENCE: 188
gctccttgag ggtcgt                                                    16

SEQ ID NO: 189         moltype = DNA  length = 21
FEATURE                Location/Qualifiers
source                 1..21
                       mol_type = other DNA
                       organism = synthetic construct
SEQUENCE: 189
gaaatcggtt agtcgtatcc a                                              21

SEQ ID NO: 190         moltype = DNA  length = 15
FEATURE                Location/Qualifiers
source                 1..15
                       mol_type = other DNA
                       organism = synthetic construct
SEQUENCE: 190
gagagggcaa gtcgt                                                     15

SEQ ID NO: 191         moltype = DNA  length = 19
FEATURE                Location/Qualifiers
source                 1..19
                       mol_type = other DNA
                       organism = synthetic construct
SEQUENCE: 191
tgtgctgttg tcgtatcca                                                 19
```

```
SEQ ID NO: 192          moltype = DNA  length = 20
FEATURE                 Location/Qualifiers
source                  1..20
                        mol_type = other DNA
                        organism = synthetic construct
SEQUENCE: 192
ggataggtgt cgtatccagt                                                        20

SEQ ID NO: 193          moltype = DNA  length = 20
FEATURE                 Location/Qualifiers
source                  1..20
                        mol_type = other DNA
                        organism = synthetic construct
SEQUENCE: 193
ctgtgattga gtcgtatcca                                                        20

SEQ ID NO: 194          moltype = DNA  length = 18
FEATURE                 Location/Qualifiers
source                  1..18
                        mol_type = other DNA
                        organism = synthetic construct
SEQUENCE: 194
tagctggttg tgtcgtat                                                          18

SEQ ID NO: 195          moltype = DNA  length = 18
FEATURE                 Location/Qualifiers
source                  1..18
                        mol_type = other DNA
                        organism = synthetic construct
SEQUENCE: 195
tagctgattg cgtcgtat                                                          18

SEQ ID NO: 196          moltype = DNA  length = 18
FEATURE                 Location/Qualifiers
source                  1..18
                        mol_type = other DNA
                        organism = synthetic construct
SEQUENCE: 196
cttccatgag ggtcgtat                                                          18

SEQ ID NO: 197          moltype = DNA  length = 18
FEATURE                 Location/Qualifiers
source                  1..18
                        mol_type = other DNA
                        organism = synthetic construct
SEQUENCE: 197
cggcctgtgt cgtatcca                                                          18

SEQ ID NO: 198          moltype = DNA  length = 20
FEATURE                 Location/Qualifiers
source                  1..20
                        mol_type = other DNA
                        organism = synthetic construct
SEQUENCE: 198
ctgcctttct gtcgtatcca                                                        20

SEQ ID NO: 199          moltype = DNA  length = 17
FEATURE                 Location/Qualifiers
source                  1..17
                        mol_type = other DNA
                        organism = synthetic construct
SEQUENCE: 199
ccaggatagg ctgtcgt                                                           17

SEQ ID NO: 200          moltype = DNA  length = 19
FEATURE                 Location/Qualifiers
source                  1..19
                        mol_type = other DNA
                        organism = synthetic construct
SEQUENCE: 200
taggaccgtg tcgtatcca                                                         19

SEQ ID NO: 201          moltype = DNA  length = 16
FEATURE                 Location/Qualifiers
source                  1..16
                        mol_type = other DNA
                        organism = synthetic construct
SEQUENCE: 201
```

```
tgttgcccag ggtcgt                                                     16

SEQ ID NO: 202        moltype = DNA  length = 21
FEATURE               Location/Qualifiers
source                1..21
                      mol_type = other DNA
                      organism = synthetic construct
SEQUENCE: 202
tgtatagttg tcgtatccag t                                               21

SEQ ID NO: 203        moltype = DNA  length = 18
FEATURE               Location/Qualifiers
source                1..18
                      mol_type = other DNA
                      organism = synthetic construct
SEQUENCE: 203
ccattcccca ggtcgtat                                                   18

SEQ ID NO: 204        moltype = DNA  length = 21
FEATURE               Location/Qualifiers
source                1..21
                      mol_type = other DNA
                      organism = synthetic construct
SEQUENCE: 204
tccacggaag tcgtatccag t                                               21

SEQ ID NO: 205        moltype = DNA  length = 18
FEATURE               Location/Qualifiers
source                1..18
                      mol_type = other DNA
                      organism = synthetic construct
SEQUENCE: 205
gagagggcga agtcgtat                                                   18

SEQ ID NO: 206        moltype = RNA  length = 22
FEATURE               Location/Qualifiers
source                1..22
                      mol_type = other RNA
                      organism = Homo sapiens
SEQUENCE: 206
tagcttatca gactgatgtt ga                                              22

SEQ ID NO: 207        moltype = RNA  length = 22
FEATURE               Location/Qualifiers
source                1..22
                      mol_type = other RNA
                      organism = Homo sapiens
SEQUENCE: 207
taatactgcc tggtaatgat ga                                              22

SEQ ID NO: 208        moltype = RNA  length = 22
FEATURE               Location/Qualifiers
source                1..22
                      mol_type = other RNA
                      organism = Homo sapiens
SEQUENCE: 208
tccttcattc caccggagtc tg                                              22

SEQ ID NO: 209        moltype = RNA  length = 22
FEATURE               Location/Qualifiers
source                1..22
                      mol_type = other RNA
                      organism = Homo sapiens
SEQUENCE: 209
tcctgtactg agctgccccg ag                                              22

SEQ ID NO: 210        moltype = RNA  length = 22
FEATURE               Location/Qualifiers
source                1..22
                      mol_type = other RNA
                      organism = Homo sapiens
SEQUENCE: 210
tcgtaccgtg agtaataatg cg                                              22

SEQ ID NO: 211        moltype = RNA  length = 22
FEATURE               Location/Qualifiers
source                1..22
                      mol_type = other RNA
                      organism = Homo sapiens
```

```
SEQUENCE: 211
tgtcagtttg tcaaataccc ca                                              22

SEQ ID NO: 212          moltype = RNA  length = 23
FEATURE                 Location/Qualifiers
source                  1..23
                        mol_type = other RNA
                        organism = Homo sapiens
SEQUENCE: 212
tgagtgtgtg tgtgtgagtg tgt                                             23

SEQ ID NO: 213          moltype = RNA  length = 22
FEATURE                 Location/Qualifiers
source                  1..22
                        mol_type = other RNA
                        organism = Homo sapiens
SEQUENCE: 213
caatcactaa ctccactgcc at                                              22

SEQ ID NO: 214          moltype = RNA  length = 24
FEATURE                 Location/Qualifiers
source                  1..24
                        mol_type = other RNA
                        organism = Homo sapiens
SEQUENCE: 214
agcctggaag ctggagcctg cagt                                            24

SEQ ID NO: 215          moltype = RNA  length = 22
FEATURE                 Location/Qualifiers
source                  1..22
                        mol_type = other RNA
                        organism = Homo sapiens
SEQUENCE: 215
tccctgagac cctaacttgt ga                                              22

SEQ ID NO: 216          moltype = RNA  length = 22
FEATURE                 Location/Qualifiers
source                  1..22
                        mol_type = other RNA
                        organism = Homo sapiens
SEQUENCE: 216
taacactgtc tggtaaagat gg                                              22

SEQ ID NO: 217          moltype = RNA  length = 24
FEATURE                 Location/Qualifiers
source                  1..24
                        mol_type = other RNA
                        organism = Homo sapiens
SEQUENCE: 217
ttaatgctaa tcgtgatagg ggtt                                            24

SEQ ID NO: 218          moltype = RNA  length = 22
FEATURE                 Location/Qualifiers
source                  1..22
                        mol_type = other RNA
                        organism = Homo sapiens
SEQUENCE: 218
aactggccct caaagtcccg ct                                              22

SEQ ID NO: 219          moltype = RNA  length = 25
FEATURE                 Location/Qualifiers
source                  1..25
                        mol_type = other RNA
                        organism = Homo sapiens
SEQUENCE: 219
agtggttctt aacagttcaa cagtt                                           25

SEQ ID NO: 220          moltype = RNA  length = 22
FEATURE                 Location/Qualifiers
source                  1..22
                        mol_type = other RNA
                        organism = Homo sapiens
SEQUENCE: 220
ctgtgcgtgt gacagcggct ga                                              22

SEQ ID NO: 221          moltype = RNA  length = 21
FEATURE                 Location/Qualifiers
source                  1..21
                        mol_type = other RNA
```

```
                         organism = Homo sapiens
SEQUENCE: 221
agctacatct ggctactggg t                                              21

SEQ ID NO: 222           moltype = RNA  length = 22
FEATURE                  Location/Qualifiers
source                   1..22
                         mol_type = other RNA
                         organism = Homo sapiens
SEQUENCE: 222
tagcaccatt tgaaatcggt ta                                             22

SEQ ID NO: 223           moltype = RNA  length = 23
FEATURE                  Location/Qualifiers
source                   1..23
                         mol_type = other RNA
                         organism = Homo sapiens
SEQUENCE: 223
tccctgtcct ccaggagctc acg                                            23

SEQ ID NO: 224           moltype = RNA  length = 22
FEATURE                  Location/Qualifiers
source                   1..22
                         mol_type = other RNA
                         organism = Homo sapiens
SEQUENCE: 224
taatactgtc tggtaaaacc gt                                             22

SEQ ID NO: 225           moltype = RNA  length = 23
FEATURE                  Location/Qualifiers
source                   1..23
                         mol_type = other RNA
                         organism = Homo sapiens
SEQUENCE: 225
tgagaactga attccatagg ctg                                            23

SEQ ID NO: 226           moltype = RNA  length = 22
FEATURE                  Location/Qualifiers
source                   1..22
                         mol_type = other RNA
                         organism = Homo sapiens
SEQUENCE: 226
tctcccaacc cttgtaccag tg                                             22

SEQ ID NO: 227           moltype = RNA  length = 22
FEATURE                  Location/Qualifiers
source                   1..22
                         mol_type = other RNA
                         organism = Homo sapiens
SEQUENCE: 227
cgaatcatta tttgctgctc ta                                             22

SEQ ID NO: 228           moltype = RNA  length = 22
FEATURE                  Location/Qualifiers
source                   1..22
                         mol_type = other RNA
                         organism = Homo sapiens
SEQUENCE: 228
tagcagcacg taaatattgg cg                                             22

SEQ ID NO: 229           moltype = RNA  length = 23
FEATURE                  Location/Qualifiers
source                   1..23
                         mol_type = other RNA
                         organism = Homo sapiens
SEQUENCE: 229
taaagtgctt atagtgcagg tag                                            23

SEQ ID NO: 230           moltype = RNA  length = 23
FEATURE                  Location/Qualifiers
source                   1..23
                         mol_type = other RNA
                         organism = Homo sapiens
SEQUENCE: 230
tagcaccatt tgaaatcagt gtt                                            23

SEQ ID NO: 231           moltype = RNA  length = 23
FEATURE                  Location/Qualifiers
source                   1..23
```

```
                        mol_type = other RNA
                        organism = Homo sapiens
SEQUENCE: 231
cagtgcaata gtattgtcaa agc                                              23

SEQ ID NO: 232          moltype = RNA  length = 22
FEATURE                 Location/Qualifiers
source                  1..22
                        mol_type = other RNA
                        organism = Homo sapiens
SEQUENCE: 232
tgtaaacatc ctacactcag ct                                               22

SEQ ID NO: 233          moltype = RNA  length = 22
FEATURE                 Location/Qualifiers
source                  1..22
                        mol_type = other RNA
                        organism = Homo sapiens
SEQUENCE: 233
tggcagtgtc ttagctggtt gt                                               22

SEQ ID NO: 234          moltype = RNA  length = 24
FEATURE                 Location/Qualifiers
source                  1..24
                        mol_type = other RNA
                        organism = Homo sapiens
SEQUENCE: 234
gttccacact gacactgcag aagt                                             24

SEQ ID NO: 235          moltype = RNA  length = 17
FEATURE                 Location/Qualifiers
source                  1..17
                        mol_type = other RNA
                        organism = Homo sapiens
SEQUENCE: 235
accccactcc tggtacc                                                     17

SEQ ID NO: 236          moltype = DNA  length = 52
FEATURE                 Location/Qualifiers
source                  1..52
                        mol_type = other DNA
                        organism = synthetic construct
SEQUENCE: 236
gtcgtatcca gtgcagggtc cgaggtattc gcactggata cgactcaaca tc              52

SEQ ID NO: 237          moltype = DNA  length = 50
FEATURE                 Location/Qualifiers
source                  1..50
                        mol_type = other DNA
                        organism = synthetic construct
SEQUENCE: 237
gtcgtatcca gtgcagggtc cgaggtattc gcactggata cgaccagact                 50

SEQ ID NO: 238          moltype = DNA  length = 52
FEATURE                 Location/Qualifiers
source                  1..52
                        mol_type = other DNA
                        organism = synthetic construct
SEQUENCE: 238
gtcgtatcca gtgcagggtc cgaggtattc gcactggata cgacctcggg gc              52

SEQ ID NO: 239          moltype = DNA  length = 50
FEATURE                 Location/Qualifiers
source                  1..50
                        mol_type = other DNA
                        organism = synthetic construct
SEQUENCE: 239
gtcgtatcca gtgcagggtc cgaggtattc gcactggata cgaccgcatt                 50

SEQ ID NO: 240          moltype = DNA  length = 52
FEATURE                 Location/Qualifiers
source                  1..52
                        mol_type = other DNA
                        organism = synthetic construct
SEQUENCE: 240
gtcgtatcca gtgcagggtc cgaggtattc gcactggata cgactcagcc gc              52

SEQ ID NO: 241          moltype = DNA  length = 52
FEATURE                 Location/Qualifiers
```

```
source                  1..52
                        mol_type = other DNA
                        organism = synthetic construct
SEQUENCE: 241
gtcgtatcca gtgcagggtc cgaggtattc gcactggata cgactaaccg at          52

SEQ ID NO: 242          moltype = DNA  length = 52
FEATURE                 Location/Qualifiers
source                  1..52
                        mol_type = other DNA
                        organism = synthetic construct
SEQUENCE: 242
gtcgtatcca gtgcagggtc cgaggtattc gcactggata cgaccgccaa ta          52

SEQ ID NO: 243          moltype = DNA  length = 52
FEATURE                 Location/Qualifiers
source                  1..52
                        mol_type = other DNA
                        organism = synthetic construct
SEQUENCE: 243
gtcgtatcca gtgcagggtc cgaggtattc gcactggata cgacacaacc ag          52

SEQ ID NO: 244          moltype = DNA  length = 19
FEATURE                 Location/Qualifiers
source                  1..19
                        mol_type = other DNA
                        organism = synthetic construct
SEQUENCE: 244
gcgcgcgtag cttatcaga                                               19

SEQ ID NO: 245          moltype = DNA  length = 18
FEATURE                 Location/Qualifiers
source                  1..18
                        mol_type = other DNA
                        organism = synthetic construct
SEQUENCE: 245
ttgccgcctc cttcattc                                                18

SEQ ID NO: 246          moltype = DNA  length = 17
FEATURE                 Location/Qualifiers
source                  1..17
                        mol_type = other DNA
                        organism = synthetic construct
SEQUENCE: 246
gccgcctcct gtactga                                                 17

SEQ ID NO: 247          moltype = DNA  length = 16
FEATURE                 Location/Qualifiers
source                  1..16
                        mol_type = other DNA
                        organism = synthetic construct
SEQUENCE: 247
ttcgcgctcg taccgt                                                  16

SEQ ID NO: 248          moltype = DNA  length = 17
FEATURE                 Location/Qualifiers
source                  1..17
                        mol_type = other DNA
                        organism = synthetic construct
SEQUENCE: 248
atgcctgtgc gtgtgac                                                 17

SEQ ID NO: 249          moltype = DNA  length = 17
FEATURE                 Location/Qualifiers
source                  1..17
                        mol_type = other DNA
                        organism = synthetic construct
SEQUENCE: 249
gccgcctagc accattt                                                 17

SEQ ID NO: 250          moltype = DNA  length = 19
FEATURE                 Location/Qualifiers
source                  1..19
                        mol_type = other DNA
                        organism = synthetic construct
SEQUENCE: 250
cgcgcgtctt tggttatct                                               19

SEQ ID NO: 251          moltype = DNA  length = 15
```

```
FEATURE                Location/Qualifiers
source                 1..15
                       mol_type = other DNA
                       organism = synthetic construct
SEQUENCE: 251
cgcgtggcag tgtct                                              15

SEQ ID NO: 252         moltype = DNA  length = 21
FEATURE                Location/Qualifiers
source                 1..21
                       mol_type = other DNA
                       organism = synthetic construct
SEQUENCE: 252
ctgatgttga gtcgtatcca g                                       21

SEQ ID NO: 253         moltype = DNA  length = 18
FEATURE                Location/Qualifiers
source                 1..18
                       mol_type = other DNA
                       organism = synthetic construct
SEQUENCE: 253
ccggagtctg gtcgtatc                                           18

SEQ ID NO: 254         moltype = DNA  length = 17
FEATURE                Location/Qualifiers
source                 1..17
                       mol_type = other DNA
                       organism = synthetic construct
SEQUENCE: 254
tgccccgagg tcgtatc                                            17

SEQ ID NO: 255         moltype = DNA  length = 21
FEATURE                Location/Qualifiers
source                 1..21
                       mol_type = other DNA
                       organism = synthetic construct
SEQUENCE: 255
agtaataatg cggtcgtatc c                                       21

SEQ ID NO: 256         moltype = DNA  length = 16
FEATURE                Location/Qualifiers
source                 1..16
                       mol_type = other DNA
                       organism = synthetic construct
SEQUENCE: 256
agcggctgag tcgtat                                             16

SEQ ID NO: 257         moltype = DNA  length = 21
FEATURE                Location/Qualifiers
source                 1..21
                       mol_type = other DNA
                       organism = synthetic construct
SEQUENCE: 257
gaaatcggtt agtcgtatcc a                                       21

SEQ ID NO: 258         moltype = DNA  length = 22
FEATURE                Location/Qualifiers
source                 1..22
                       mol_type = other DNA
                       organism = synthetic construct
SEQUENCE: 258
tggcggtcgt atccagtgcg aa                                      22

SEQ ID NO: 259         moltype = DNA  length = 18
FEATURE                Location/Qualifiers
source                 1..18
                       mol_type = other DNA
                       organism = synthetic construct
SEQUENCE: 259
tagctggttg tgtcgtat                                           18

SEQ ID NO: 260         moltype = DNA  length = 18
FEATURE                Location/Qualifiers
source                 1..18
                       mol_type = other DNA
                       organism = synthetic construct
SEQUENCE: 260
tcgtgtcgtc gtcgtacc                                           18
```

-continued

```
SEQ ID NO: 261          moltype = DNA  length = 22
FEATURE                 Location/Qualifiers
source                  1..22
                        mol_type = other DNA
                        organism = synthetic construct
SEQUENCE: 261
ctcgtcgtgt cgctccttca tt                                              22

SEQ ID NO: 262          moltype = DNA  length = 18
FEATURE                 Location/Qualifiers
source                  1..18
                        mol_type = other DNA
                        organism = synthetic construct
SEQUENCE: 262
caccggagtc tggtcgta                                                   18

SEQ ID NO: 263          moltype = DNA  length = 19
FEATURE                 Location/Qualifiers
source                  1..19
                        mol_type = other DNA
                        organism = synthetic construct
SEQUENCE: 263
tgagtaataa tgcggtcgt                                                  19

SEQ ID NO: 264          moltype = DNA  length = 15
FEATURE                 Location/Qualifiers
source                  1..15
                        mol_type = other DNA
                        organism = synthetic construct
SEQUENCE: 264
ctgccccgag gtcgt                                                      15
```

METHOD FOR SCREENING MULTIPLEX REVERSE TRANSCRIPTION PRIMER COMBINATIONS FOR QUANTIFYING MULTIPLE MIRNAS

CROSS-REFERENCE TO RELATED PATENT APPLICATIONS

This application is a continuation application of International Patent Application No. PCT/US2023/67520, filed on May 26, 2023, which further claims its priority to PCT Patent Application Serial No. PCT/CN2023/092571, filed on May 6, 2023, all of which are incorporated herein in their entireties by reference.

The PCT Patent Application Serial No. PCT/US2023/67520 is related to co-pending PCT patent applications PCT/US2023/67522, PCT/US2023/67524, PCT/US2023/67528, PCT/US2023/67531, which were filed on the same day that the application PCT/US2023/67520 was filed, and with the same applicant as that of the application PCT/US2023/67520, which are incorporated herein by reference in their entireties.

STATEMENT REGARDING THE SEQUENCE LISTINGS

The Sequence Listings associated with this application are provided in xml format in lieu of a paper copy and are hereby incorporated by reference into the specification. The name of the xml file containing the Sequence Listings is 1010469_100WO1.xml. The xml file is about 225 KB, was created on Apr. 26, 2023.

FIELD OF THE INVENTION

The present invention relates to a method for selecting and screening multiplex stem-loop reverse transcription primer combinations for quantifying multiple target miRNAs simultaneously.

BACKGROUND OF THE INVENTION

The background description provided herein is for the purpose of generally presenting the context of the present invention. The subject matter discussed in the background of the invention section should not be assumed to be prior art merely as a result of its mention in the background of the invention section. Similarly, a problem mentioned in the background of the invention section or associated with the subject matter of the background of the invention section should not be assumed to have been previously recognized in the prior art. The subject matter in the background of the invention section merely represents different approaches, which in and of themselves may also be inventions.

MicroRNA or miRNA is a micro non-coding single-stranded RNA. According to miRBase (ver. 22), human genome encodes approximately 2,600 mature miRNAs. Relevant studies have indicated that these miRNAs involve in numerous biological processes and their regulations, such as cell apoptosis, proliferation, organogenesis, development, tumorigenesis and hematopoiesis. Meanwhile, miRNA also regulates gene expressions in post-transcription stage, and thus plays an essential role for regulating multiple life courses such as, disease genesis and development, as well as cell senescence. Existing researches have indicated that changes in the expression levels of multiple miRNAs in particular combinations are useful for the screening, diagnosis and prognosis of many diseases.

It wasn't until 1993 when Lee et al. cloned lin-4 using positional cloning from the nematode *Caenorhabditis elegans*, that the first miRNA was discovered. It was found that the lin-4 gene encodes for a miRNA of approximately 22 nucleotides in length. Later, in 2000, Reinhart et al. discovered let-7, which is the second gene known to regulate temporal development in the worm, and is a negative regulator that is also transcribed into a miRNA of 21 nucleotides. Since then, people have gradually realized that miRNAs are evolutionarily conserved important molecules that play a regulatory role in disease development and biological evolution.

Despite the potential for miRNAs to be used as a diagnostic tool for disease and their significant regulatory role, their accurate quantification is extremely difficult. Real-time fluorescent quantitative PCR (qPCR) detection is considered the gold standard for quantitative detection, but it was not applicable for miRNA quantification in the early days of research. This was due to the fact that miRNAs have very short sequences, low expression levels in cells, and highly homologous sequences. RNA blot hybridization and gene chips were the main methods used to study miRNA expressions in the early days, but these methods had limitations in terms of sample requirement, linear range, and sensitivity.

Currently, singleplex detection for a particular target miRNA can be achieved via singleplex reverse transcription-singleplex quantitative PCR (RT-qPCR). Specifically, the target miRNA is being reverse transcribed into cDNA with reverse transcription primers in a reverse transcription (RT), and then reverse transcription products including the cDNA undergoes fluorescence quantitative PCR (qPCR) for quantifying the target miRNA.

Because the length of a miRNA is generally short and typically ranges from 18 nt to 25 nt, it is difficult to obtain the reverse transcription products, e.g. cDNA, having a length suitable for qPCR. To resolve this issue, various miRNA reverse transcription techniques are aimed at extending the length of the reverse transcription product, e.g. cDNA. Among them, the stem-loop reverse transcription is a preferred reverse transcription method which effectively extends the length of the reverse transcription product. Specifically, the reverse transcription primer used in the method has a stem-loop structure sequence and an anchor sequence complementary pairing to a 3' sequence of the target miRNA. The stem-loop structure can effectively extend the length of the sequences of the reverse transcription products, and can prevent itself from pairing to other sequence structures due to its self-complementary structure, and therefore reducing non-specific binding. Once the reverse transcription is accomplished, the reverse transcription products obtained via the reverse transcription undergo qPCR in which forward/reverse primers and a specific fluorescent probe are added. Common probes include Taqman® probes (a single DNA oligo containing a 5' reporter dye and a 3' quencher) and MGB probes. The target miRNA is quantified in the qPCR, and a quantification result in form of Ct value would be provided.

In 2005, Chen et al. first implemented real-time fluorescent qPCR detection of a single miRNA using the stem-loop method (C. Chen, et al. (2005) Real-time quantification of microRNAs by stem-loop RT-PCR, Nucleic Acids Res., 33, e179). The detection process includes two main steps: reverse transcription and real-time PCR. In the first step, the stem-loop reverse transcription primer is mixed with the miRNA molecule, and a reverse transcription is performed using the MultiScribe™ reverse transcriptase a recombinant moloney murine leukemia virus (rMoMuLV) reverse transcriptase optimized for TaqMan®-based assays. The resulting product is then quantitatively analyzed using conventional Taqman® PCR. The stem-loop primer used has a 6-base complementary sequence to the 3' end of the miRNA to initiate the reverse transcription reaction. In their experiment, it was observed that the stem-loop primer has better specificity and sensitivity compared to traditional linear primers. Nucleotide bases stacking can effectively improve thermal stability, and the spatial structure of the stem-loop sequence may facilitate its binding with double-stranded DNA molecules in the genome. They also suggested that the stem-loop reverse transcription primer has the potential to be used in multiple reverse transcription reactions and may have better efficiency and specificity.

To simultaneously detect/quantify multiple miRNAs in small samples, Tang et al. (2006) further improved the above method to achieve simultaneous detection of the expressions of 220 miRNAs in a single embryonic stem cell (Tang et al. (2006) MicroRNA expression profiling of single whole embryonic stem cells, Nucleic acids Res 24 e9). The method mainly involves reverse transcription of all miRNAs in a single embryonic stem cell under cyclic pulse temperature, followed by pre-PCR to increase the detection sensitivity of the resulting product, and then separate real-time fluorescence quantification of each miRNA expression. Lao et al. (2006) validated Tang's method and believed that as the number of detections increases, the mutual reaction between primers will also increase. The difference between the Ct values obtained for a certain miRNA under single and multiple detection conditions using the above method is observable. Therefore, the results obtained by this method still need to be verified under single detection conditions. Lao et al. also believed that this interaction between primers needs to be deeply analyzed and studied to be reduced, and this research requires testing a large number of primer combinations. Among the known 326 human miRNAs, this work is expensive and difficult for any laboratory. Currently, when studying the relationship between disease and the expression levels of multiple miRNAs, only Chen et al.'s single quantification detection method is used to fluorescence quantitatively detect miRNA expression levels separately.

Thus, there exists a major defect in this field of technology, namely, it is hardly to achieve multiplex quantification using the RT-qPCR-quantifying multiple target miRNAs simultaneously. Also, it is difficult to achieve a stable standardized control. As a result, in order to quantifying the multiple target miRNAs whose expression level changes relate to a particular disease, singleplex RT-qPCR for each of the target miRNAs has to be accomplished separately, and thus significantly increasing the cost and the time consumption. This defect is the biggest obstacle for clinical use of the miRNA detection/quantification, i.e. diagnosis method for diseases.

Therefore, there remains an imperative need for a multiplex quantification method which is capable of quantifying a combination of multiple target miRNAs simultaneously.

SUMMARY OF THE INVENTION

In light of the foregoing, this invention discloses a method for selecting and screening a stem-loop reverse transcription primer combination which is capable of quantifying a combination of multiple target miRNAs simultaneously.

In one aspect of the invention, the invention discloses a method for screening a multiplex stem-loop reverse transcription primer combination demonstrating multi-specificity for quantifying a plurality of target miRNAs simultaneously, the method comprising (A) providing the plurality of target miRNAs, wherein each of the plurality of target miRNAs has a unique 3' sequence; (B) providing a plurality of stem-loop reverse transcription primers, wherein each of the plurality of stem-loop reverse transcription primers has a stem-loop sequence forming a stem-loop structure and an anchor sequence complimentary to the unique 3' sequence of one of the plurality of target miRNAs, wherein the plurality of stem-loop reverse transcription primers are selected by a selection process comprising a) selecting the stem-loop sequence for each of the plurality of stem-loop reverse transcription primers; and b) selecting a certain length for the anchor sequence of each of the plurality of stem-loop reverse transcription primers, wherein the lengths of the anchor sequences of at least two of the plurality of stem-loop reverse transcription primers are different from each other; (C) screening the plurality of stem-loop reverse transcription primers by a screening process or determining the multi-specificity of the plurality of stem-loop reverse transcription primers, wherein the screening process comprises i) separately performing a process of singleplex reverse transcription for each of the plurality of stem-loop reverse transcription primers using a mixed target miRNAs template comprising the plurality of target miRNAs to be quantified; ii) separately collecting a collection of reverse transcription products from each of the separate singleplex reverse transcription processes of step i); iii) separately performing a process of multiplex qPCR amplification for each of the collections of reverse transcription products from step ii) to form a collection of multiplex qPCR products for each of the collections of reverse transcription products; iv) separately obtaining a quantification result of each of the plurality of target miRNAs based on each of the collections of multiplex qPCR products and therefrom obtaining a collection of the quantification results of the plurality of target miRNAs; and v) determining the multi-specificity of the plurality of stem-loop reverse transcription primers based on the collection of quantification results formed in step iv), wherein the multi-specificity of the plurality of stem-loop reverse transcription primers is confirmed when the collection of quantification results shows that each of the plurality of stem-loop reverse transcription primers effectively and only reverse transcribes the target miRNA to which the anchor sequence of each of the plurality of stem-loop reverse transcription primer is complimentary; and (D) modifying, if the multi-specificity of the plurality of stem-loop reverse transcription primers is not confirmed by the collection of quantification results, the plurality of stem-loop reverse transcription primers by a repeat process comprising providing a modified plurality of stem-loop reverse transcription primers by repeating step b) of the selection process to select a new length for the anchor sequence of each of those of the plurality of stem-loop reverse transcription primers which fail to effectively and only reverse transcribe the target miRNA to which the anchor sequence of the stem-loop reverse transcription primer is complimentary, wherein the length of the anchor sequence is selected between 3 nt to 12 nt; and repeating steps i)-v) of the screening process to determine the multi-specificity of the modified plurality of stem-loop reverse transcription primers, until the modified plurality of stem-loop reverse transcription primers demonstrates the multi-specificity and operatively quantifies the plurality of target miRNAs simultaneously.

In one embodiment, step i) of the screening process comprises a hybridization reaction wherein each of the plurality of stem-loop reverse transcription primers is hybridized to at least one of the plurality of target miRNA to form a collection of at least one type of miRNA-stem-loop reverse transcription primer complex; and an extension reaction wherein at least one type of cDNA is formed by extending a 3' of the stem-loop reverse transcription primer in the collection of at least one type of miRNA-stem-loop reverse transcription primer complex.

In one embodiment, the step iii) of the screening process comprises adding a combination of forward primers and at least one reverse primer to each of the collections of reverse transcription products from step ii); wherein each of the forward primers has a sequence same to a 5' sequence of one of the plurality of target miRNAs; adding a combination of probes to each of the collections of reverse transcription products from step ii); wherein each of the probes has a sequence same as a portion of one of the target miRNA, and each of the probes has a fluorescent reporter group different from the fluorescent reporter groups of the other probes, and each of the probes has a quencher group suppressing a fluorescent light produced by the fluorescent reporter group; separately amplifying each of the collections of reverse transcription products from step ii) with the combination of forward primers, the at least one reverse primer, and the combination of probes to separately form a collection of multiplex qPCR products for each of the collections of reverse transcription products; detecting a strength of the fluorescent light produced by the fluorescent reporter groups of the combination of probes in each of the collections of multiplex qPCR products; and quantifying each of the plurality of target miRNAs based on the strength of the fluorescent light detected in each of the collections of multiplex qPCR products.

In one embodiment, the quantification result of each of the plurality of target miRNA comprises a Ct value.

In one embodiment, the stem-loop sequences of at least two of the plurality of stem-loop reverse transcription primers selected in step a) are the same.

In one embodiment, each of the unique 3' sequences of the plurality of target miRNAs is different from the other unique 3' sequences of the plurality of target miRNAs by at least 1 nt.

In one embodiment, the method further comprising a sensitivity test of the plurality of stem-loop reverse transcription primers, wherein the sensitivity test comprises 1) preparing a plurality templates of mixed target miRNAs having a concentration gradient, wherein each of the plurality templates of mixed target miRNAs has a concentration different from the other templates of mixed target miRNAs; 2) separately performing a process of singleplex reverse transcription on each of the mixed target miRNA templates with each of the plurality of stem-loop reverse transcription primers and collecting a collection of reverse transcription products from each of the processes of singleplex reverse transcription; 3) separately performing a process of multiplex qPCR using each of the collection of reverse transcription products from step 2), and obtaining a collection of quantification results of each of the target miRNAs from each of the processes of multiplex qPCR; 4) arranging the collection of quantification results by each of the plurality of stem-loop reverse transcription primers; 5) determining the lowest concentration of the mixed target miRNAs template for each of the plurality of stem-loop reverse transcription primers based on the arranged quantification results.

In one embodiment, the stem-loop sequence of at least two of the plurality of stem-loop reverse transcription primers are the same.

In one embodiment, the stem-loop sequence of all the plurality of stem-loop reverse transcription primers are the same.

In one embodiment, the plurality of target miRNAs comprises a combination of any two or more of hsa-miR-210-3p, hsa-miR-126-3p, hsa-miR-205-5p and hsa-miR-486-5p.

In one embodiment, the plurality of target miRNAs comprises a combination of any two or more of miR-16-5p, miR-34c-5p, miR-9-3p and miR-9-5p.

In another aspect of the invention, a method for screening a multiplex stem-loop reverse transcription primer combination demonstrating multi-specificity for quantifying a plurality of target miRNAs simultaneously, comprising the steps of (A) providing the plurality of target miRNAs, wherein each of the plurality of target miRNAs has a unique 3' sequence; (B) providing a plurality of stem-loop reverse transcription primers, wherein each of the plurality of stem-loop reverse transcription primers has a stem-loop sequence forming a stem-loop structure and an anchor sequence complimentary to the unique 3' sequence of one of the plurality of target miRNAs, and wherein the lengths of the anchor sequences of at least two of the plurality of stem-loop reverse transcription primers are different from each other; (C) screening the plurality of stem-loop reverse transcription primers to determine the multi-specificity of the plurality of stem-loop reverse transcription primers, wherein the multi-specificity of the plurality of stem-loop reverse transcription primers is confirmed when each of the plurality of stem-loop reverse transcription primers effectively and only reverse transcribes the target miRNA to which the anchor sequence of each of the plurality of stem-loop reverse transcription primer is complimentary; and (D) modifying, if the multi-specificity of the plurality of stem-loop reverse transcription primers is not confirmed, the plurality of stem-loop reverse transcription primers by a repeat process until the modified plurality of stem-loop reverse transcription primers demonstrates the multi-specificity and operatively quantifies the plurality of target miRNAs simultaneously.

In another aspect of the invention, a multiplex reverse transcription primer combination for simultaneously quantifying a plurality of target miRNAs, the multiplex reverse transcription primer combination comprising a plurality of stem-loop reverse transcription primers; wherein each of the plurality of stem-loop reverse transcription primers has a stem-loop sequence forming a stem-loop structure and an anchor sequence complimentary to a unique 3' sequence of one of the plurality of target miRNAs, wherein the lengths of the anchor sequences of at least two of the plurality of stem-loop reverse transcription primers are different from each other.

In one embodiment, each of the plurality of stem-loop reverse transcription primers has a length of about 40-65 nt.

In one embodiment, the anchor sequence of each of the plurality of stem-loop reverse transcription primers has a length of about 3-12 nt.

In one embodiment, the plurality of stem-loop reverse transcription primers comprises a first stem-loop reverse transcription primer having a first stem-loop sequence and a first anchor sequence; and a second stem-loop reverse transcription primer having a second stem-loop sequence and a second anchor sequence; and the plurality of target miRNAs comprises a first target miRNA and a second target miRNA.

In one embodiment, the first anchor sequence of the first stem-loop reverse transcription primer is complimentary to a 3' sequence of the first target miRNA and the second anchor sequence of the second stem-loop reverse transcription primer is complimentary to a 3' sequence of the second target miRNA.

In one embodiment, when a multiplex reverse transcription is conducted using a mixed target miRNAs template comprising the first target miRNA and the second target miRNA and the multiplex reverse transcription primer combination, the first stem-loop reverse transcription primer effectively and only reverse transcribes the first target miRNA; and the second stem-loop reverse transcription primer effectively and only reverse transcribes the second target miRNA.

In one embodiment, the first stem-loop sequence of the first stem-loop reverse transcription primer and the second stem-loop sequence of the second stem-loop reverse transcription primer are the same.

In one embodiment, the plurality of stem-loop reverse transcription primers further comprises a third stem-loop reverse transcription primer having a third stem-loop sequence and a third anchor sequence, wherein the third anchor sequence is complimentary to a 3' sequence of a third target miRNA of the plurality of target miRNAs.

In one embodiment, the plurality of stem-loop reverse transcription primers further comprises a fourth stem-loop reverse transcription primer having a fourth stem-loop sequence and a fourth anchor sequence, wherein the fourth anchor sequence is complimentary to a 3' sequence of a fourth target miRNA of the plurality of target miRNAs.

In one embodiment, the multiplex reverse transcription primer combination has multi-specificity such that the first stem-loop reverse transcription primer effectively and only reverse transcribes the first target miRNA, the second stem-loop reverse transcription primer effectively and only reverse transcribes the second target miRNA, the third stem-loop reverse transcription primer effectively and only reverse transcribes the third target miRNA, and the fourth stem-loop reverse transcription primer effectively and only reverse transcribes the fourth target miRNA.

In one embodiment, at least two of the first, second, third, and fourth stem-loop structures are the same.

In one embodiment, all of the first, second, third, and fourth stem-loop structures are the same.

In one embodiment, each of the first, second, third and fourth fluorescent reporter groups comprises one of VIC® (2'-chloro-7'-phenyl-1,4-dichloro-6-carboxyfluorescein), CY5® (Cyanine5 or Sulfo-Cyanine5), ROX™ (carboxy-X-rhodamine), FAM™ (specifically 6-carboxyfluorescein), and each of the first, second, third and fourth quencher groups comprises one of BHQ1, BHQ2, BHQ3, and MGB.

In another aspect of the invention, a kit for simultaneously quantifying expression level of a plurality of target miRNAs, the kit comprising a multiplex reverse transcription primer combination having at least a first stem-loop reverse transcription primer and a second stem-loop reverse transcription primer; wherein the first stem-loop reverse transcription primer has a first stem-loop sequence and a first anchor sequence; and the second stem-loop reverse transcription primer has a second stem-loop sequence and a second anchor sequence; a first and second forward primers, wherein the first forward primer comprises a Tm-enhancing tail and a first forward primer sequence, and the second forward primer comprises a second Tm-enhancing tail and a second forward primer sequence; at least one reverse primer; wherein the at least one reverse primer is complimentary to the first and the second stem-loop sequences; and first and second probes, wherein the first probe comprises a first probe sequence same as a portion of the first stem-loop reverse transcription primer, a first fluorescent reporter group, and a first quencher group; and the second probe comprises a second probe sequence same as a portion of the second stem-loop reverse transcription primer, a second fluorescent reporter group, and a second quencher group; wherein the first fluorescent reporter group is different from the second fluorescent reporter agent.

In one embodiment, each of the first and second stem-loop reverse transcription primers has a length of about 40-65 nt.

In one embodiment, each of the first and second anchor sequences has a length of about 3-12 nt.

In one embodiment, the first anchor sequence is complimentary to a 3' sequence of a first target miRNA of the plurality of target miRNAs, and the second anchor sequence is complimentary to a 3' sequence of a second target miRNA of the plurality of target miRNAs.

In one embodiment, the first stem-loop sequence of the first stem-loop reverse transcription primer and the second stem-loop sequence of the second stem-loop reverse transcription primer are the same.

In one embodiment, the length of the first anchor sequence of the first stem-loop reverse transcription primer is different from the length of the second anchor sequence of the second stem-loop reverse transcription primer.

In one embodiment, the multiplex reverse transcription primer combination further comprises a third stem-loop reverse transcription primer and a fourth stem-loop reverse transcription primer; wherein the third stem-loop reverse transcription primer has a third stem-loop sequence and a third anchor sequence; and the fourth stem-loop reverse transcription primer has a fourth stem-loop sequence and a fourth anchor sequence; third and fourth forward primers, wherein the third forward primer comprises a third Tm-enhancing tail and a third forward primer sequence, and the fourth forward primer comprises a fourth Tm-enhancing tail and a fourth forward primer sequence; and third and fourth probes, wherein the third probe comprises a third probe sequence same to a portion of the third stem-loop reverse transcription primer, a third fluorescent reporter group, and a third quencher group; the fourth probe comprises a fourth probe sequence same to a portion of the fourth stem-loop reverse transcription primer, a fourth fluorescent reporter group, and a fourth quencher group; wherein each of the first, second, third, and fourth fluorescent reporter groups is different from the other fluorescent reporter groups.

In one embodiment, each of the first, second, third and fourth probe is a Taqman® probe or a MGB probe.

In one aspect of the invention, a method of using quantification results of a plurality of target miRNAs in a living subject for determining a physiological or mental condition of the living subject, the method comprising collecting a biological sample from the living subject; extracting a miRNA sample having the plurality of target miRNAs from the biological sample, wherein the plurality of target miRNAs comprises a first target miRNA and a second target miRNA; performing a multiplex reverse transcription process on the miRNA sample using a multiplex stem-loop reverse transcription primer combination; wherein the multiplex stem-loop reverse transcription primer combination comprises a first stem-loop reverse transcription primer having a first stem-loop sequence and a first anchor sequence and a second stem-loop reverse transcription primer having a second stem-loop sequence and a second anchor sequence, wherein the first anchor sequence is complementary to a 3' sequence of the first target miRNA, and the second anchor sequence is complementary to a 3' sequence of the second target miRNA, and wherein the first anchor sequence of the first stem-loop reverse transcription primer has a length that is different from the second anchor sequence of the second stem-loop reverse transcription primer; collecting a collection of multiplex reverse transcription products from the multiplex reverse transcription process, performing a multiplex qPCR process on the collection of reverse transcription products so as to obtain a quantification result for each of the plurality of target miRNAs; obtaining a collection of quantification results of the plurality of target miRNAs; and using the collection of quantification results of the plurality of target miRNAs for determining the physiological or mental condition of the living subject; wherein the plurality of targets miRNAs are selected based on the physiological or mental condition to be determined; and wherein the multiplex stem-loop reverse transcription primer combination has multi-specificity.

In one embodiment, the plurality of targets miRNAs is selected based on the physiological or mental condition to be determined.

In one embodiment, wherein the plurality of targets miRNAs comprises at least a first target miRNA and a second target miRNA.

In one embodiment, the multiplex reverse transcription primer combination comprises a first stem-loop reverse transcription primer having a first stem-loop sequence and a first anchor sequence; and a second stem-loop reverse transcription primer having a second stem-loop sequence and a second anchor sequence.

In one embodiment, the first anchor sequence of the first stem-loop reverse transcription primer is complementary to a 3' sequence of the first target miRNA and the second anchor sequence of the second stem-loop reverse transcription primer is complementary to a 3' sequence of the second target miRNA, wherein the first anchor sequence of the first stem-loop reverse transcription primer has a length that is different from the second anchor sequence of the second stem-loop reverse transcription primer.

In one embodiment, each of the first and second stem-loop reverse transcription primers has a length of about 40-65 nt.

In one embodiment, each of the first and second anchor sequences has a length of about 3-12 nt.

In one embodiment, during the reverse transcription process of the plurality of target miRNAs, the first stem-loop reverse transcription primer effectively and only reverse transcribes the first target miRNA; and the second stem-loop reverse transcription primer effectively and only reverse transcribes the second target miRNA.

In one embodiment, the first stem-loop sequence of the first stem-loop reverse transcription primer and the second stem-loop sequence of the second stem-loop reverse transcription primer are the same.

In one embodiment, the first stem-loop sequence of the first stem-loop reverse transcription primer is different from the second stem-loop sequence of the second stem-loop reverse transcription primer.

In one embodiment, the multiplex reverse transcription primer combination further comprises a third stem-loop reverse transcription primer having a third stem-loop sequence and a third anchor sequence, wherein the third anchor sequence is complimentary to a 3' sequence of a third target miRNA of the plurality of target miRNAs.

In one embodiment, the multiplex reverse transcription primer combination further comprises a fourth stem-loop reverse transcription primer having a fourth stem-loop sequence and a fourth anchor sequence, wherein the fourth anchor sequence is complimentary to a 3' sequence of a fourth target miRNA of the plurality of target miRNAs.

In one embodiment, the multiplex qPCR process is performed using a combination of forward primers, at least one reverse primer, and a combination of probes.

In one embodiment, each of the forward primers is complimentary to the collection of reverse transcription products of only one of the plurality of target miRNAs, and each of the probes is complimentary to the collection of reverse transcription products of only one of the target miRNAs.

In one embodiment, each of the probes comprises a fluorescent reporter and a quencher group, and the fluorescent reporter of each of the probes is different from the fluorescent reporters of the other probes.

In one embodiment, each of the probes is a Taqman® probe or a MGB probe.

BRIEF DESCRIPTION OF THE DRAWINGS

The accompanying drawings illustrate one or more embodiments of the invention and together with the written description, serve to explain the principles of the invention. Wherever possible, the same reference numbers are used throughout the drawings to refer to the same or like elements of an embodiment.

FIG. 1A shows a selection process and a screening process for a combination of four stem-loop reverse transcription primers. FIG. 1B shows a selection process and a screening process for a combination of multiple stem-loop reverse transcription primers.

FIG. 2A shows the amplification plots of miR-16-5p/ddH$_2$O using its corresponding stem-loop reverse transcription primer with different anchor sequence lengths (6/8/11 nt). FIG. 2B shows the amplification plots of miR-34c-5p/ddH$_2$O using its corresponding stem-loop reverse transcription primer with different anchor sequence lengths (6/8/11 nt). FIG. 2C shows the amplification plots of miR-9-3p/ddH$_2$O using its corresponding stem-loop reverse transcription primer with different anchor sequence lengths (6/8/11 nt). FIG. 2D shows the amplification plots of miR-9-5p/ddH$_2$O using its corresponding stem-loop reverse transcription primer with different anchor sequence lengths (6/8/11 nt).

FIG. 3A shows the amplification plots of singleplex RT-multiplex qPCR using the stem-loop reverse transcription primer screened for miR-9-3p and the mixed miRNA template. FIG. 3B shows the amplification plots of singleplex RT-multiplex qPCR using the stem-loop reverse transcription primer screened for miR-34c-5p and the mixed miRNA template. FIG. 3C shows the amplification plots of singleplex RT-multiplex qPCR using the stem-loop reverse transcription primer screened for miR-9-5p and the mixed miRNA template. FIG. 3D shows the amplification plots of singleplex RT-multiplex qPCR using the stem-loop reverse transcription primer screened for miR-16-5p and the mixed miRNA template. FIG. 3E shows the amplification plots of singleplex RT-multiplex qPCR using the combination of the stem-loop reverse transcription primers and the $ddH_2O$ as a negative control.

FIG. 4A shows the sensitivity test result of the stem-loop reverse transcription primer screened for miR-9-5p. FIG. 4B shows the sensitivity test result of the stem-loop reverse transcription primer screened for miR-9-3p. FIG. 4C shows the sensitivity test result of the stem-loop reverse transcription primer screened for miR-16-5p. and FIG. 4D shows the sensitivity test result of the stem-loop reverse transcription primer screened for miR-34c-5p.

FIG. 5A shows the amplification plot of miR-34c-5p using the singleplex reverse transcription. FIG. 5B shows the amplification plot of miR-9-5p using the singleplex reverse transcription. FIG. 5C shows the amplification plot of miR-9-3p using the singleplex reverse transcription. FIG. 5D shows the amplification plot of miR-16-5p using the singleplex reverse transcription. FIG. 5E shows the amplification plots of the multiplex reverse transcription using the stem-loop reverse transcription combination. FIG. 5F is a schematic diagram showing the comparison of Ct values of the target miRNAs using the singleplex reverse transcription and the multiplex reverse transcription.

FIG. 6A shows the amplification plots of singleplex RT-qPCR of miR-210-3p using its stem-loop reverse transcription primer with the different anchor sequence lengths (4/6/8/11 nt). FIG. 6B shows the amplification plots of singleplex RT-qPCR of the negative control using miR-210-3p stem-loop reverse transcription primer with the different anchor sequence lengths (4/6/8/11 nt). FIG. 6C shows the amplification plots of singleplex RT-qPCR of miR-126-3p using its stem-loop reverse transcription primer with the different anchor sequence lengths (4/6/8/11 nt). FIG. 6D shows the amplification plots of singleplex RT-qPCR of the negative control using miR-126-3p stem-loop reverse transcription primer with the different anchor sequence lengths (4/6/8/11 nt). FIG. 6E shows the amplification plots of singleplex RT-qPCR of miR-205-5p using its stem-loop reverse transcription primer with the different anchor sequence lengths (4/6/8/11 nt). FIG. 6F shows the amplification plots of singleplex RT-qPCR of the negative control using miR-205-5p stem-loop reverse transcription primer with the different anchor sequence lengths (4/6/8/11 nt). FIG. 6G shows the amplification plots of singleplex RT-qPCR of miR-486-5p using its stem-loop reverse transcription primer with the different anchor sequence lengths (4/6/8/11 nt). FIG. 6H shows the amplification plots of singleplex RT-qPCR of the negative control using miR-486-3p stem-loop reverse transcription primer with the different anchor sequence lengths (4/6/8/11 nt).

FIG. 7A shows the amplification plot of singleplex RT-multiplex qPCR of hsa-miR-210-3p using its stem-loop reverse transcription primer. FIG. 7B shows the amplification plot of singleplex RT-multiplex qPCR of hsa-miR-126-3p using its stem-loop reverse transcription primer. FIG. 7C shows the amplification plot of singleplex RT-multiplex qPCR of hsa-miR-205-5p using its stem-loop reverse transcription primer. FIG. 7D shows the amplification plot of singleplex RT-multiplex qPCR of hsa-miR-486-5p using its stem-loop reverse transcription primer.

FIG. 8A shows the sensitivity test result of hsa-miR-210-3p. FIG. 8B shows the sensitivity test result of hsa-miR-126-3p. FIG. 8C shows the sensitivity test result of hsa-miR-205-5p. FIG. 8D shows the sensitivity test result of hsa-miR-486-5p.

FIG. 10A shows the qPCR results using fluorescent reporter group VIC®. FIG. 10B shows the qPCR results using fluorescent reporter group ROX™. FIG. 10C shows the qPCR results using fluorescent reporter group CY5®. FIG. 10D shows the qPCR results using fluorescent reporter group FAM™.

DETAILED DESCRIPTION OF THE INVENTION

Figure 1A:
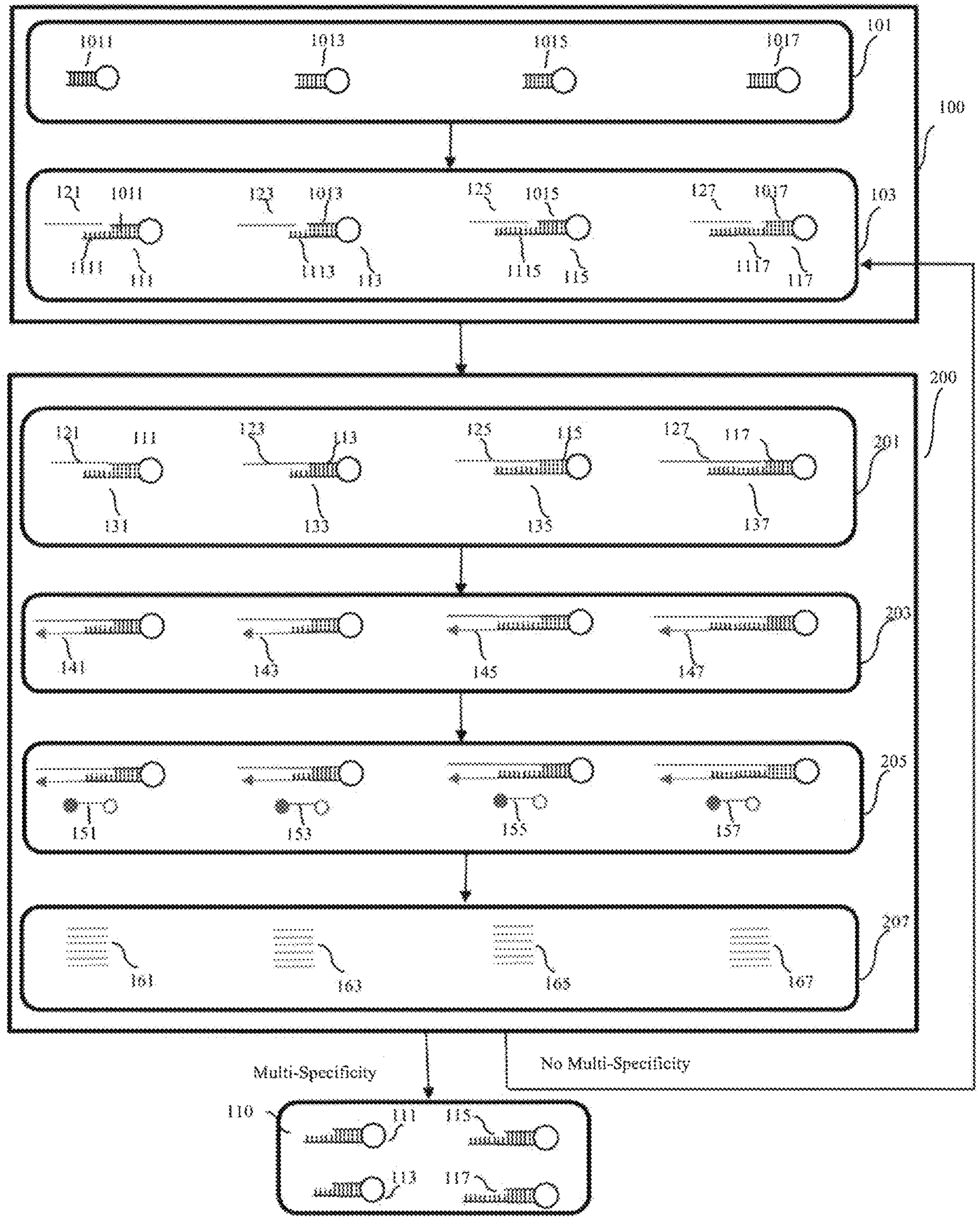
FIGS. 1A-B show a diagram of a selection process for selecting a combination of stem-loop reverse transcription primers, and a screening process testing multi-specificity of the selected stem-loop reverse transcription primer combination.

The invention will now be described more fully hereinafter with reference to the accompanying drawings, in which exemplary embodiments of the invention are shown. This invention may, however, be embodied in many different forms and should not be construed as limited to the embodiments set forth herein. Rather, these embodiments are provided so that this invention will be thorough and complete, and will fully convey the scope of the invention to those skilled in the art. Like reference numerals refer to like elements throughout.

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

One of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the invention has been specifically disclosed by preferred embodiments and optional features, modification and variation of the concepts herein disclosed may be resorted to by those skilled in the art, and that such modifications and variations are considered to be within the scope of this invention as defined by the appended claims.

Whenever a range is given in the specification, for example, a temperature range, a time range, or a composition or concentration range, all intermediate ranges and subranges, as well as all individual values included in the ranges given are intended to be included in the invention. It will be understood that any subranges or individual values in a range or subrange that are included in the description herein can be excluded from the claims herein.

It will be understood that, as used in the description herein and throughout the claims that follow, the meaning of “a”, “an”, and “the” includes plural reference unless the context clearly dictates otherwise. Thus, for example, reference to “a cell” includes a plurality of such cells and equivalents thereof known to those skilled in the art. As well, the terms “a” (or “an”), “one or more” and “at least one” can be used interchangeably herein. It is also to be noted that the terms “comprising”, “including”, and “having” can be used interchangeably.

It will be understood that when an element is referred to as being “on”, “attached” to, “connected” to, “coupled” with, “contacting”, etc., another element, it can be directly on, attached to, connected to, coupled with or contacting the other element or intervening elements may also be present. In contrast, when an element is referred to as being, for example, “directly on”, “directly attached” to, “directly connected” to, “directly coupled” with or “directly contacting” another element, there are no intervening elements present. It will also be appreciated by those of skill in the art that references to a structure or feature that is disposed “adjacent” another feature may have portions that overlap or underlie the adjacent feature.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the invention.

Furthermore, relative terms, such as “lower” or “bottom” and “upper” or “top,” may be used herein to describe one element’s relationship to another element as illustrated in the figures. It will be understood that relative terms are intended to encompass different orientations of the device in addition to the orientation depicted in the figures. For example, if the device in one of the figures is turned over, elements described as being on the “lower” side of other elements would then be oriented on “upper” sides of the other elements. The exemplary term “lower”, can therefore, encompasses both an orientation of “lower” and “upper,” depending of the particular orientation of the figure. Similarly, if the device in one of the figures is turned over, elements described as “below” or “beneath” other elements would then be oriented “above” the other elements. The exemplary terms “below” or “beneath” can, therefore, encompass both an orientation of above and below.

It will be further understood that the terms “comprises” and/or “comprising”, or “includes” and/or “including”, or “has” and/or “having”, or “carry” and/or “carrying”, or “contain” and/or “containing”, or “involve” and/or “involving”, “characterized by”, and the like are to be open-ended, i.e., to mean including but not limited to. When used in this disclosure, they specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the invention, and will not be interpreted in an idealized or overly formal sense unless expressly so defined herein.

As used in the disclosure, “around”, “about”, “approximately” or “substantially” shall generally mean within 20 percent, preferably within 10 percent, and more preferably within 5 percent of a given value or range. Numerical quantities given herein are approximate, meaning that the term “around”, “about”, “approximately” or “substantially” can be inferred if not expressly stated.

As used in the disclosure, the phrase “at least one of A, B, and C” should be construed to mean a logical (A or B or C), using a non-exclusive logical OR. As used herein, the term “and/or” includes any and all combinations of one or more of the associated listed items.

As used in the disclosure, the term “target microRNA” or “target miRNA” refers to a microRNA sequence that is sought to be amplified and/or quantified. The target miRNA can be obtained from any source, and can comprise any number of different compositional components. The target microRNA can be a marker for a determining the condition of a subject. The condition can be a physiological or a mental condition. Further, it will be appreciated that “target miRNA” can refer to the target miRNA itself, as well as surrogates thereof, for example amplification products, and native sequences. The target miRNA of the present teachings can be derived from any of a number of sources, including without limitation, viruses, prokaryotes, eukaryotes, for example but not limited to plants, fungi, and animals. These sources may include, but are not limited to, whole blood, a tissue biopsy, lymph, bone marrow, amniotic fluid, hair, skin, semen, biowarfare agents, anal secretions, vaginal secretions, perspiration, saliva, buccal swabs, various environmental samples (for example, agricultural, water, and soil), research samples generally, purified samples generally, cultured cells, and lysed cells. It will be appreciated that target miRNA can be isolated from samples using any of a variety of procedures known in the art. In general, the target miRNA of the present teachings will be single stranded.

As used in the disclosure, the term “reverse transcription reaction” refers to an elongation reaction in which the 3' target-specific portion of a stem-loop primer is extended to form an extension reaction product comprising a strand complementary to the target miRNA. In some embodiments, the target miRNA is a miRNA molecule and the extension reaction is a reverse transcription reaction comprising a reverse transcriptase, where the 3' end of a stem-loop primer is extended. In some embodiments, the extension reaction is a reverse transcription reaction comprising a polymerase derived from a Eubacteria. In some embodiments, the extension reaction can comprise rTth polymerase, for example as commercially available from Applied Biosystems catalog number N808-0192, and N808-0098. In some embodiments, the target miRNA is a miRNA or other RNA molecule, and the use of polymerases that also comprise reverse transcription properties can allow for a first reverse transcription reaction followed thereafter by an amplification reaction such as a multiplexed PCR-based pre-amplification in the same reaction vessel, thereby allowing for the consolidation of two reactions in single reaction vessel. In some embodiments, the target miRNA is a DNA molecule and the extension reaction comprises a polymerase and results in the synthesis of a complementary strand of DNA. The term reverse transcription also includes also includes the synthesis of a DNA complement of a template DNA molecule. Similarly, a reverse transcription product can be a DNA molecule synthesized in a reverse transcription reaction, which is thus complementary to the template.

As used in the disclosure, the term “reverse transcription reaction” refers to an elongation reaction in which the 3' target-specific portion of a stem-loop primer is extended to form an extension reaction product comprising a strand complementary to the target miRNA. In some embodiments, the extension reaction is a reverse transcription reaction comprising a reverse transcriptase, where the 3' end of a stem-loop primer is extended. In some embodiments, the extension reaction is a reverse transcription reaction comprising a polymerase derived from a Eubacteria. In some embodiments, the extension reaction can comprise rTth polymerase. In some embodiments, the use of polymerases that also comprise reverse transcription properties can allow for a first reverse transcription reaction followed thereafter by an amplification reaction such as a multiplex fluorescent quantitative PCR in the same reaction vessel, thereby allowing for the consolidation of two reactions in single reaction vessel. A reverse transcription product can be a DNA molecule synthesized in a reverse transcription reaction, which is thus complementary to the target miRNA template.

As used in the disclosure, the term “hybridization” refers to the complementary base-pairing interaction of one nucleic acid with another nucleic acid that results in the formation of a duplex, triplex, or other higher-ordered structure, and is used herein interchangeably with “annealing.” Typically, the primary interaction is base specific, e.g., A/T and G/C, by Watson/Crick and Hoogsteen-type hydrogen bonding. Base-stacking and hydrophobic interactions can also contribute to duplex stability. Conditions for hybridizing primers to complementary and substantially complementary target sequences are well known, e.g., as described in Nucleic Acid Hybridization, A Practical Approach, B. Hames and S. Higgins, eds., IRL Press, Washington, D.C. (1985) and J. Wetmur and N. Davidson, Mol. Biol. 31:349 et seq. (1968). In general, whether such annealing takes place is influenced by, among other things, the length of the polynucleotides and the complementary, the pH, the temperature, the presence of mono- and divalent cations, the proportion of G and C nucleotides in the hybridizing region, the viscosity of the medium, and the presence of denaturants. Such variables influence the time required for hybridization. Thus, the preferred annealing conditions will depend upon the particular application. Such conditions, however, can be routinely determined by the person of ordinary skill in the art without undue experimentation. It will be appreciated that complementarity need not be perfect; there can be a small number of base pair mismatches that will minimally interfere with hybridization between the target sequence and the single stranded nucleic acids of the present teachings. However, if the number of base pair mismatches is so great that no hybridization can occur under minimally stringent conditions then the sequence is generally not a complementary target sequence. Thus, complementarity herein is meant that primers are sufficiently complementary to the target sequence to hybridize under the selected reaction conditions to achieve the ends of the present teachings.

As used in the disclosure, the term “amplifying” refers to any means by which at least a part of a target miRNA or its surrogate is reproduced, typically in a template-dependent manner, including without limitation, a broad range of techniques for amplifying nucleic acid sequences, either linearly or exponentially. In some embodiments, amplification can be achieved in a self-contained integrated approach comprising sample preparation and detection, as described for example in U.S. Pat. Nos. 6,153,425 and 6,649,378. Amplifying nucleic acids can employ reversibly modified enzymes, for example but not limited to those described in U.S. Pat. No. 5,773,258. The present teachings also contemplate various uracil-based decontamination strategies, wherein for example uracil can be incorporated into a amplification reaction, and subsequent carry-over products removed with various glycosylase treatments (see for example U.S. Pat. No. 5,536,649. Those in the art will understand that any protein with the desired enzymatic activity can be used in the disclosed methods and kits.

As used in the disclosure, the term “fluorescent quantitative PCR”, “quantitative PCR”, or “qPCR” refers to a PCR reaction performed in such a way and under such controlled conditions that the results of the assay are quantitative, that is, the assay is capable of quantifying the amount or concentration of a nucleic acid ligand present in the test sample. qPCR is a technique based on the polymerase chain reaction, and is used to amplify and simultaneously quantify a targeted nucleic acid molecule. qPCR allows for both detection and quantification (as absolute number of copies or relative amount when normalized to DNA input or additional normalizing genes) of a specific sequence in a DNA sample. In some embodiments, the DNA sample is a products containing cDNA produced from reverse transcription of a RNA sample, e.g. miRNA. The procedure follows the general principle of PCR, with the additional feature that the amplified DNA is quantified as it accumulates in the reaction in real time after each amplification cycle. qPCR is described, for example, in Kurnit et al. (U.S. Pat. No. 6,033,854), Wang et al. (U.S. Pat. Nos. 5,567,583 and 5,348,853), Ma et al. (The Journal of American Science, 2 (3), (2006)), Heid et al. (Genome Research 986-994, (1996)), Sambrook and Russell (Quantitative PCR, Cold Spring Harbor Protocols, (2006)), and Higuchi (U.S. Pat. Nos. 6,171,785 and 5,994,056). The contents of these are incorporated by reference herein in their entirety.

As used in the disclosure, the term "detection" refers to any of a variety of ways of determining the presence and/or quantity and/or identity of a target miRNA. In some embodiments employing a donor moiety and signal moiety, one may use certain energy-transfer fluorescent dyes. Certain non-limiting exemplary pairs of donors (donor moieties) and acceptors (signal moieties) are illustrated, e.g., in U.S. Pat. Nos. 5,863,727; 5,800,996; and 5,945,526. Use of some combinations of a donor and an acceptor have been called FRET (Fluorescent Resonance Energy Transfer). In some embodiments, fluorophores that can be used as signaling probes include, but are not limited to, rhodamine, cyanine 3 (Cy 3), cyanine 5 (Cy 5), fluorescein, Vic®, LiZ™, Tamra™, 5-Fam™, 6-Fam™, and Texas Red (Molecular Probes). (Vic®, Liz™, Tamra™, 5-Fam™, and 6-Fam™. In some embodiments, the amount of probe that gives a fluorescent signal in response to an excited light typically relates to the amount of nucleic acid produced in the amplification reaction. Thus, in some embodiments, the amount of fluorescent signal is related to the amount of product created in the amplification reaction. In such embodiments, one can therefore measure the amount of amplification product by measuring the intensity of the fluorescent signal from the fluorescent indicator. According to some embodiments, one can employ an internal standard to quantify the amplification product indicated by the fluorescent signal. See, e.g., U.S. Pat. No. 5,736,333. Devices have been developed that can perform a thermal cycling reaction with compositions containing a fluorescent indicator, emit a light beam of a specified wavelength, read the intensity of the fluorescent dye, and display the intensity of fluorescence after each cycle. Devices comprising a thermal cycler, light beam emitter, and a fluorescent signal detector, have been described, e.g., in U.S. Pat. Nos. 5,928,907; 6,015,674; and 6,174,670. In some embodiments, combined thermal cycling and fluorescence detecting devices can be used for precise quantification of target nucleic acid sequences in samples. In some embodiments, fluorescent signals can be detected and displayed during and/or after one or more thermal cycles, thus permitting monitoring of amplification products as the reactions occur in "real time." In some embodiments, one can use the amount of amplification product and number of amplification cycles to calculate how much of the target nucleic acid sequence was in the sample prior to amplification. In some embodiments, one could simply monitor the amount of amplification product after a predetermined number of cycles sufficient to indicate the presence of the target nucleic acid sequence in the sample. One skilled in the art can easily determine, for any given sample type, primer sequence, and reaction condition, how many cycles are sufficient to determine the presence of a given target miRNA. As used herein, determining the presence of a target can comprise identifying it, as well as optionally quantifying it. In some embodiments, the amplification products can be scored as positive or negative as soon as a given number of cycles is complete. In some embodiments, the results may be transmitted electronically directly to a database and tabulated. Thus, in some embodiments, large numbers of samples can be processed and analyzed with less time and labor when such a instrument is used. In some embodiments, different detector probes may distinguish between different target miRNAs. A non-limiting example of such a probe is a 5'-nuclease fluorescent probe, such as a TaqMan® probe molecule or MGB probe, wherein a fluorescent molecule is attached to a fluorescence-quenching molecule through an oligonucleotide link element. In some embodiments, the oligonucleotide link element of the 5'-nuclease fluorescent probe binds to a specific sequence of an identifying portion or its complement. In some embodiments, different 5'-nuclease fluorescent probes, each fluorescing at different wavelengths, can distinguish between different amplification products within the same amplification reaction. For example, in some embodiments, one could use two different 5'-nuclease fluorescent probes that fluoresce at two different wavelengths (WLA and WLB) and that are specific to two different regions of two different extension reaction products (A and B, respectively). Amplification product A is formed if target miRNA A is in the sample, and amplification product B is formed if target polynucleotide B is in the sample. After amplification, one can determine which specific target nucleic acid sequences are present in the sample based on the wavelength of signal detected and their intensity. Thus, if an appropriate detectable signal value of only wavelength WLA is detected, one would know that the sample includes target miRNA A, but not target miRNA B. If an appropriate detectable signal value of both wavelengths WLA and WLB are detected, one would know that the sample includes both target miRNA A and target miRNA B.

As used in the disclosure, the term "detector probe" or "probe" refers to a molecule used in an amplification reaction, typically for quantitative or real-time PCR analysis, as well as end-point analysis. Such probes can be used to monitor the amplification of products of reverse transcription of the target micro RNAs. In some embodiments, probes present in an amplification reaction are suitable for monitoring the amount of amplicon(s) produced as a function of time. Such detector probes include, but are not limited to, the 5'-exonuclease assay (TaqMan® probes described herein (see also U.S. Pat. No. 5,538,848) various stem-loop molecular beacons™ (see e.g., U.S. Pat. Nos. 6,103,476 and 5,925,517 and Tyagi and Kramer, 1996, Nature Biotechnology 14:303-308), stemless or linear beacons (see, e.g., WO 99/21881), PNA Molecular Beacons™ (see, e.g., U.S. Pat. Nos. 6,355,421 and 6,593,091), linear PNA beacons (see, e.g., Kubista et al., 2001, SPIE 4264:53-58), non-FRET probes (see, e.g., U.S. Pat. No. 6,150,097), Sunrise®/Amplifluor® probes (U.S. Pat. No. 6,548,250), stem-loop and duplex Scorpion™ probes (sequence-specific, bi-labeled fluorescent probe/primer hybrids designed for qPCR) (Solinas et al., 2001, Nucleic Acids Research 29: E96 and U.S. Pat. No. 6,589,743), bulge loop probes (U.S. Pat. No. 6,590,091), pseudo knot probes (U.S. Pat. No. 6,589,250), cyclicons (U.S. Pat. No. 6,383,752), MGB Eclipse™ probe (dual-labeled, fluorogenic probes used in qPCR assays, incorporating a reporter dye at the 5' end and an MGB-Eclipse quencher at the 3' end) (Epoch Biosciences), hairpin probes (U.S. Pat. No. 6,596,490), peptide nucleic acid (PNA) light-up probes, self-assembled nanoparticle probes, and ferrocene-modified probes described, for example, in U.S. Pat. No. 6,485,901; Mhlanga et al., 2001, Methods 25:463-471; Whitcombe et al., 1999, Nature Biotechnology. 17:804-807; Isacsson et al., 2000, Molecular Cell Probes. 14:321-328; Svanvik et al., 2000, Anal Biochem. 281:26-35; Wolffs et al., 2001, Biotechniques 766:769-771; Tsourkas et al., 2002, Nucleic Acids Research. 30:4208-4215; Riccelli et al., 2002, Nucleic Acids Research 30:4088-4093; Zhang et al., 2002 Shanghai. 34:329-332; Maxwell et al., 2002, J. Am. Chem. Soc. 124:9606-9612; Broude et al., 2002, Trends Biotechnol. 20:249-56; Huang et al., 2002, Chem Res. Toxicol. 15:118-126; and Yu et al., 2001, J. Am. Chem. Soc 14:11155-11161. Probes can also comprise quenchers, including without limitation black hole quenchers (Biosearch), Iowa Black (IDT), QSY quencher (Molecular Probes), and Dabsyl and Dabcel sulfonate/carboxylate Quenchers (Epoch). Probes can also comprise two probes, wherein for example a fluor is on one probe, and a quencher is on the other probe, wherein hybridization of the two probes together on a target quenches the signal, or wherein hybridization on the target alters the signal signature via a change in fluorescence. Probes can also comprise sulfonate derivatives of fluorescenin dyes with S03 instead of the carboxylate group, phosphoramidite forms of fluorescein, phosphoramidite forms of CY 5 (commercially available for example from Amersham). In some embodiments, intercalating labels are used such as ethidium bromide, SYBR& Green I( ) (Molecular Probes), and PicoGreene® (Molecular Probes), thereby allowing visualization in real-time, or end point, of an amplification product in the absence of a probe. In some embodiments, real-time visualization can comprise both an intercalating probe and a sequence-based detector probe can be employed. In some embodiments, the detector probe is at least partially quenched when not hybridized to a complementary sequence in the amplification reaction, and is at least partially unquenched when hybridized to a complementary sequence in the amplification reaction. In some embodiments, probes can further comprise various modifications such as a minor groove binder (see for example U.S. Pat. No. 6,486,308) to further provide desirable thermodynamic characteristics. In some embodiments, detector probes can correspond to the zip-code introduced by the stem-loop reverse transcription primer.

As used in the disclosure, the term "stem-loop primer" or "stem-loop reverse transcription primer" refers to a molecule comprising an anchor sequence on its 3'end and a stem-loop structure on its 5' end. The stem-loop structure comprises a stem portion and a loop portion. The term "anchor sequence" refers to the single stranded portion of a stem-loop primer that is complementary to a target miRNA. The anchor sequence is located downstream from the stem-loop structure of the stem-loop primer. Generally, the anchor sequence is between 3 and 12 nucleotides long. The term "stem" refers to the double stranded region of the stem-loop structure of the stem-loop primer that is between the anchor sequence and the loop, and is discussed more fully below. The term "loop" refers to a region of the stem-loop sequence that is located between the two complementary strands of the stem. Typically, the loop comprises single stranded nucleotides, though other moieties including modified RNA, Carbon spacers such as C18, and/or PEG (polyethylene glycol) are also possible. Generally, the loop is between 4 and 30 nucleotides long. In some embodiments, the loop is between 14 and 18 nucleotides long. In some embodiments, the loop is 16 nucleotides long. Those in the art will appreciate that loops shorter that 4 nucleotides and longer than 20 nucleotides can be identified in the course of routine methodology and without undue experimentation, and that such shorter and longer loops are contemplated by the present teachings.

As used in the disclosure, the term "Tm-enhancing tail" refers to a small number of nucleobases, typically between 3 and 10, that are included at the 5' end of the forward primer used in the qPCR reaction. The Tm-enhancing tail is not complementary to the reverse transcription product. In some embodiments, the Tm-enhancing tail is 4 bases. In some embodiments, the Tm-enhancing tail is 5 bases. In some embodiments, the Tm-enhancing tail is 6 bases. In some embodiments, the Tm-enhancing tail is 7 bases. Generally, longer Tm enhancing tails are possible, but will come at the cost of increased expense in oligonucleotide manufacturing, will further add to reaction complexity, and may raise the Tm to undesirable levels.

As used in the disclosure, "multiplex" refers to a reaction in which multiple targets DNA/RNA and/or targets in or from multiple samples are transcribed, amplified or quantified in the same reaction. In some embodiments of any of the aspects, a multiplex reverse transcription reaction can comprise reverse transcription of 1 to 100 target nucleotide sequences. As a nonlimiting example, a multiplex reverse transcription reaction can comprise reverse transcription of about 1 sample, about 2 samples, about 3 samples, about 4 samples, about 5 samples, about 6 samples, about 7 samples, about 8 samples, about 9 samples, about 10 samples, about 20 samples, about 30 samples, about 40 samples, about 50 samples, about 60 samples, about 70 samples, about 80 samples, about 90 samples, about 100 samples. "singleplex" refers to a reaction in which only one target DNA/RNA is transcribed, amplified or quantified in the same reaction.

As used in the disclosure, a "fragment" or "portion" of a nucleotide sequence refers to a nucleotide sequence of reduced length relative (e.g., reduced by 1, 2, 3, 4, 5, 6, 7, 8, 9, 10, 11, 12, 13, 14, 15, 16, 17, 18, 19, 20 or more nucleotides) to a reference nucleic acid or nucleotide sequence and comprising, consisting essentially of and/or consisting of a nucleotide sequence of contiguous nucleotides identical or almost identical (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 990/identical) to the reference nucleic acid or nucleotide sequence. Such a nucleic acid fragment or portion according to the invention may be, where appropriate, included in a larger polynucleotide of which it is a constituent. Thus, hybridizing to (or hybridizes to, and other grammatical variations thereof), for example, at least a portion of a target miRNA or cDNA, refers to hybridization to a nucleotide sequence that is identical or substantially identical to a length of contiguous nucleotides of the target miRNA or cDNA.

As used in the disclosure, a "heterologous" or a "recombinant" nucleotide sequence is a nucleotide sequence not naturally associated with a host cell into which it is introduced, including non-naturally occurring multiple copies of a naturally occurring nucleotide sequence. Different nucleic acids or proteins having homology are referred to herein as "homologues." The term homologue includes homologous sequences from the same and other species and orthologous sequences from the same and other species. "Homology" refers to the level of similarity between two or more nucleic acid and/or amino acid sequences in terms of percent of positional identity (i.e., sequence similarity or identity). Homology also refers to the concept of similar functional properties among different nucleic acids or proteins. Thus, the compositions and methods of the invention further comprise homologues to the nucleotide sequences and polypeptide sequences of this invention. "Orthologous," as used herein, refers to homologous nucleotide sequences and/or amino acid sequences in different species that arose from a common ancestral gene during speciation. A homologue of a nucleotide sequence of this invention has a substantial sequence identity (e.g., at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and/or 100%) to said nucleotide sequence of the invention.

As used in the disclosure, the term "percent sequence identity" or "percent identity" refers to the percentage of identical nucleotides in a linear polynucleotide sequence of a reference ("query") polynucleotide molecule (or its complementary strand) as compared to a test ("subject") polynucleotide molecule (or its complementary strand) when the two sequences are optimally aligned. In some embodiments, "percent identity" can refer to the percentage of identical amino acids in an amino acid sequence.

As used in the disclosure, the phrase "substantially identical," or "substantial identity" in the context of two nucleic acid molecules, nucleotide sequences or protein sequences, refers to two or more sequences or subsequences that have at least about 70%, 71%, 72%, 73%, 74%, 75%, 76%, 77%, 78%, 79%, 80%, 81%, 82%, 83%, 84%, 85%, 86%, 87%, 88%, 89%, 90°%, 91%, 92%, 93%, 94%, 95%, 96%, 97%, 98%, 99%, and/or 100% nucleotide or amino acid residue identity, when compared and aligned for maximum correspondence, as measured using one of the following sequence comparison algorithms or by visual inspection. In some embodiments of the invention, the substantial identity exists over a region of the sequences that is at least about 5 residues to about 150 residues in length. Thus, in some embodiments of the invention, the substantial identity exists over a region of the sequences that is at least about 3 to about 15 (e.g., 3, 4, 5, 6, 7, 8, 9, 10, 11, 12, 13, 14, 15 residues in length and the like or any value or any range therein), at least about 2 to about 30, at least about 5 to about 30, at least about 10 to about 30, at least about 16 to about 30, at least about 18 to at least about 25, at least about 18, at least about 22, at least about 25, at least about 30, at least about 40, at least about 50, about 60, about 70, about 80, about 90, about 100, about 110, about 120, about 130, about 140, about 150, or more residues in length, and any range therein. In representative embodiments, the sequences can be substantially identical over at least about 15 nucleotides. In some particular embodiments, the sequences are substantially identical over at least about 150 residues. In some embodiments, sequences of the invention can be about 70°% to about 100% identical over at least about 15 nucleotides to about 25 nucleotides. In some embodiments, sequences of the invention can be about 75% to about 100% identical over at least about 15 nucleotides to about 25 nucleotides. In further embodiments, sequences of the invention can be about 80% to about 100% identical over at least about 15 nucleotides to about 25 nucleotides. In further embodiments, sequences of the invention can be about 80% to about 100% identical over at least about 7 nucleotides to about 25 nucleotides. In some embodiments, sequences of the invention can be about 70% identical over at least about 15 nucleotides. In other embodiments, the sequences can be about 85% identical over about 22 nucleotides. In still other embodiments, the sequences can be 100% homologous over about 15 nucleotides. In a further embodiment, the sequences are substantially identical over the entire length of the coding regions. Furthermore, in representative embodiments, substantially identical nucleotide or protein sequences perform substantially the same function, e.g. reverse transcription.

For sequence comparison, typically one sequence acts as a reference sequence to which test sequences are compared. When using a sequence comparison algorithm, test and reference sequences are entered into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Optimal alignment of sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and optionally by computerized implementations of these algorithms such as GAP, BESTFIT, FASTA, and TFASTA available as part of the GCG Wisconsin Package® (Accelrys Inc., San Diego, Calif.). An "identity fraction" for aligned segments of a test sequence and a reference sequence is the number of identical components which are shared by the two aligned sequences divided by the total number of components in the reference sequence segment, i.e., the entire reference sequence or a smaller defined part of the reference sequence. Percent sequence identity is represented as the identity fraction multiplied by 100. The comparison of one or more polynucleotide sequences may be to a full-length polynucleotide sequence or a portion thereof, or to a longer polynucleotide sequence. For purposes of this invention "percent identity" may also be determined using BLASTX version 2.0 for translated nucleotide sequences and BLASTN version 2.0 for polynucleotide sequences.

Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., 1990). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues: always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89:10915 (1989)).

In addition to calculating percent sequence identity, the BLAST algorithm also performs a statistical analysis of the similarity between two sequences (see, e.g., Karlin & Altschul, *Proc. Nat'l. Acad Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleotide sequence to the reference nucleotide sequence is less than about 0.1 to less than about 0.001. Thus, in some embodiments of the invention, the smallest sum probability in a comparison of the test nucleotide sequence to the reference nucleotide sequence is less than about 0.001.

Two nucleotide sequences can also be considered to be substantially complementary when the two sequences hybridize to each other under stringent conditions. In some representative embodiments, two nucleotide sequences considered to be substantially complementary hybridize to each other under highly stringent conditions.

"Stringent hybridization conditions" and "stringent hybridization wash conditions" in the context of nucleic acid hybridization experiments such as Southern and Northern hybridizations are sequence dependent, and are different under different environmental parameters. An extensive guide to the hybridization of nucleic acids is found in Tijssen *Laboratory Techniques in Biochemistry and Molecular Biology—Hybridization with Nucleic Acid Probes* part I chapter 2 "Overview of principles of hybridization and the strategy of nucleic acid probe assays" Elsevier, New York (1993). Generally, highly stringent hybridization and wash conditions are selected to be about 5° C. lower than the thermal melting point ($T_m$) for the specific sequence at a defined ionic strength and pH.

The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleotide sequences which have more than 100 complementary residues on a filter in a Southern or northern blot is 50% formamide with 1 mg of heparin at 42° C., with the hybridization being carried out overnight. An example of highly stringent wash conditions is 0.1 5M NaCl at 72° C. for about 15 minutes. An example of stringent wash conditions is a 0.2×SSC wash at 65° C. for 15 minutes (see. Sambrook, infra, for a description of SSC buffer). Often, a high stringency wash is preceded by a low stringency wash to remove background probe signal. An example of a medium stringency wash for a duplex of, e.g., more than 100 nucleotides, is 1×SSC at 45° C. for 15 minutes. An example of a low stringency wash for a duplex of, e.g., more than 100 nucleotides, is 4-6×SSC at 40° C. for 15 minutes. For short probes (e.g., about 10 to 50 nucleotides), stringent conditions typically involve salt concentrations of less than about 1.0 M Na ion, typically about 0.01 to 1.0 M Na ion concentration (or other salts) at pH 7.0 to 8.3, and the temperature is typically at least about 30° C. Stringent conditions can also be achieved with the addition of destabilizing agents such as formamide. In general, a signal to noise ratio of 2× (or higher) than that observed for an unrelated probe in the particular hybridization assay indicates detection of a specific hybridization. Nucleotide sequences that do not hybridize to each other under stringent conditions are still substantially identical if the proteins that they encode are substantially identical. This can occur, for example, when a copy of a nucleotide sequence is created using the maximum codon degeneracy permitted by the genetic code.

In view of the shortcomings in prior art, namely, reverse transcription-quantitative PCR (RT-qPCR) can only be performed to quantify the expression level of a single target miRNA, the present invention provides a method for screening a multiplex reverse transcription primer combination for quantifying multiple target miRNAs. Thus, the present invention enables simultaneously quantifying the multiple target miRNAs by the multiplex reverse transcription primer combination.

The multiplex reverse transcription primer combination of the present invention includes multiple stem-loop reverse transcription primers, and each of the stem-loop reverse transcription primer, from its 5' to 3' end, sequentially comprises a 5' end, a stem-loop sequence, an anchor base sequence, and a 3' end. The number of nucleotide bases in the stem-loop reverse transcription primer used is generally between 40 and 65, with a double-stranded region formed in the stem-loop sequence by a pair of fragments complimentary to each other. This double stranded region is the "stem", and typically has 11-14 paired nucleotide bases. The unpaired region, located between the pair of complimentary fragments, that cannot form a double-stranded structure protrudes to form a "loop," which is typically a sequence of 16-36 nucleotide bases. In one embodiment, the stem-loop reverse transcription primers with different stem-loop sequences are designed. In one embodiment, the stem-loop reverse transcription primers all have the same stem-loop sequence are designed.

The anchor sequence of the stem-loop reverse transcription primer locates downstream of the stem-loop sequence. The anchor sequence is complimentary to a 3' sequence of the target miRNA of which the stem-loop reverse transcription primer is designed for reverse transcription. The anchor sequence typically has a length between 3-12 nt. In one embodiment, the anchor sequence has a length between 4-11 nt. In one embodiment, the anchor sequence has a length between 4-8 nt. In one embodiment, the anchor sequence has a length between 6-11 nt. In one embodiment, the anchor sequence has a length between 6-8 nt.

The method for selecting one or more stem-loop reverse transcription primers to be used in a multiplex reverse transcription primer combination mainly includes the following steps: a) selecting a stem-loop sequence for each of the stem-loop reverse transcription primers; b) selecting a length of an anchor sequence of each of the stem-loop reverse transcription primers, and c) determining at least one combination of the stem-loop reverse transcription primers having multi-specificity and thus enables the multiplex RT-qPCR which quantifies the multiple target miRNAs simultaneously.

The present application discloses that, when the length of the anchor sequence is being used as a variable to screen each of the stem-loop reverse transcription primers for the multiplex RT, a combination of the stem-loop reverse transcription primers capable of being used for the multiplex RT-qPCR can be screened out. When this stem-loop reverse transcription primer combination is used for the multiplex RT of the multiple target miRNAs, there will be no cross-reaction, and thus it will exhibit multi-specificity for the subsequent multiplex qPCR. Thus, when the multiple target miRNAs are reversely transcribed in the multiplex RT using the combination of the stem-loop reverse transcription primers, the efficiency of detection/quantification is greatly improved, the operation process is simplified, and the cost of detection is reduced.

To quantify the multiple target miRNAs by the multiplex RT-qPCR, the stem-loop reverse transcription primer combination for the multiplex RT can be screened using the above screening method. Therefrom, a miRNA sample having the multiple targets miRNAs undergoes the multiplex RT using the screened stem-loop reverse transcription primer combination, before its reverse transcription products undergo the multiplex qPCR.

During the multiplex qPCR, a combination of forward primers, a universal or a combination of reverse primers, and a combination of probes are added to the reverse transcription products for amplification during the multiplex qPCR.

The principles for designing forward primers used in the qPCR are described as follows. In particular, the 5' end to 3' end of the forward primer is: 5'-$T_m$-enhancing tail-specific complimentary sequence-3', where the $T_m$-enhancing tail comprises randomly arranged A, T, C, or G to increase the $T_m$ value of the forward primer. The GC content of the forward primer is generally between 50% to 60%, and the 3' end of primer should avoid having three or more consecutive G or C bases. The length of the $T_m$-enhancing tail of the forward primer should be selected to ensure that the difference between the $T_m$ value of the forward primer and the universal reverse primer should be within 1° C., and both of the $T_m$ values of the forward and universal reverse primer should be around 55-60° C.

Principles for designing reverse primers used in the qPCR are described as follows. In particular, the length of the reverse primer is generally about 15-25 nt, with a $T_m$ value of 55-60° C. and a GC content of 50%-60%. The 3' end of the primer should avoid having three or more consecutive G or C bases, and the $T_m$ value of the forward and reverse primers should be within 1° C. of each other. To increase amplification efficiency, the reverse primer should be designed as close as possible to the loop of the stem-loop structure.

Principles for designing probes used in the qPCR are described as follows. In one embodiment, Taqman® probes are used as probes in the qPCR reaction. The length of each probe generally ranges from 25 to 32 nt, and the $T_m$ value is between 65-75° C., which is 5-10° C. higher than that of the forward/reverse primers. The GC content is 30-80%. The first base at the 5' end of each probe cannot be G, and should be as close as possible to the 3' end of the target miRNA sequence. The 5' end of the probe is labeled with a fluorescent reporter group, and the 3' terminal is labeled with a quencher group. The fluorescent reporter group may be selected from fluorescent reporter groups such as FAM™, VIC®, CY5® or ROX™.

Figure 1B:
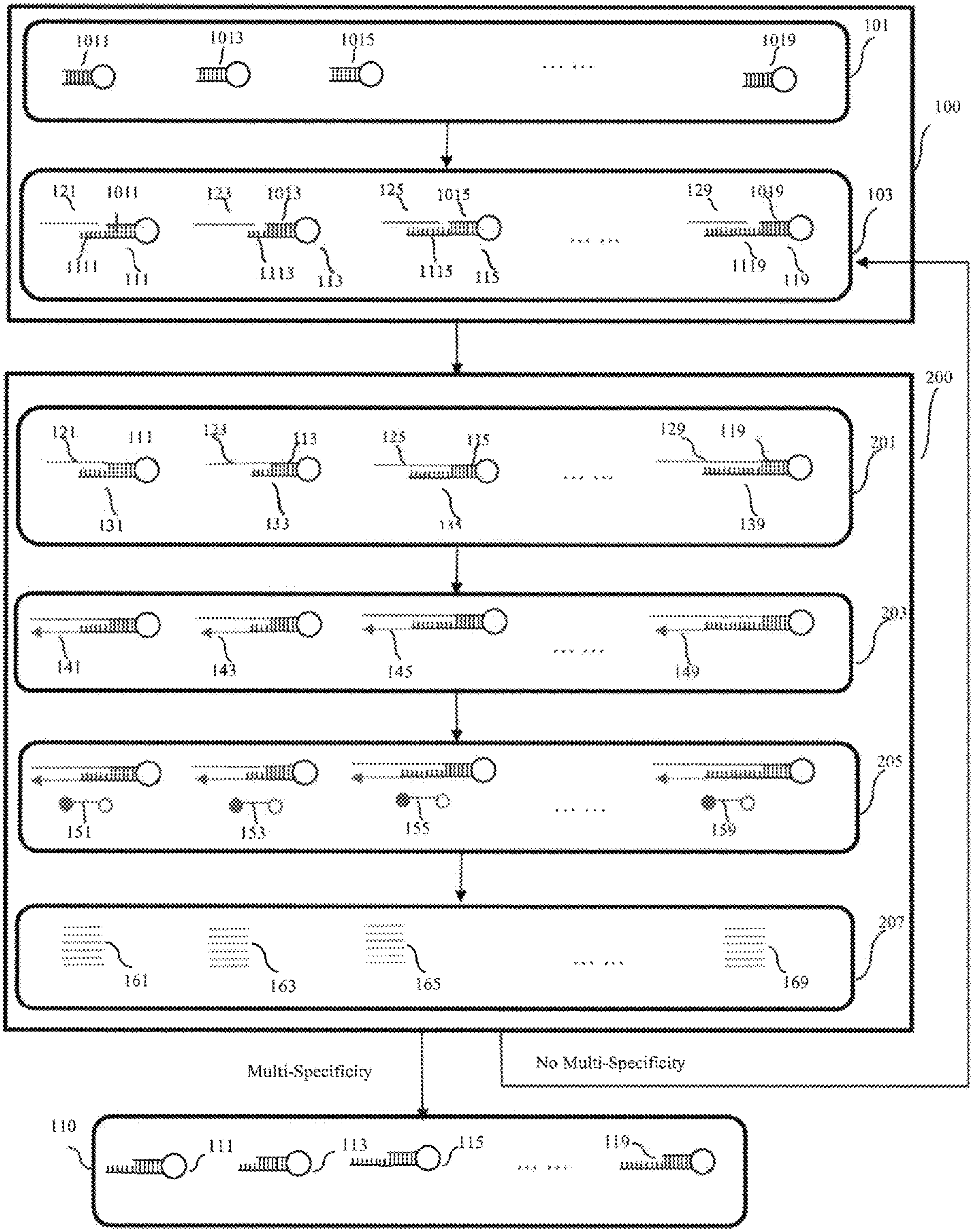

FIGS. 1A-B show diagrams of the method for screening a multiplex stem-loop reverse transcription primer combination 110 demonstrating the multi-specificity for quantifying the multiple target miRNAs simultaneously, the method comprising a selection process, a screening process, and optionally a repeat process. In particular, FIG. 1A shows a diagram of the method for screening a multiplex stem-loop reverse transcription primer combination 110 having four stem-loop reverse transcription primers. FIG. 1B shows a diagram of the method for screening a multiplex stem-loop reverse transcription primer combination 110 having multiple stem-loop reverse transcription primers. The screened multiplex stem-loop reverse transcription primer combination is capable of simultaneously quantifying the multiple target miRNAs.

In one embodiment, the number of the stem-loop reverse transcription primers are chosen according to the number of the target miRNAs to be quantified. In one embodiment, the combination has two stem-loop reverse transcription primers. In one embodiment, the combination has three stem-loop reverse transcription primers. In one embodiment, the combination has four stem-loop reverse transcription primers. In one embodiment, the combination has five stem-loop reverse transcription primers. In one embodiment, the combination has six stem-loop reverse transcription primers. In one embodiment, the combination has seven stem-loop reverse transcription primers. In one embodiment, the combination has eight stem-loop reverse transcription primers. In one embodiment, the combination has nine stem-loop reverse transcription primers. In one embodiment, the combination has ten stem-loop reverse transcription primers.

It should be noted that, despite the number of the stem-loop reverse transcription primers in the combination, the method for screening the combination(s) having multi-specificity is the same. Once a combination of the stem-loop reverse transcription primers demonstrates the multi-specificity, it is confirmed that any sub-combination of the screened combination having any number of the screened stem-loop reverse transcription primers in the screened combination has the multi-specificity as well.

In one embodiment, the selection process 100 starts with selecting the stem-loop reverse transcription primer combination 110 having more than one stem-loop reverse transcription primers 111/113/115/117. Each of the stem-loop reverse transcription primers 111/113/115/117 has a stem-loop sequence 1011/1013/1015/1017 forming a stem-loop structure and an anchor sequence 1111/1113/1115/1117 which is complimentary to a 3' sequence of one of the target miRNAs 121/123/125/127.

In one embodiment, the 3' sequence of each of the target miRNAs 121/123/125/127 is different from the 3' sequences of the other target miRNAs. In one embodiment, when the term "unique" is used for the 3' sequence of each of the target miRNAs, it represents that the 3' sequence of each of the target miRNAs is different from the 3' sequences of the other target miRNAs by at least 1 nt.

In selecting each of the stem-loop reverse transcription primers 111/113/115/117, one first selects a stem-loop sequence 1011/1013/1015/1017 for each of the stem-loop reverse transcription primers, and then selects a certain length for the anchor sequence of each of the stem-loop reverse transcription primers.

In one embodiment, a screening process is performed to test the multi-specificity of the selected stem-loop reverse transcription primer combination 110. The screening process starts with a step i) of separately performing a process of singleplex reverse transcription 201/203 using each of the stem-loop reverse transcription primers 111/113/115/117 with a mixed target miRNAs template comprising the multiple target miRNAs 121/123/125/127 to be quantified. The reverse transcription products 141/143/145/147 from each of the singleplex reverse transcription processes of the step i) are separately collected in the step ii).

Then, each collection of reverse transcription products 141/143/145/147 from the step ii) separately undergoes a multiplex qPCR 205/207 and each produces a collection of multiplex qPCR products 161/163/165/167. During the multiplex qPCR 205/207, a quantification result of each of the target miRNAs 121/123/125/127 is obtained and therefore forming a collection of the quantification results of the multiple target miRNAs.

The multi-specificity of the stem-loop reverse transcription primer combination 110 can be determined based on the collection of quantification results. In particular, when the collection of quantification results shows that each of the stem-loop reverse transcription primers 111/113/115/117 effectively and only reverse transcribes the target miRNA 111/113/115/117 to which its anchor sequence 1111/1113/1115/1117 is complimentary, the multi-specificity of the stem-loop reverse transcription primer combination 110 is confirmed.

However, when the selected stem-loop reverse transcription primer combination 110 fails to show the multi-specificity according to the quantification results 161/163/165/167, the stem-loop reverse transcription primer combination 110 is modified by a repeat process.

In particular, the repeat process starts with selecting a new length for the anchor sequence 1111/1113/1115/1117 of any of the stem-loop reverse transcription primers 111/113/115/117 which fails the multi-specificity test in the screening process. That is, the stem-loop reverse transcription primer reverse transcribes more than one target miRNAs, or fails to effectively reverse transcribe the target miRNA to which the anchor sequence of the stem-loop reverse transcription primer is complimentary.

In one embodiment, the length of the anchor sequence 1111/1113/1115/1117 is selected between 3 nt to 12 nt. In one embodiment, the length of the anchor sequence 1111/1113/1115/1117 is selected between 4 nt to 11 nt. In one embodiment, the length of the anchor sequence 1111/1113/1115/1117 is selected between 4 nt to 8 nt. In one embodiment, the length of the anchor sequence 1111/1113/1115/1117 is selected between 6 nt to 11 nt. In one embodiment, the length of the anchor sequence 1111/1113/1115/1117 is selected between 6 nt to 8 nt.

Once the new length for the anchor sequences 1111/1113/1115/1117 of the stem-loop reverse transcription primer 111/113/115/117 which fails the multi-specificity test is re-selected, a modified stem-loop reverse transcription primer combination is formed.

The next step of the repeat process is to repeat the screening process 200 with the modified stem-loop reverse transcription primer combination to determine the multi-specificity of the modified stem-loop reverse transcription primer combination.

The repeat process can generate one or more new modified stem-loop reverse transcription primer combinations by adjusting the length of the anchor sequence of any of the stem-loop reverse transcription primers. In one embodiment, the length of the anchor sequence of only one of the stem-loop reverse transcription primers is adjusted during one round of repeat process. In another embodiment, the lengths of the anchor sequences of more than one of the stem-loop reverse transcription primer are adjusted during one round of the repeat process.

The method stops once a combination of the stem-loop reverse transcription primers 110 is screened out and being confirmed for having the multi-specificity. In one embodiment, the multiplex RT-qPCR is then performed using the screened combination of the stem-loop reverse transcription primers 110 with the multiple target miRNAs 121/123/125/127. A comparison of singleplex RT separately with each of the stem-loop reverse transcription primers 111/113/115/117 and the multiplex RT with the combination 110 can be done to verify that the quantification results of the multiplex RT-qPCR are accurate.

In any of the singleplex RT processes, a hybridization reaction 201 and an extension reaction 203 are included. In the hybridization reaction 201, each of the selected stem-loop reverse transcription primer is separately hybridized to the target miRNA 121/123/125/127 to which its anchor sequence is complimentary, so as to form a collection of miRNA-stem-loop reverse transcription primer complex 131/133/135/137. In the following extension reaction 203, a cDNA 141/143/145/147 is formed by extending a 3' of the stem-loop reverse transcription primer 111/113/115/117 against the target miRNA 121/123/125/127.

Different from the singleplex RT processes, in any of the multiplex RT processes, the hybridization reaction 201 is conducted using more than one or all of the stem-loop reverse transcription primers, which are hybridized to the multiple target miRNAs. When the selected combination of the stem-loop reverse transcription primers 110 has the multi-specificity, each of the stem-loop reverse transcription primers only binds to the target miRNA to which its anchor sequence is complimentary.

The multiplex qPCR 205/207 of the screening process 200 uses a combination of forward primers, and a universal reverse primer or a combination of reverse primers. Each of the forward primers has a sequence complimentary to only one type of cDNA 141/143/145/147 or only one of the stem-loop reverse transcription primers being used for the reverse transcription.

A combination of probes 151/153/155/157 is also added to the reverse transcription to the reverse transcription products. In one embodiment, each of the probes is complimentary to only one type of cDNA 141/143/145/147, and each of the probes having a fluorescent reporter group different from the fluorescent reporter groups of the other probes. In one embodiment, the probes are Taqman® probes. In one embodiment, the probes are MGB probes.

Once the primers and the probes are added into the reverse transcription products, the multiplex qPCR amplifies the reverse transcription products. During the amplification process, the probes continue bind to the cDNAs produced, and a fluorescent light would be produced by the fluorescent reporter group of each of the probes whenever the cDNA extension forces each of the probes to leave a complimentary sequence of the cDNA and the fluorescent reporter group is no longer being suppressed by the quencher group. Each of the target mRNAs is quantified by the strength of the fluorescent light detected in each of the collections of multiplex qPCR products.

In one embodiment, the quantification result of each of the target miRNAs is a Ct value.

In one embodiment, the stem-loop sequences of at least two of the stem-loop reverse transcription primers are the same. In another embodiment, the stem-loop sequences of all the stem-loop reverse transcription primers are the same.

In one embodiment, once a combination of the stem-loop reverse transcription primers are screened out and its multi-specificity is confirmed, a sensitivity test of the combination of the stem-loop reverse transcription primers is conducted.

The sensitivity test is conducted using multiple templates of mixed target miRNAs 121/123/125/127 having a concentration gradient. That is, each of the templates of mixed target miRNAs has a concentration different from the other templates of mixed target miRNAs. In one embodiment, each of the templates of mixed target miRNAs is diluted to have a 10% concentration of the previous template. In one embodiment, each of the templates of mixed target miRNAs is diluted to have a 50% concentration of the previous template. In one embodiment, each of the templates of mixed target miRNAs is diluted to have a 20% concentration of the previous template.

Once the multiple templates of mixed target miRNAs 121/123/125/127 having a concentration gradient is prepared, the singleplex RT process is separately performed on each of the mixed miRNA templates using each of the stem-loop reverse transcription primers. That is, each of the stem-loop reverse transcription primers is separately used for singleplex reverse transcription of the multiple templates of mixed target miRNAs.

The reverse transcription products from each of the singleplex reverse transcription processes are collected. Multiplex qPCR are performed using each of the collections of reverse transcription products. A collection of quantification results of each of the target miRNAs in the multiple templates of mixed target miRNAs is obtained. Therefrom, for each of the stem-loop reverse transcription primers, its quantification results are arranged according to the concentration of the multiple templates of mixed target miRNAs, and the lowest concentration of the mixed target miRNAs template which is effectively transcribed by the stem-loop reverse transcription primer is considered as the result of the sensitivity test.

Each of the stem-loop reverse transcription primers has a stem-loop sequence forming a stem-loop structure and an anchor sequence complimentary to a 3' sequence of one of the multiple target miRNAs.

In one embodiment, the anchor sequence of at least one of the stem-loop reverse transcription primers has a length that is different from the lengths of the anchor sequences of the other stem-loop reverse transcription primers. In one embodiment, the each of the stem-loop reverse transcription primers has a length of about 40-65 nt.

In one embodiment, the stem-loop structures of some of the stem-loop reverse transcription primers are the same. In one embodiment, the stem-loop structures of all the stem-loop reverse transcription primers are the same. In one embodiment, the stem-loop structures of at least one of the stem-loop reverse transcription primers is different from the stem-loop structures of the other stem-loop reverse transcription primers. In one embodiment, each of the stem-loop structures is unique and different from the other stem-loop structures.

In one embodiment, a kit for simultaneously quantifying multiple target miRNAs is provided. The kit has a multiplex stem-loop reverse transcription primer combination having two to ten stem-loop reverse transcription primers, a combination of two to ten forward primers, wherein each of the forward primers comprises a $T_m$-enhancing tail and a forward primer sequence complimentary to the reverse transcription product produced in the RT, and a universal reverse primer or a combination of the reverse primers.

The kit also comprises a combination of probes. Each of the probe has a probe sequence same to a portion of sequence of one stem-loop reverse transcription primer. Each of the probe has a fluorescent reporter group, and a quencher group. Importantly, each of the probe has a fluorescent reporter group different from the fluorescent reporter agents of the other probes.

Example 1—Multiplex Stem-Loop Reverse Transcription Primers Quantifying miR-16-5p, miR-34c-5p, miR-9-3p, and miR-9-5p Below is an example of the screening method in this application screening a stem-loop reverse transcription primer combination for simultaneously detecting a combination multiple target miRNAs containing miR-16-5p, miR-34c-5p, miR-9-3p, and miR-9-5p. The sequences of these miRNAs are reported in the microRNA database (www.mirbase.org). Specifically, the sequence of miR-16-5p is SEQ ID No. 1, the sequence of miR-34c-5p is SEQ ID No. 2, the sequence of miR-9-3p is SEQ ID No. 3, and the sequence of miR-9-5p is SEQ ID No. 4.

Multiple stem-loop reverse transcription primers with different anchor sequence lengths are designed for the above target miRNAs combination. The length of each of the stem-loop reverse transcription primers is 40-60 nucleotides. Each of the stem-loop reverse transcription primers includes a stem-loop sequence and an anchor sequence. In the Example 1, the stem-loop sequence of each stem-loop reverse transcription primer is shown in Table 1, and the anchor sequence of each of the stem-loop reverse transcription primers is complementary to a 3' sequence of the target miRNA to be specifically detected by the stem-loop reverse transcription primer. In one embodiment, the length of the anchor sequence is selected within the range of 3-12 nt.

TABLE 1

Sequence of the stem-loop structure of each of the stem-loop reverse transcription primers in Example 1

| miRNA | Stem-loop structure | Sequence |
|---|---|---|
| miR-16-5p | Stem-loop structure 1 | SEQ ID No. 9 |
| miR-34c-5p | Stem-loop structure 2 | SEQ ID No. 10 |
| miR-9-3p | Stem-loop structure 3 | SEQ ID No. 11 |
| miR-9-5p | Stem-loop structure 4 | SEQ ID No. 12 |

Forward primers and reverse primers for the multiplex qPCR were designed for the reverse transcription products (cDNA), as shown in Table 2:

TABLE 2

Forward primers and reverse primers of the qPCR

| miRNA | Primer | Sequence |
|---|---|---|
| miR-16-5p | Forward primer | SEQ ID No. 17 |
| | Reverse primer | SEQ ID No. 25 |
| miR-34c-5p | Forward primer | SEQ ID No. 18 |
| | Reverse primer | SEQ ID No. 26 |
| miR-9-3p | Forward primer | SEQ ID No. 19 |
| | Reverse primer | SEQ ID No. 27 |
| miR-9-5p | Forward primer | SEQ ID No. 20 |
| | Reverse primer | SEQ ID No. 28 |

With respect to TaqMan® probes design, each of the probes is modified with different fluorescent groups (FAM™, VIC®, CY5®, ROX™, etc.), to distinguish the detection results of different target miRNAs based on the different fluorescent reporter groups, as shown in Table 3.

TABLE 3

Reporter and Quencher group of each of the probes.

| miRNA | Probe Name | Sequence | Reporter group | Quencher |
|---|---|---|---|---|
| miR-16-5p | miR-16-5p-P | SEQ ID No. 21 | VIC ® | BHQ1 |
| miR-34c-5p | miR-34c-5p-P | SEQ ID No. 22 | CY5 ® | BHQ3 |
| miR-9-3p | miR-9-3p-P | SEQ ID No. 23 | ROX ™ | BHQ2 |
| miR-9-5p | miR-9-5p-P | SEQ ID No. 24 | FAM ™ | BHQ1 |

Specificity for Each Stem-Loop Reverse Transcription Primer and Probe

Each stem-loop reverse transcription primer was separately subjected to a singleplex reverse transcription using a mixed target miRNAs template or ddH2O. Each of the stem-loop reverse transcription primers has an anchor sequence of 4, 6, 8, or 11 nt in length and a stem-loop sequences shown in Table 1. The singleplex reverse transcription system is shown in Table 4:

TABLE 4

| Reverse transcription system | |
|---|---|
| Reagent | 20 µL system |
| 10X RT MIX | 2 µL |
| HiScript II Enzyme Mix | 2 µL |
| Target miRNA template/water | 10 pg-1 µg |
| Stem-loop reverse transcription primer (2M) | 0.5 µL |
| $ddH_2O$ | To 20 µL |

The reverse transcription thermal cycle is shown in Table 5.

TABLE 5

| Thermal cycle for the reverse transcription | | |
|---|---|---|
| Cycle | Temperature | Time |
| 1 | 25° C. | 5 min |
| 1 | 50° C. | 15 min |
| 1 | 85° C. | 5 min |

The reverse transcription products collected from each of the singleplex reverse transcriptions undergo the multiplex qPCR, with the forward/reverse primers and probes shown in Tables 2 and 3. The qPCR system is shown in Table 6.

TABLE 6

| qPCR system | |
|---|---|
| Reagent | 20 µL system |
| Reverse transcription products | 2 µL |
| 2X Taq Pro HS U+Probe Master Mix | 10 µL |

TABLE 6-continued

| qPCR system | |
|---|---|
| Reagent | 20 µL system |
| TaqMan ® probe (10 µM) | 0.2 µL |
| Forward primer (10 µM) | 0.4 µL |
| Reverse primer (10 µM) | 0.4 µL |
| $ddH_2O$ | To 20 µL |

The qPCR amplification thermal cycles are shown in Table 7:

TABLE 7

| Thermal cycles for qPCR. | | |
|---|---|---|
| Cycle | Temperature | Time |
| 1X | 37° C. | 2 min |
| | 95° C. | 30 s |
| 45X | 95° C. | 10 s |
| | 60° C. | 30 s |

Figure 2A:
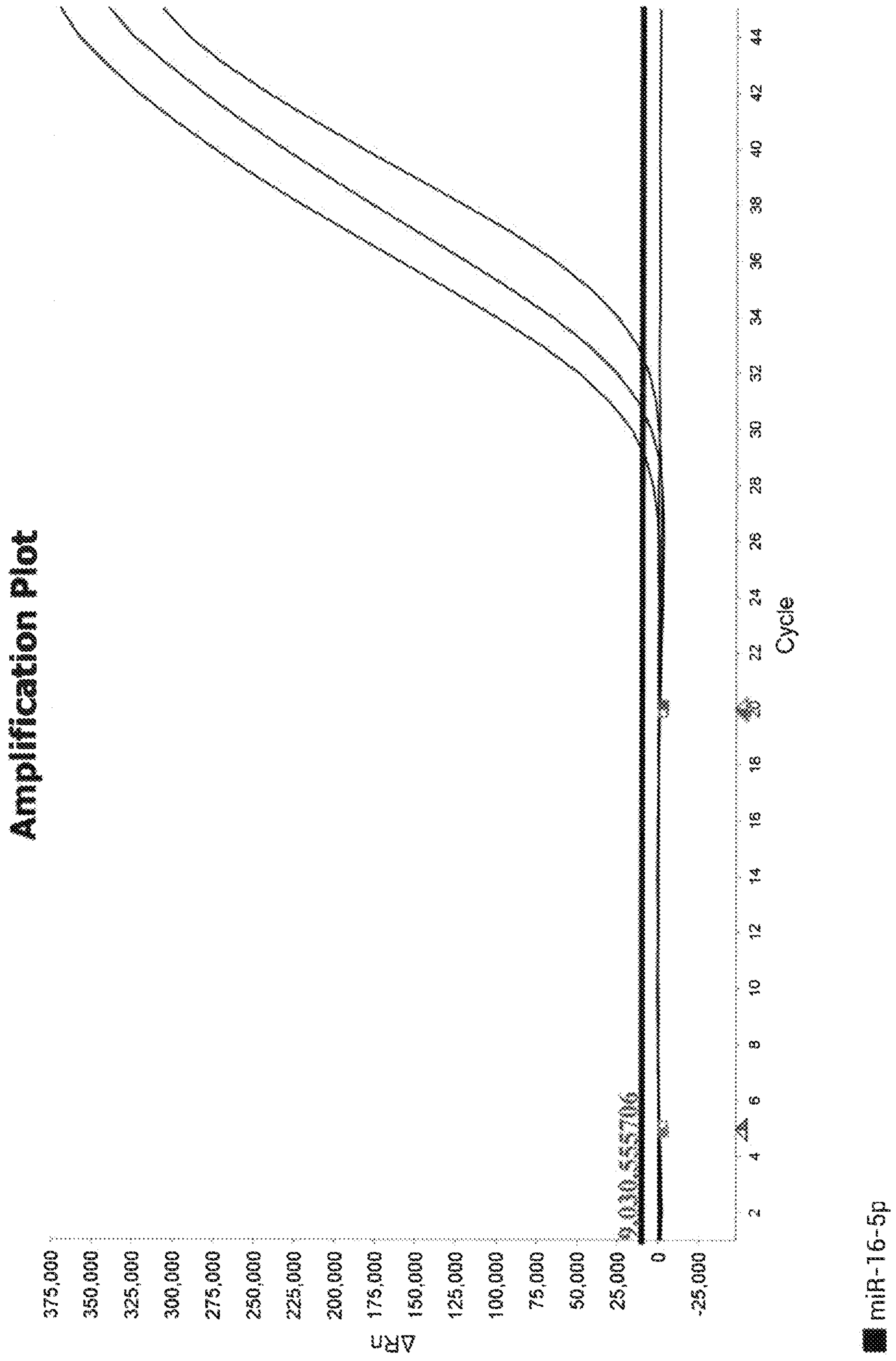
FIGS. 2A-D show amplification plots of singleplex RT-qPCR for each of the target miRNAs using each of the stem-loop reverse transcription primers with different anchor sequence lengths (6/8/11 nt).
Figure 2B:
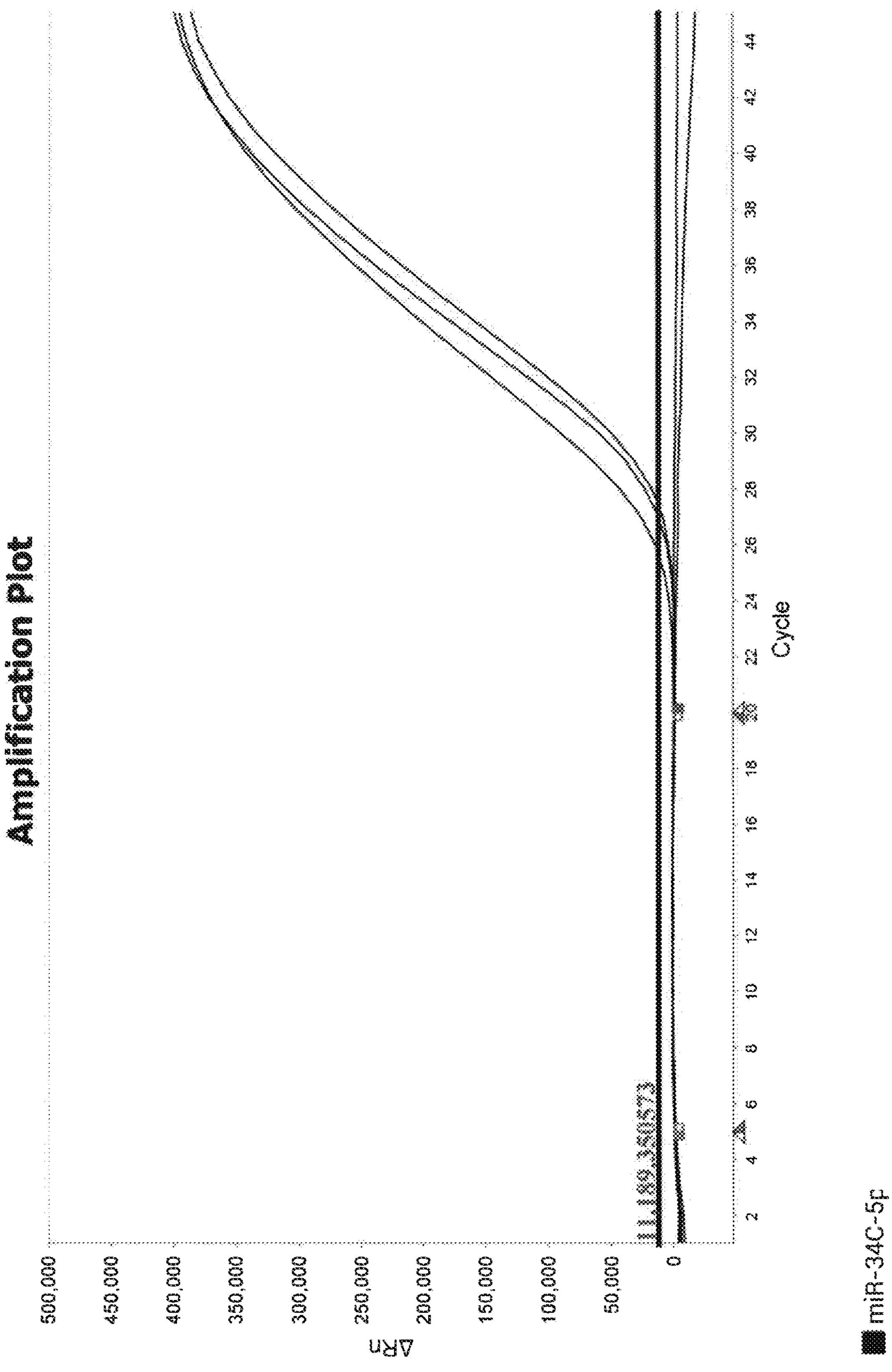
Figure 2C:
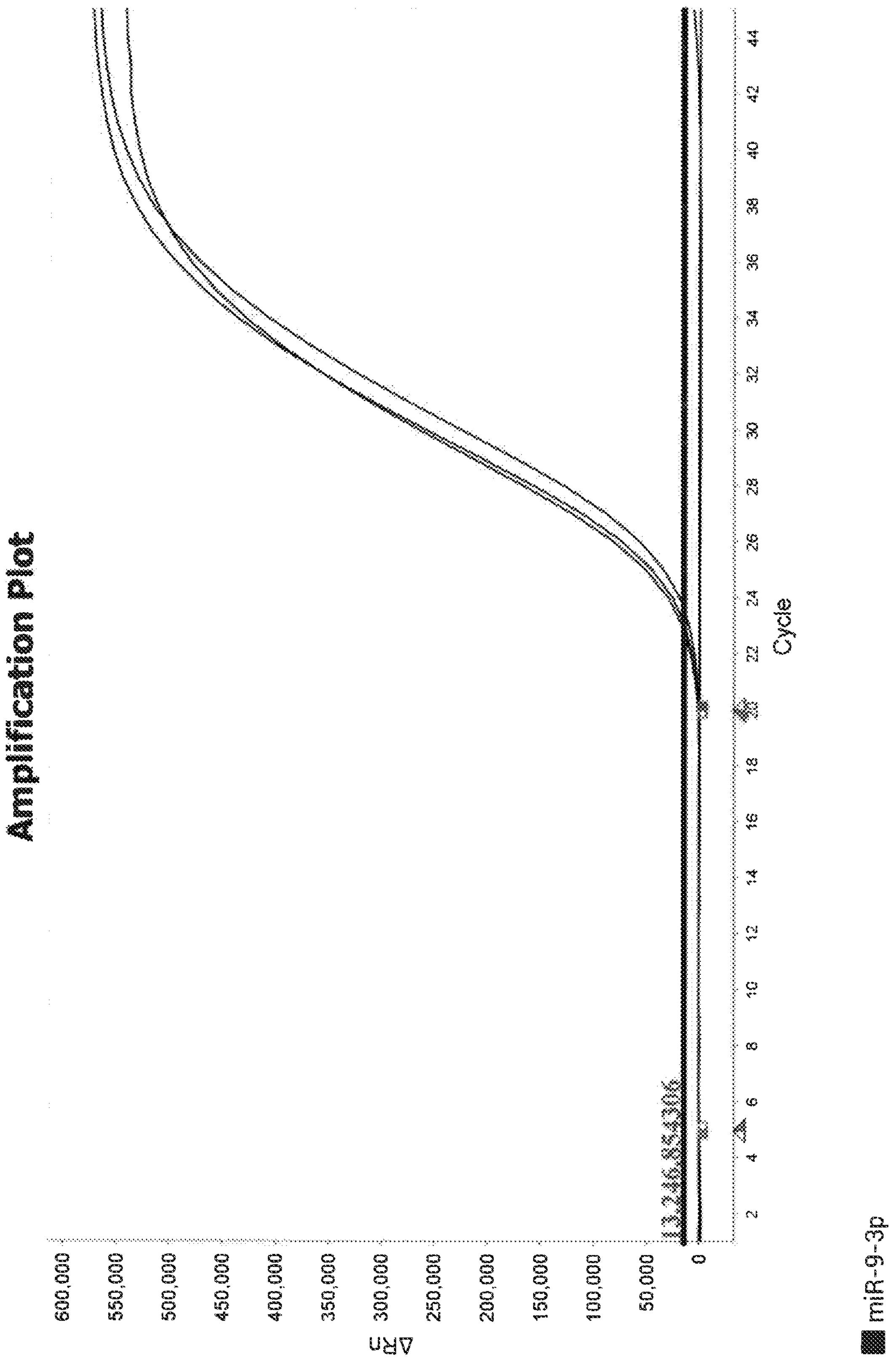
Figure 2D:
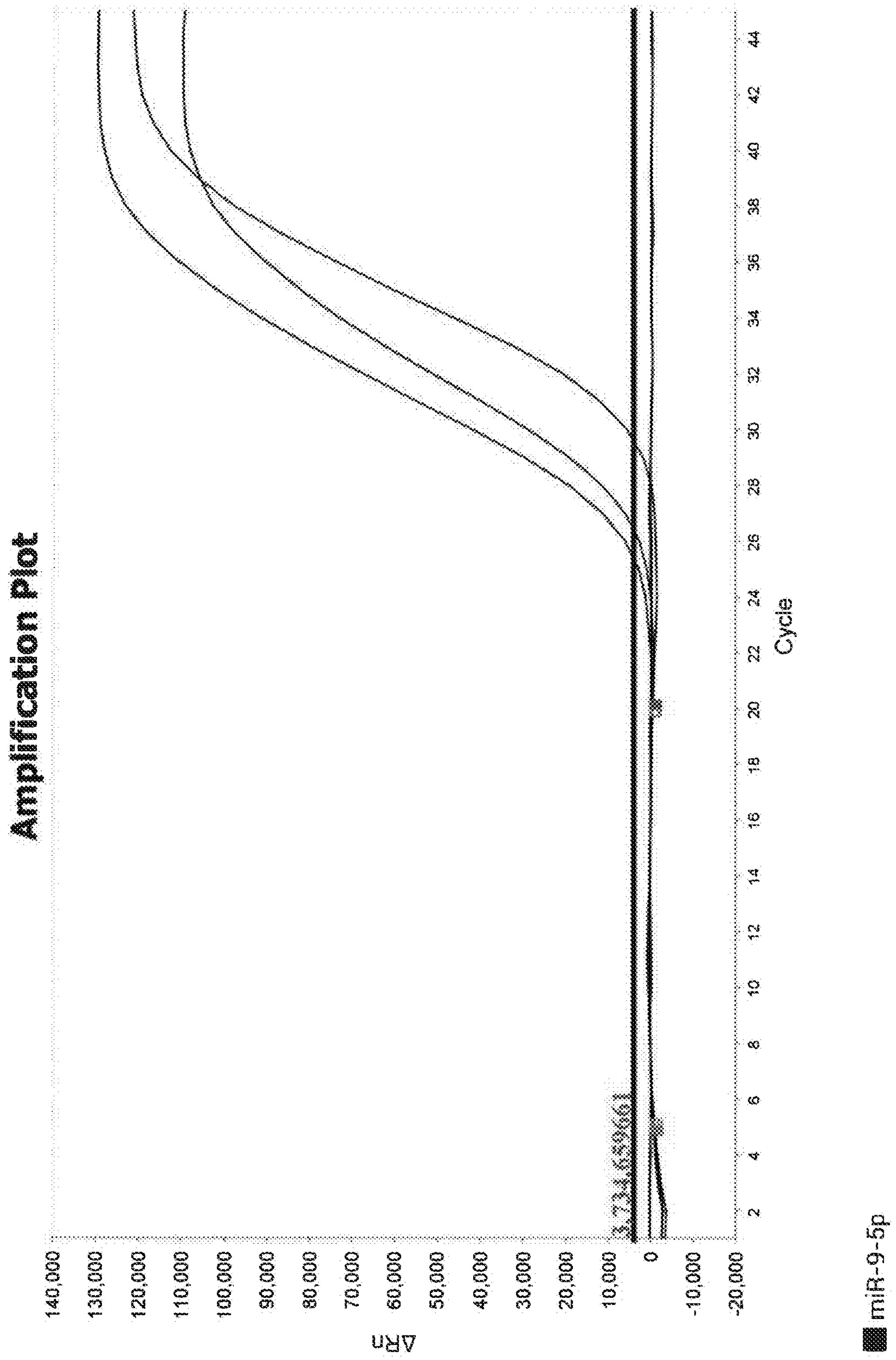
Figure 3A:
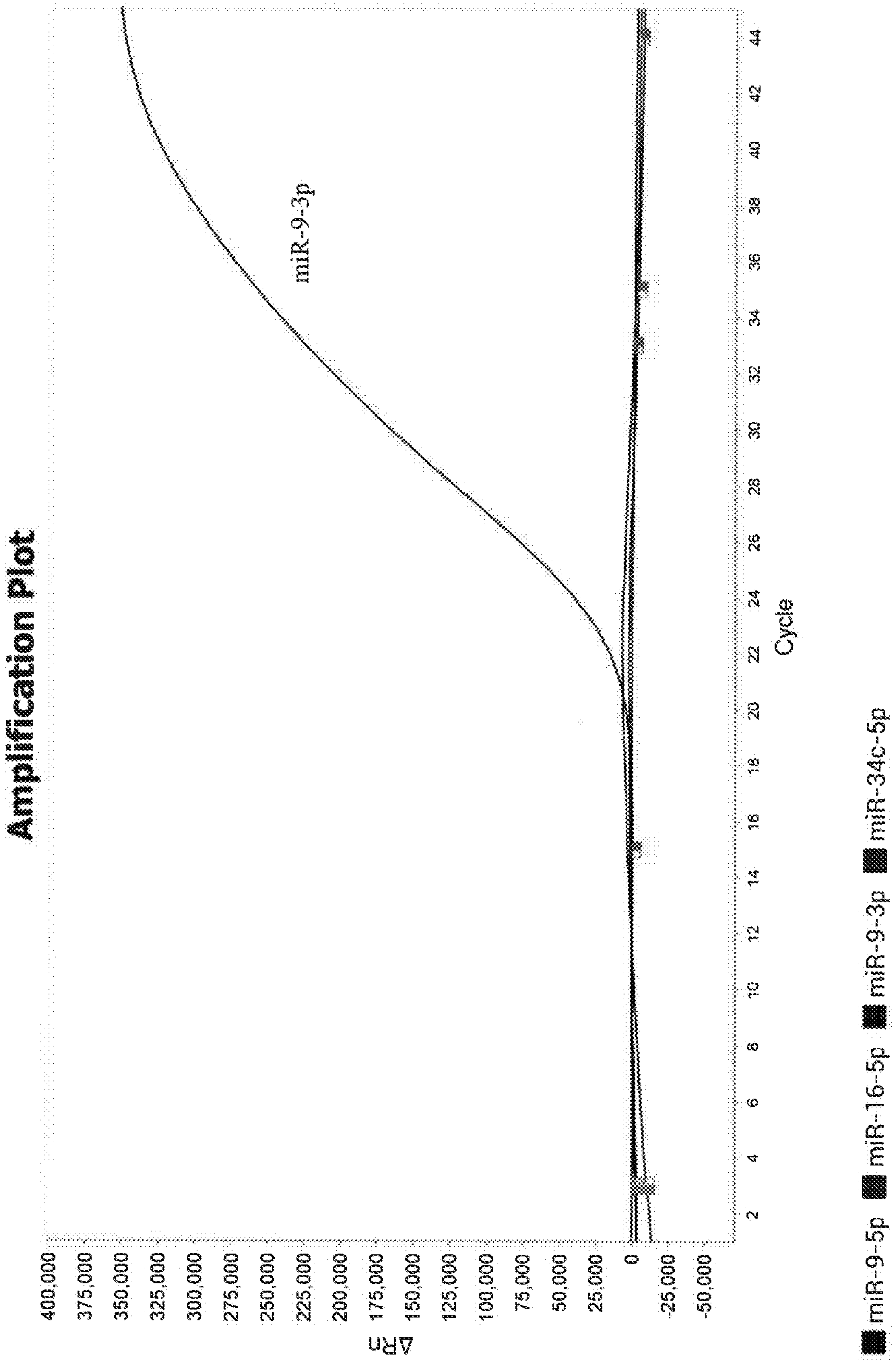
FIGS. 3A-E show amplification plots of singleplex reverse transcription using each of the screened stem-loop reverse transcription primers and a mixed miRNA templates having miR-9-3p, miR-34c-5p, miR-9-5p, and miR-16-5p, followed by multiplex-qPCR, as well as amplification plots of ddH$_2$O as the negative control, respectively.
Figure 3B:
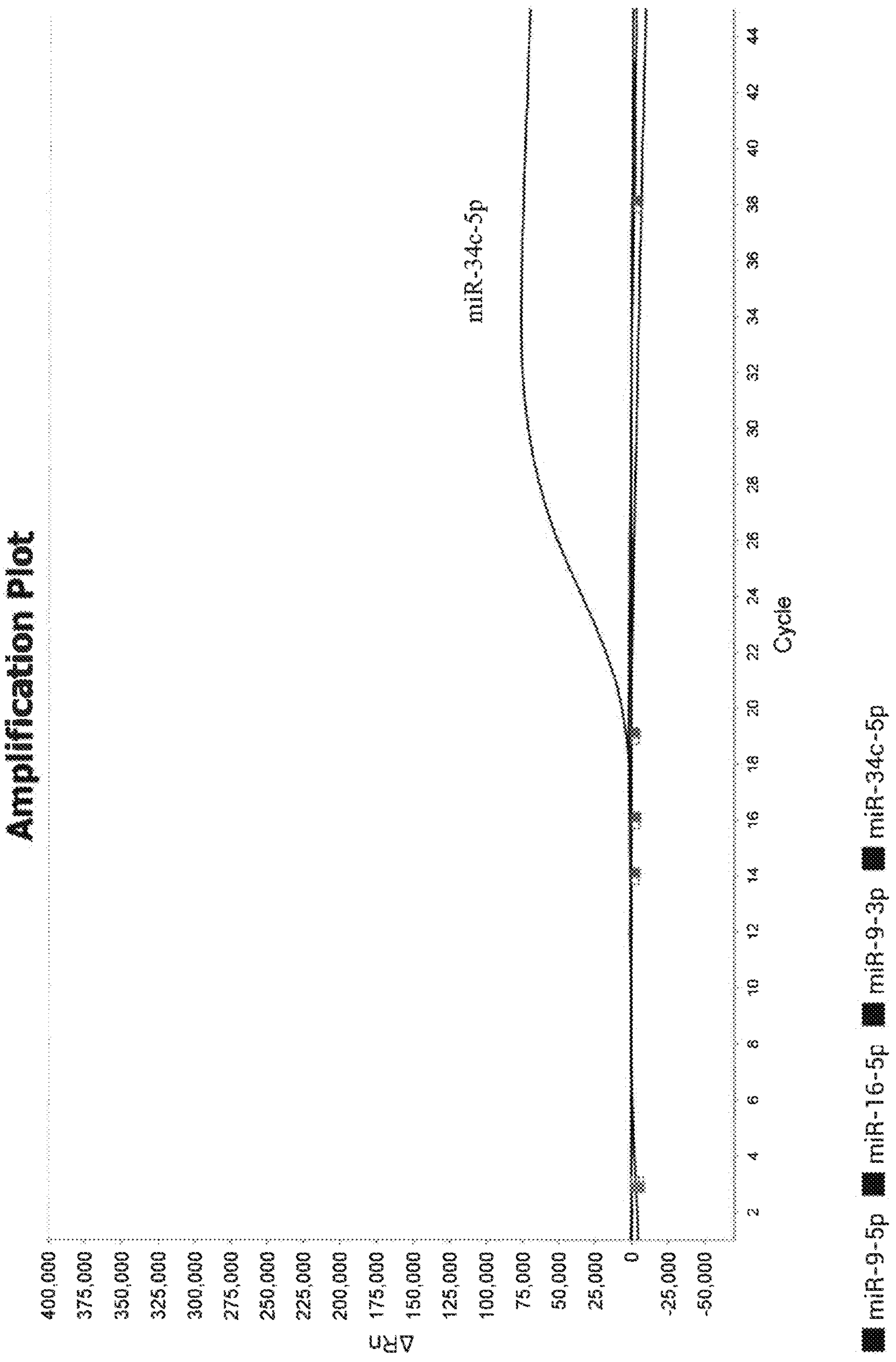
Figure 3C:
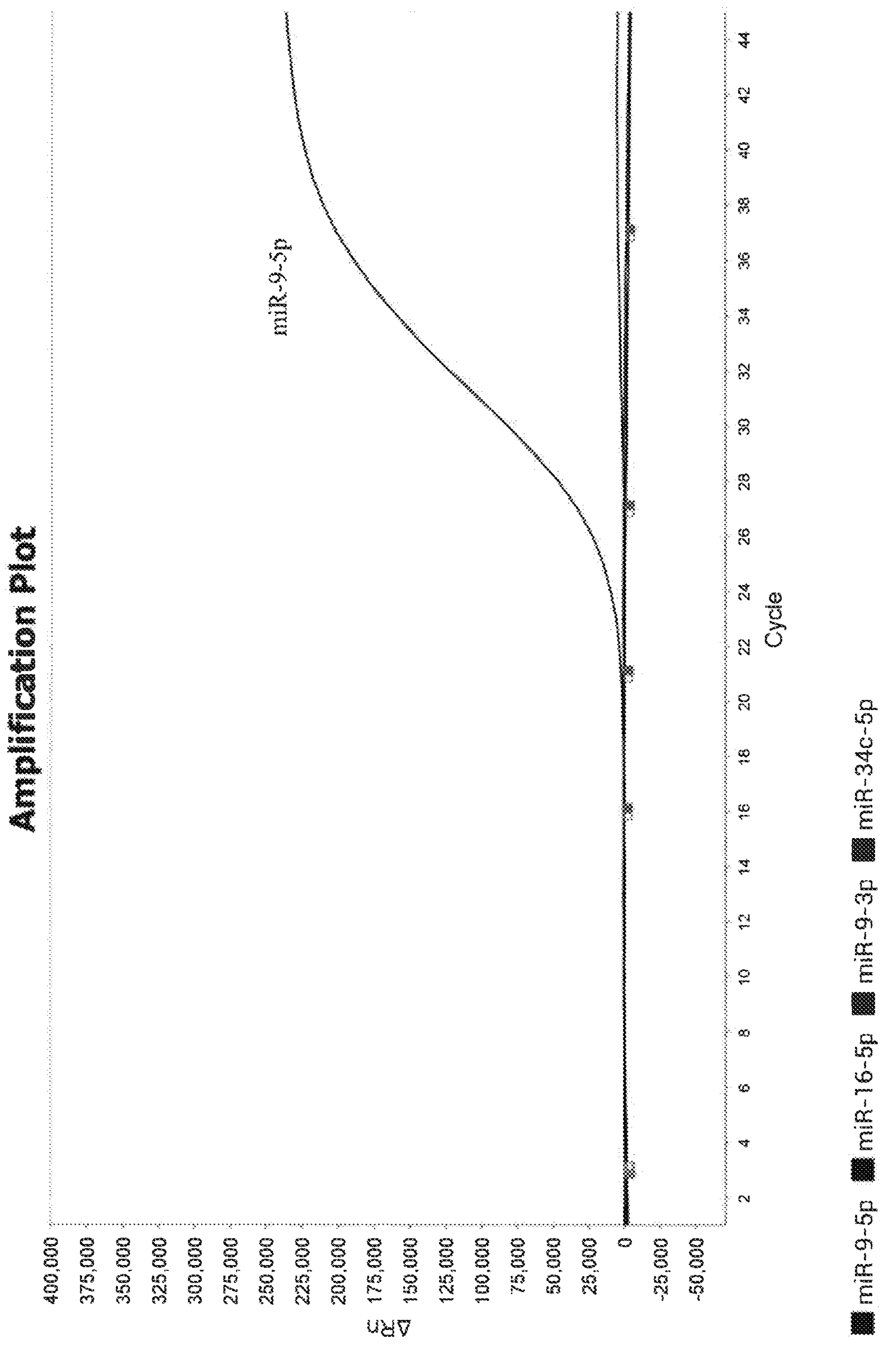
Figure 3D:
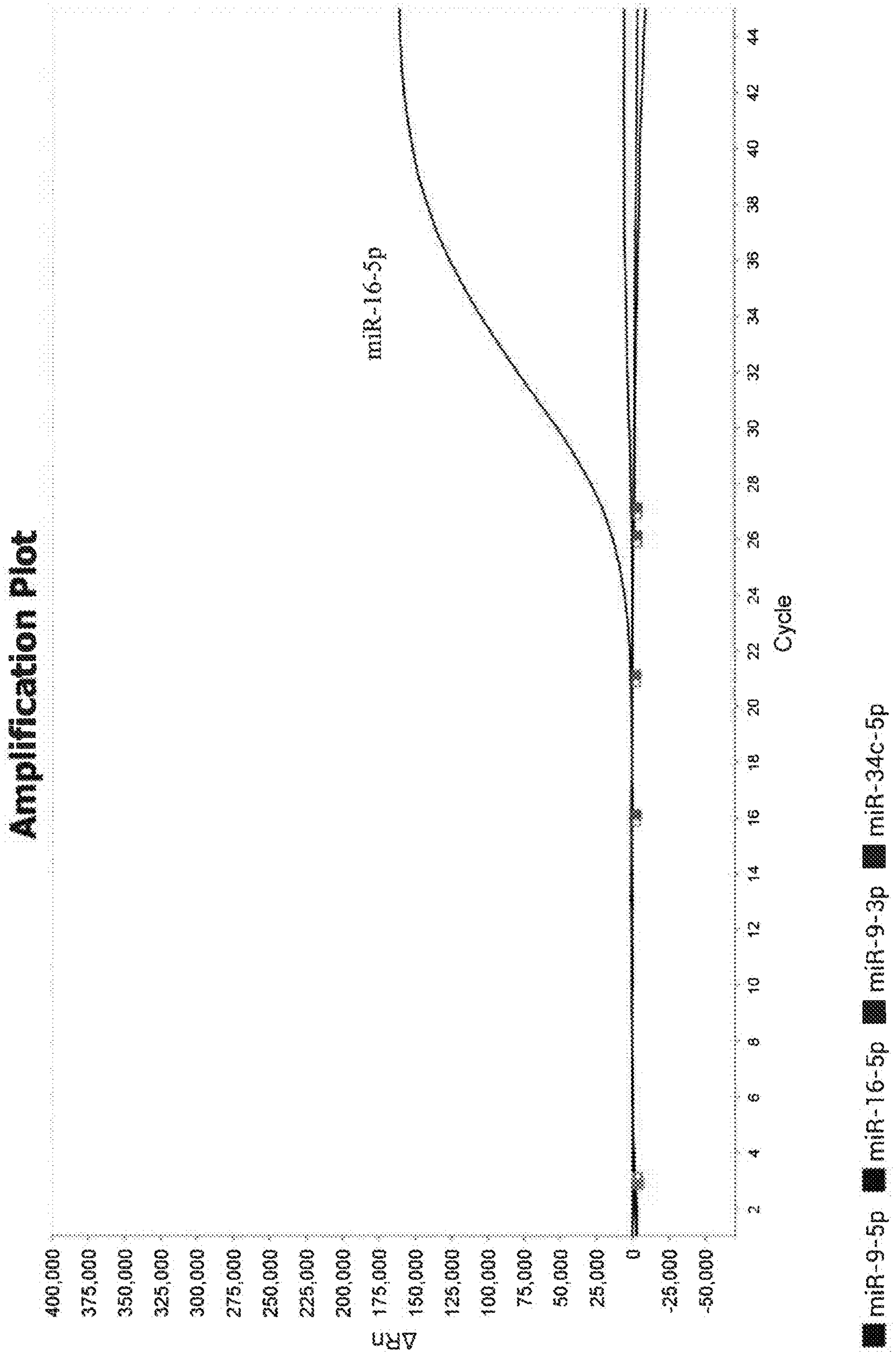
Figure 3E:
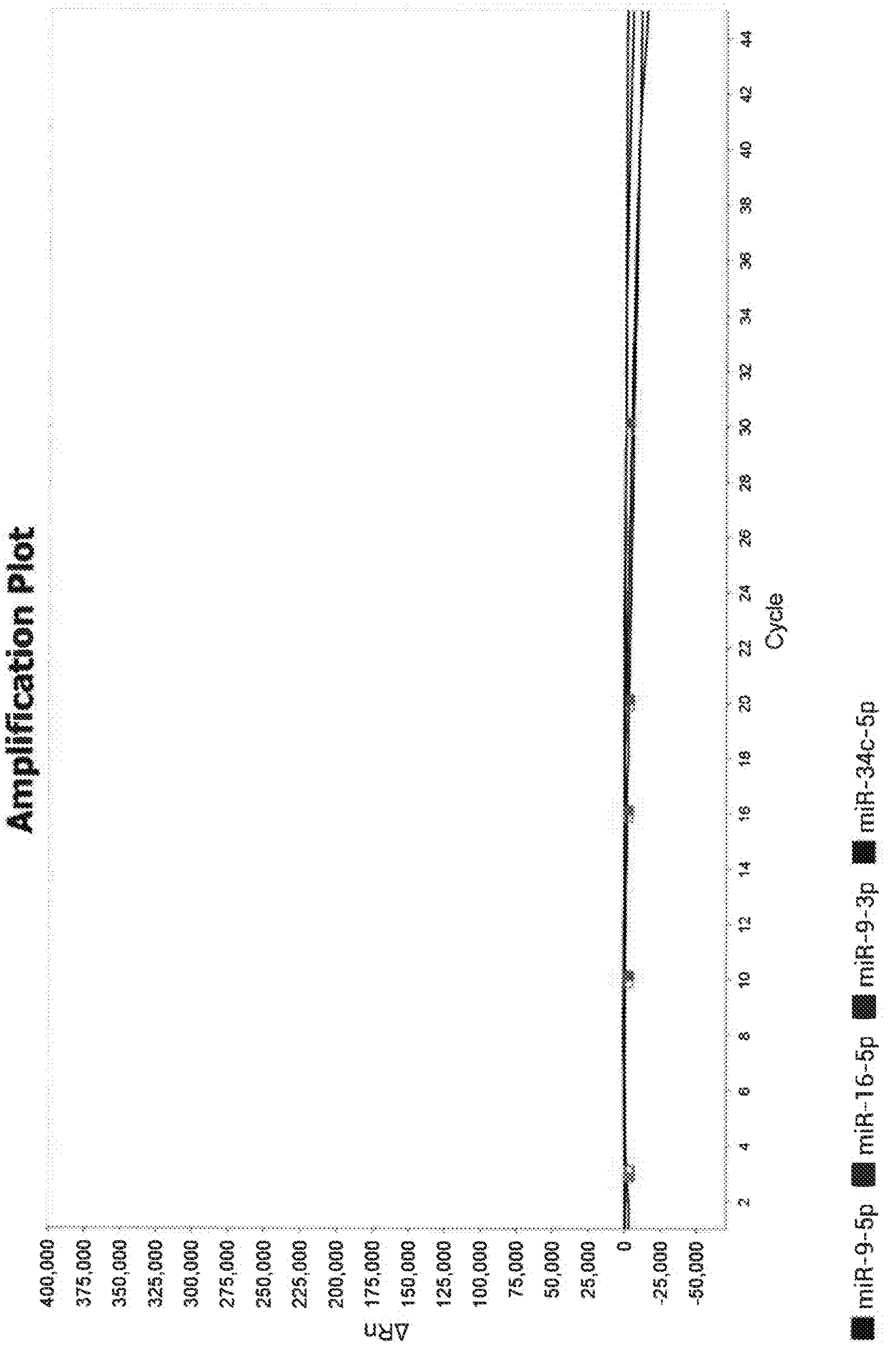
Figure 4A:
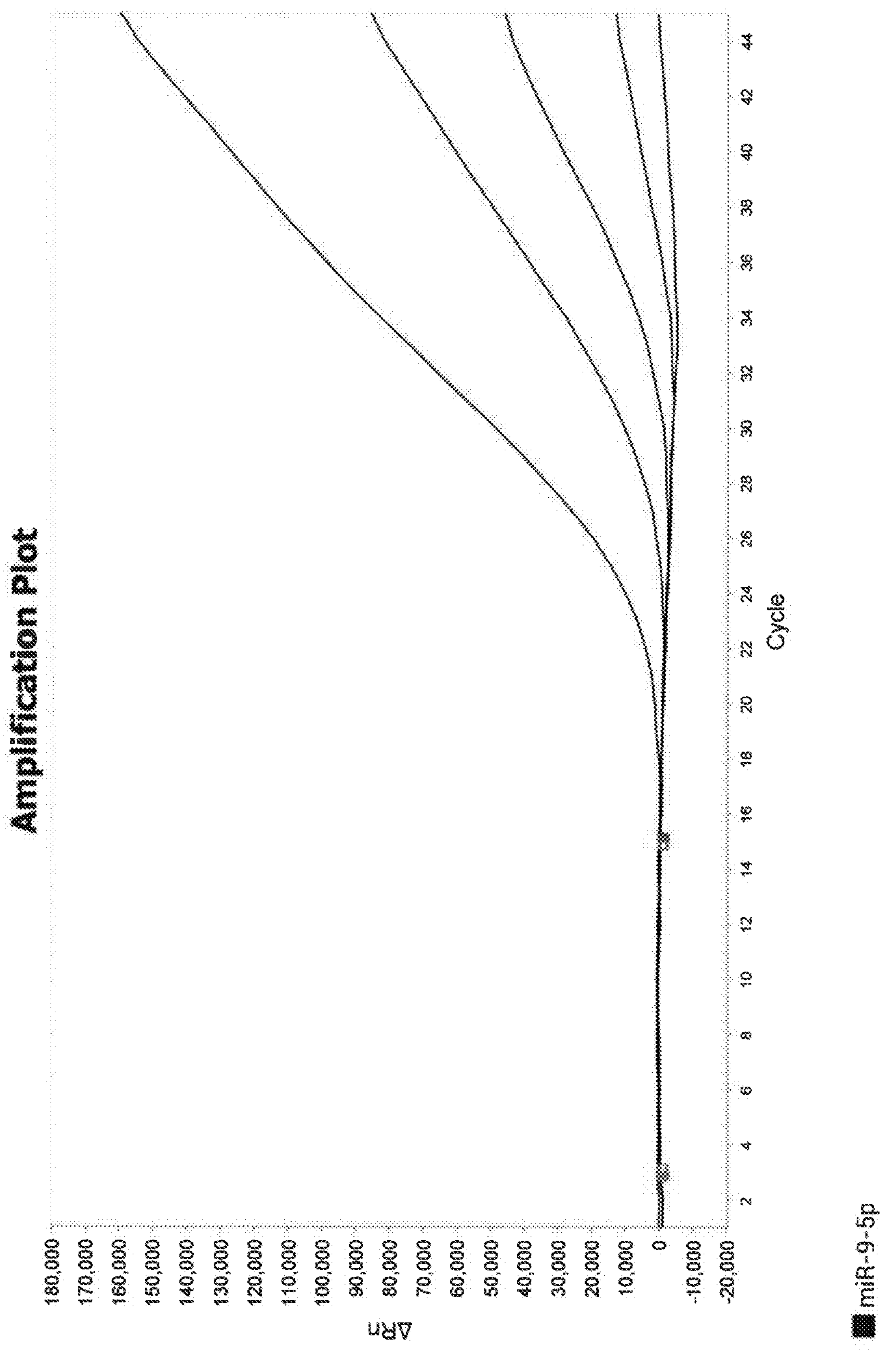
FIGS. 4A-D show sensitivity test results of each of the stem-loop reverse transcription primers for each of the target miRNAs.
Figure 4B:
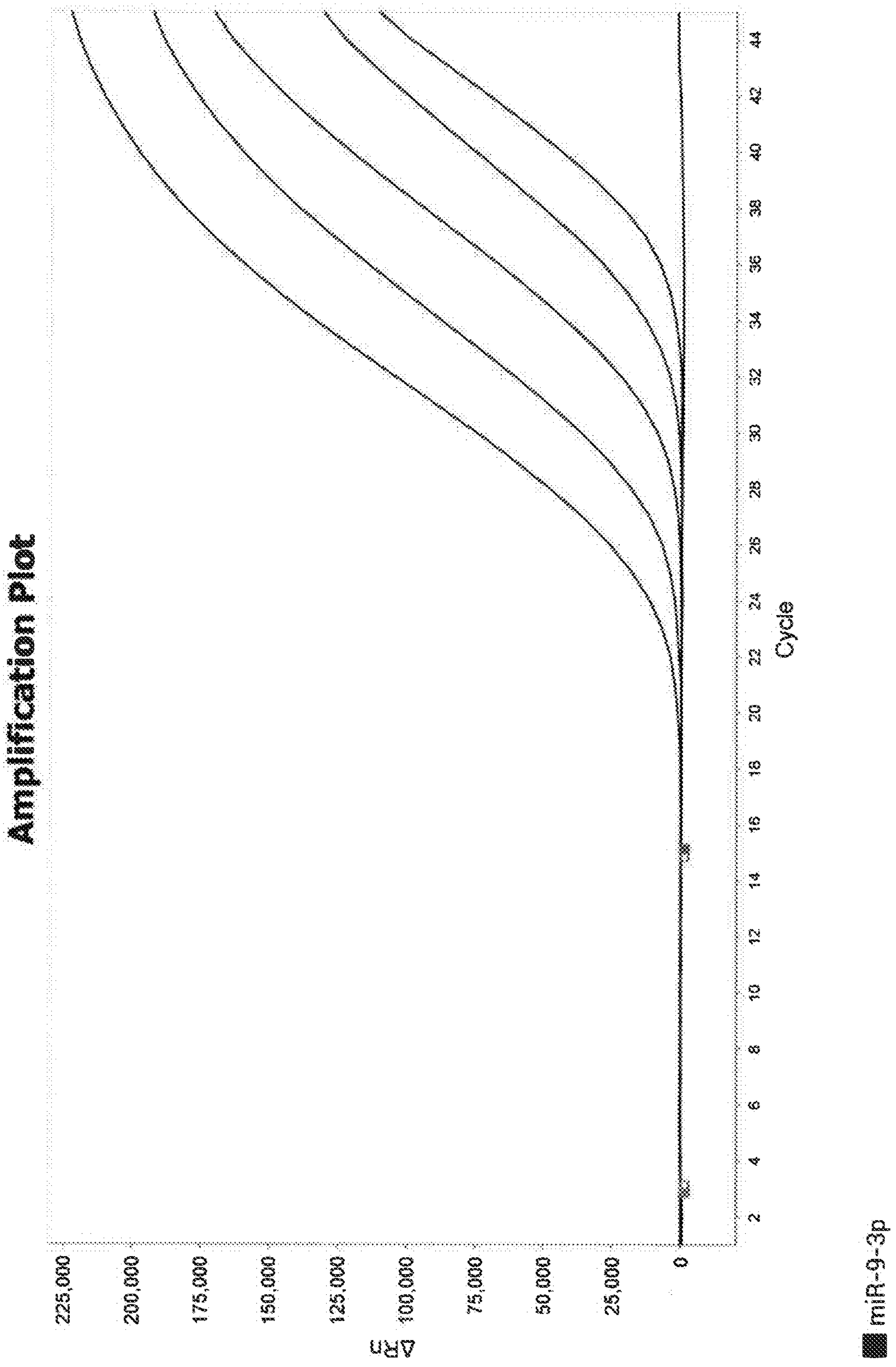
Figure 4C:
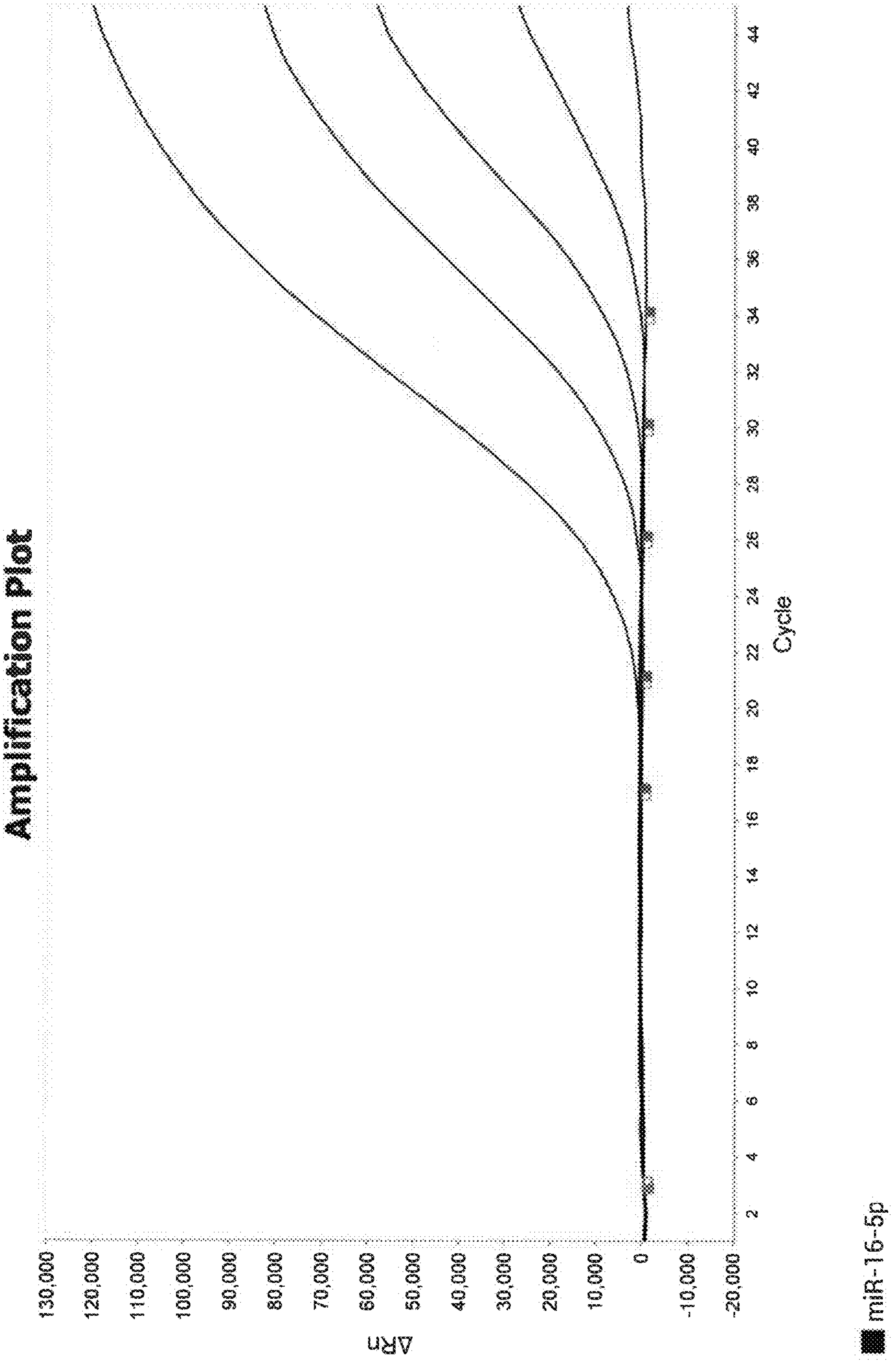
Figure 4D:
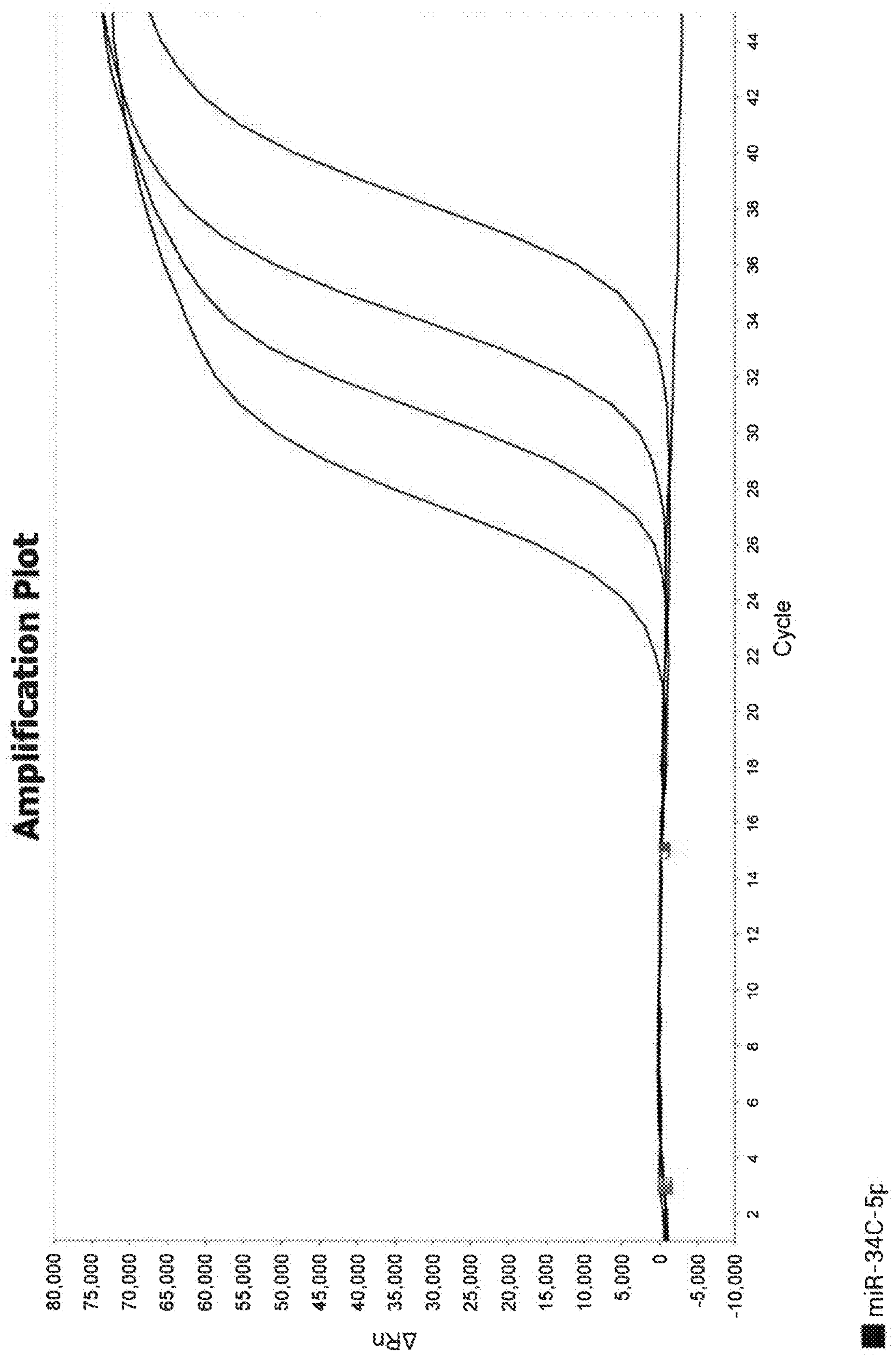

The quantification results produced in the qPCR are shown in Table 8 and FIG. 2A-D. The quantification results of singleplex RT-multiplex qPCRs with the stem-loop reverse transcription primers for miR-16-5p (with 6, 8, or 11 nt as the anchor sequence length) are shown in FIG. 2A. The quantification results of singleplex RT-multiplex qPCRs for miR-34c-5p (with 6, 8, or 11 nt as the anchor sequence length) are shown in FIG. 2B. The quantification results of singleplex RT-multiplex qPCRs for miR-9-3p (with 6, 8, or 11 nt as the anchor sequence length) are shown in FIG. 2C. The quantification results of singleplex RT-multiplex qPCRs for miR-9-5p (with 6, 8, or 11 nt as the anchor sequence length) are shown in FIG. 2D, and all of the stem-loop reverse transcription primers did not amplify in $ddH_2O$, indicating good specificity.

TABLE 8

Results of singleplex RT-qPCR using each of the stem-loop reverse transcription primer with different anchor sequence lengths (6/8/11 nt)

| Experimental grouping | Number of anchor bases of the reverse transcription primer | miR-16-5p | miR-34c-5p | miR-9-3p | miR-9-5p |
|---|---|---|---|---|---|
| miRNA synthesis template | 6 nt | 29.006 (SEQ ID No. 63) | 25.339 (SEQ ID No. 6) | 24.946 (SEQ ID No. 7) | 22.540 (SEQ ID No. 69) |
| | 8 nt | 25.222 (SEQ ID No. 5) | 26.934 (SEQ ID No. 65) | 25.852 (SEQ ID No. 67) | 23.034 (SEQ ID No. 68) |
| | 11 nt | 25.994 (SEQ ID No. 62) | 26.599 (SEQ ID No. 64) | 26.259 (SEQ ID No. 66) | 23.760 (SEQ ID No. 8) |
| $ddH_2O$ | 6 nt | Undetermined | Undetermined | Undetermined | Undetermined |
| | 8 nt | Undetermined | Undetermined | Undetermined | Undetermined |
| | 11 nt | Undetermined | Undetermined | Undetermined | Undetermined |
| $ddH_2O$ | H | Undetermined | Undetermined | Undetermined | Undetermined |

Construction of Multiplex RT-qPCR for Quantifying Multiple Target miRNAs

Each of the stem-loop reverse transcription primers is selected for each of the target miRNAs. The length of the anchor sequence of each of the stem-loop reverse transcription primers can be adjusted so as to form more than one possible combinations of the stem-loop reverse transcription primers. In one embodiment, the stem-loop sequences of all the stem-loop reverse transcription primers are the same. In another embodiment, the stem-loop sequence of each of the stem-loop reverse transcription primers is different from the others. Multi-specificity and sensitivity are tested for each of the combinations of stem-loop reverse transcription primers. When a combination passes the specificity test, it is considered as a potential combination for the multiplex RT-qPCR quantifying the multiple target miRNAs. Sensitivity test can be done thereafter to determine the detection limit for the target miRNAs. In order to increase the efficiency of screening, the selection of stem-loop reverse transcription primers can stop once the multi-specificity for a particular combination is confirmed. This combination is then used for the multiplex RT-qPCR quantification of the target miRNAs combination. To obtain an optimized stem-loop reverse transcription primer combination, the lengths of anchor sequences of the stem-loop reverse transcription primers can be adjusted and more combinations with different anchor sequence lengths can be formed. Multi-specificity and sensitivity tests are accomplished for these combinations with different anchor sequences, such that an optimized combination of primers with best specificity and sensitivity can be obtained.

Specifically, for miR-16-5p, a stem-loop reverse transcription primer with an anchor sequence length of 8 nucleotides was selected. For miR-34c-5p, a stem-loop reverse transcription primer with an anchor sequence length of 6 nucleotides was selected. For miR-9-3p, a stem-loop reverse transcription primer with an anchor sequence length of 6 nucleotides was selected. For miR-9-5p, a stem-loop reverse transcription primer with an anchor sequence length of 11 nucleotides was selected. These stem-loop reverse transcription primers were combined to form a stem-loop reverse transcription primer combination, as shown in Table 9.

TABLE 9

The screened stem-loop reverse transcription primers

| miRNA | Stem-loop reverse transcription primer | Stem-loop primer sequence | Stem-loop sequence | Anchor sequence |
|---|---|---|---|---|
| miR-16-5p | miR-16-5p-RT8 | SEQ ID No. 5 | SEQ ID No. 9 | CGCCAATA SEQ ID No. 13 |
| miR-34c-5p | miR-34c-5p-RT6 | SEQ ID No. 6 | SEQ ID No. 10 | GCAATC SEQ ID No. 14 |
| miR-9-3p | miR-9-3p-RT6 | SEQ ID No. 7 | SEQ ID No. 11 | ACTTTC SEQ ID No. 15 |
| miR-9-5p | miR-9-5p-RT11 | SEQ ID No. 8 | SEQ ID No. 12 | TCATACAGCTA SEQ ID No. 16 |

This combination of the stem-loop reverse transcription primers was set as an example for validations of the multi-specificity, sensitivity and stability.

Multi-Specificity Test for the Screened Stem-Loop Reverse Transcription Primer Combination Each of the stem-loop reverse transcription primers selected was used separately to perform a singleplex reverse transcription with a mixed target miRNA template (miR-16-5p, miR-34c-5p, miR-9-3p, miR-9-5p), and each singleplex reverse transcription system was shown in Table 10.

TABLE 10

Singleplex reverse transcription system for each of the stem-loop reverse transcription primers

| Reagent | 20 μL system |
|---|---|
| 10X RT MIX | 2 μL |
| HiScript II Enzyme Mix | 2 μL |
| Mixed RNA template | 10 pg-1 μg |
| Stem-loop reverse transcription primer (2 μM) | 0.5 μL |
| $ddH_2O$ | To 20 μL |

To verify the multi-specificity of the stem-loop reverse transcription primer combination, the reverse transcription products of each of the singleplex reverse transcriptions were subjected to the multiplex qPCR to determine if there was cross-reaction in the quantifications of the four target miRNAs. The multiplex qPCR system is shown in Table 11.

TABLE 11

Multiplex qPCR system

| Reagent | 20 μL system |
|---|---|
| Reverse transcription product | 2 μL |
| 2X Taq Pro HS U Probe Master Mix | 10 μL |
| TaqMan® probe combination (10 μM) | 0.2 μL |
| Forward primer combination (10 uM) | 0.4 μL |
| Reverse primer combination (10 uM) | 0.4 μL |
| $ddH_2O$ | To 20 μL |

The forward primer combination and reverse primer combination refer to the combination of the four forward primers and the four reverse primers shown in Table 2, and the probes combination refers to the combination of the four probes shown in Table 3.

As shown in FIGS. 3A-E, there is no cross-reaction in the quantification of each of the target miRNAs. The stem-loop reverse transcription primer combination, the forward/reverse primer combination, and the probe combination all have good multi-specificity. Therefore, this stem-loop reverse transcription primer combination can be used for the multiplex RT-qPCR quantification of the four target miRNAs: miR-16-5p, miR-34c-5p, miR-9-3p, and miR-9-5p. Based on the multi-specificity of the stem-loop reverse transcription primer combination detecting the four target miRNAs, any two or three of the stem-loop reverse transcription primers can form a sub-combination which has multi-specificity for detection of two or three of the target miRNAs, respectively.

Sensitivity Test for the Screened Stem-Loop Reverse Transcription Primer Combination To test the sensitivity of the screened stem-loop reverse transcription primer combination, the mixed target miRNA template (miR-16-5p, miR-34c-5p, miR-9-3p, miR-9-5p) are made into gradient dilution. Each template having a different concentration of the mixed target miRNAs undergoes the multiplex RT and then the multiplex qPCR using each of the screened stem-loop reverse transcription primers to determine the lowest concentration of the mixed target miRNA as the detection limit, i.e., sensitivity.

Specifically, the mixed target miRNAs template at a concentration of 1 pg/μL was diluted 10 times to 0.1 pg/μL, 0.01 pg/μL, 1 fg/μL, and 0.1 fg/μL for the singleplex RT, followed by the multiplex qPCR of the reverse transcription products obtained. The results are shown in FIGS. 4A-D. The detection limit for miR-9-5p was 1 fg/μL; 0.1 fg/μL for miR-9-3p; and 1 fg/μL for miR-16-5p and miR-34c-5p.

Comparison of Singleplex and Multiplex RT-qPCR of the Target miRNAs

With the informed consent of all the participants, 5 mL of peripheral blood was taken from the venous blood collection tube using the coagulation separation gel, allowed to stand for 30 minutes at room temperature, centrifuged at 3000×g for 10 minutes, the supernatant was taken, and stored at −80° C. refrigerator. Qiagen Serum/Plasma miRNA Extraction Kit was used for nucleic acid extraction by column method, with 200 μL serum and following the instructions of the kit, and finally dissolved in 20 μL of $ddH_2O$. The extracted miRNA samples were stored in a −80° C. refrigerator for later use.

Figure 5A:
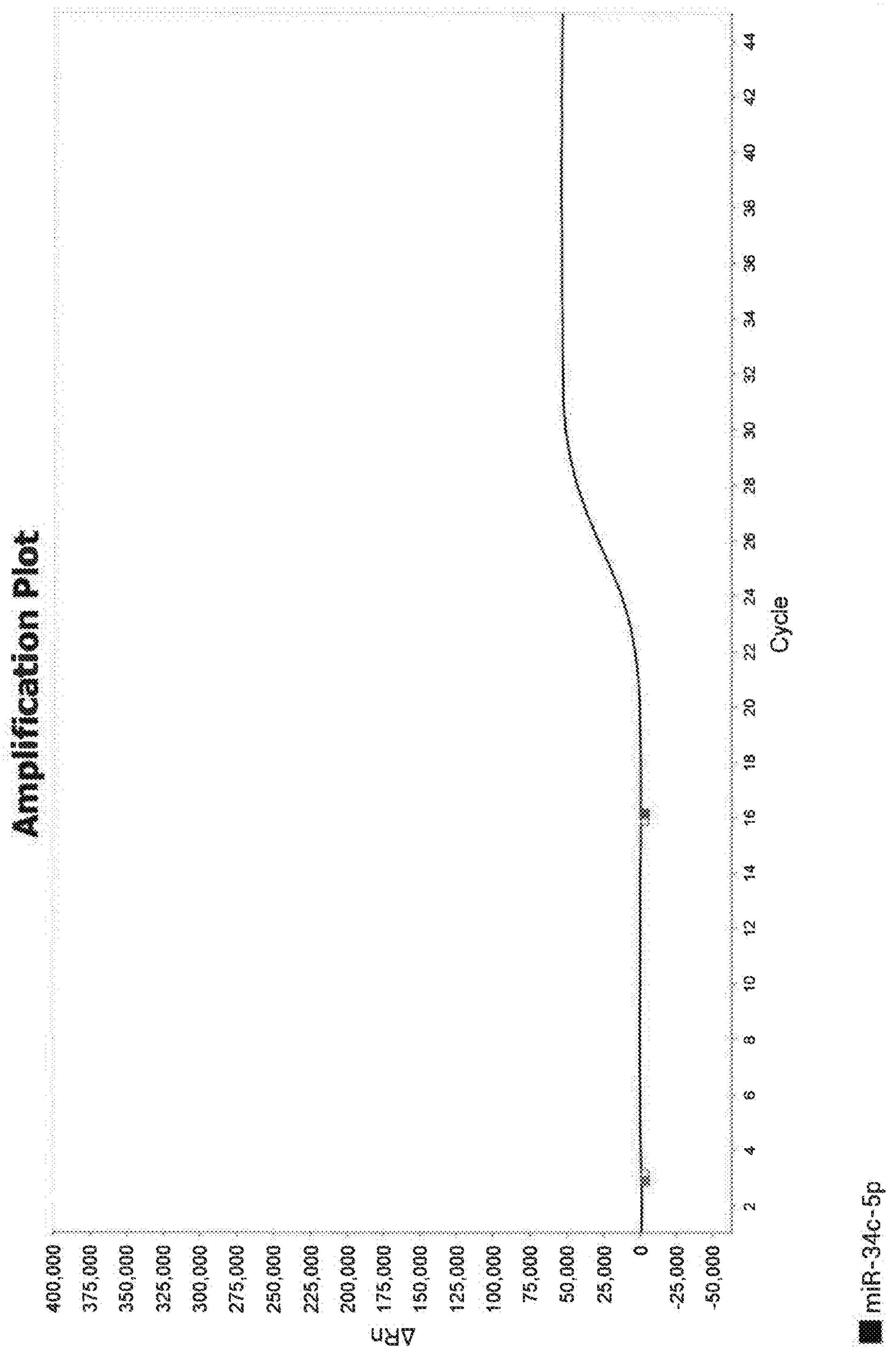
FIGS. 5A-F show comparisons between singleplex reverse transcription and multiplex reverse transcription of the multiple target miRNAs, respectively.
Figure 5B:
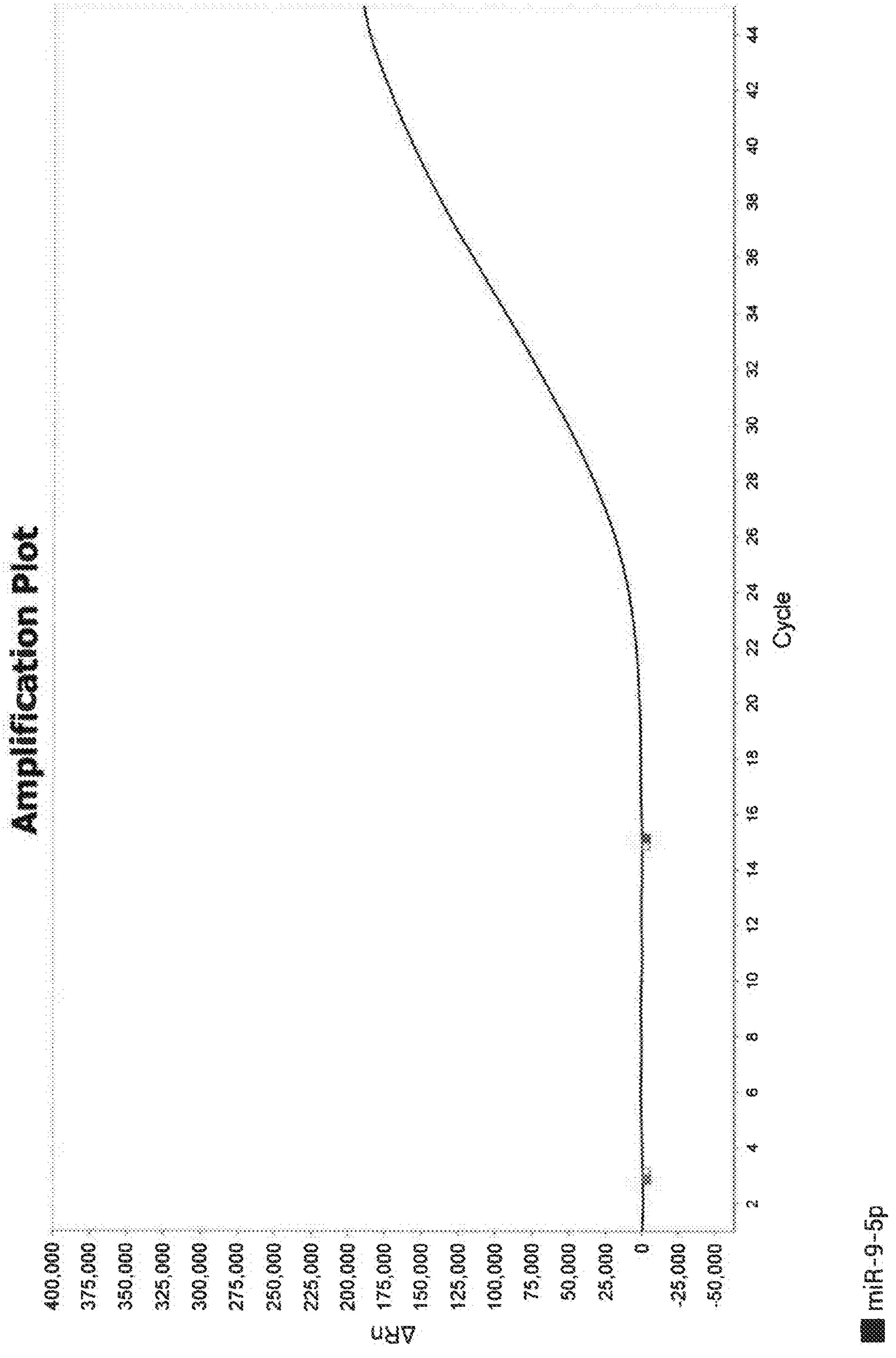
Figure 5C:
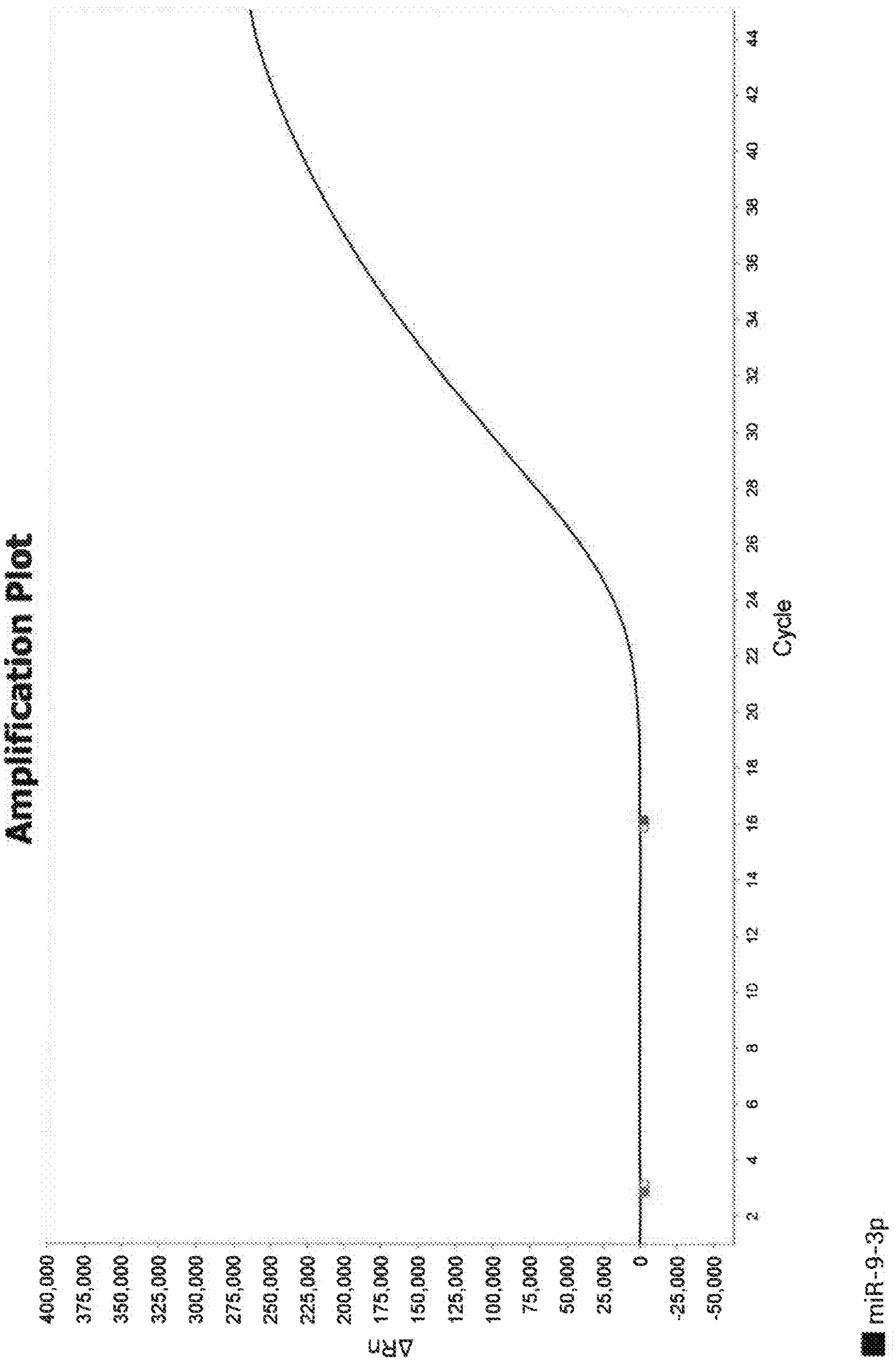
Figure 5D:
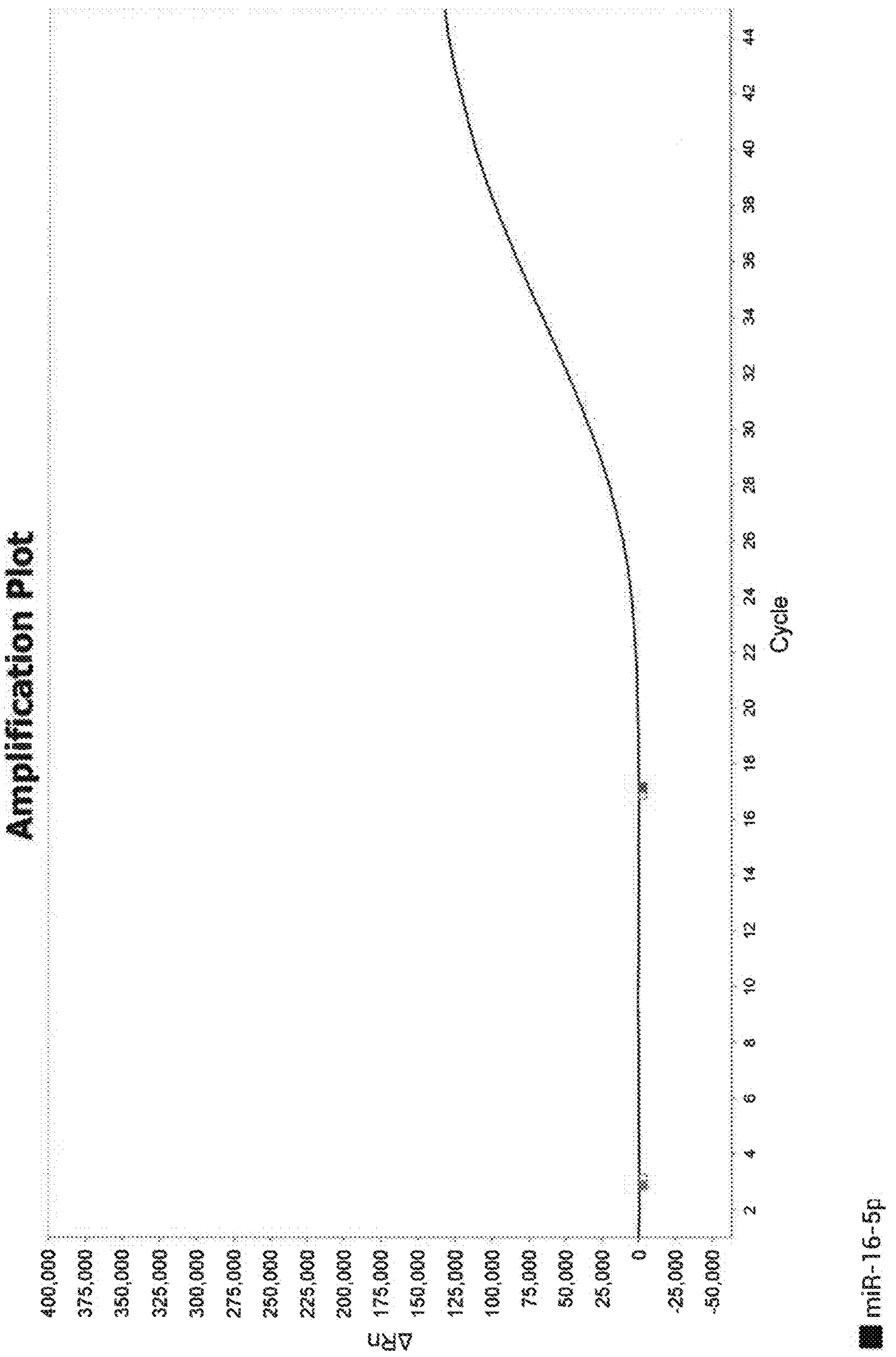
Figure 5E:
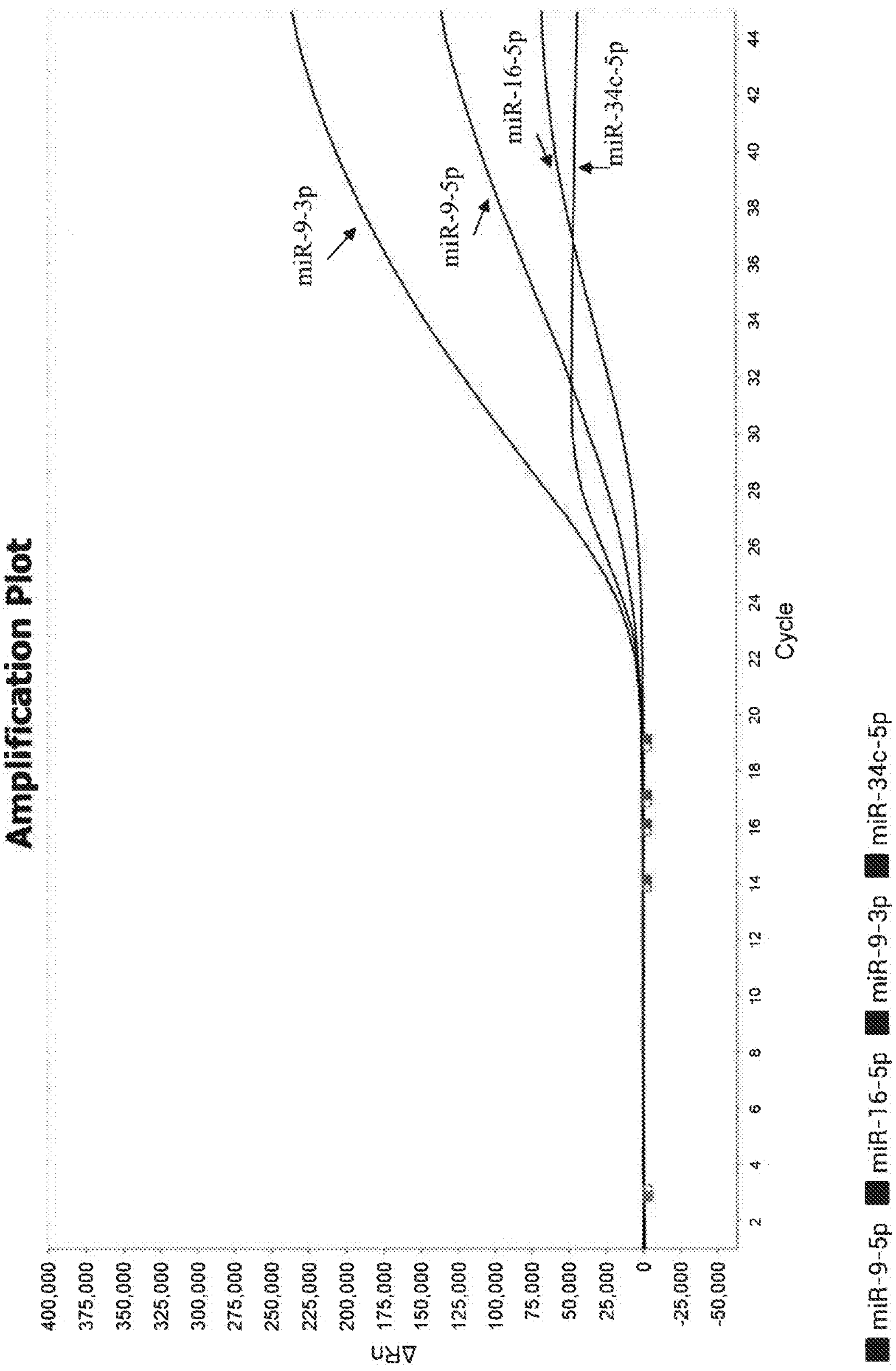
Figure 5F:
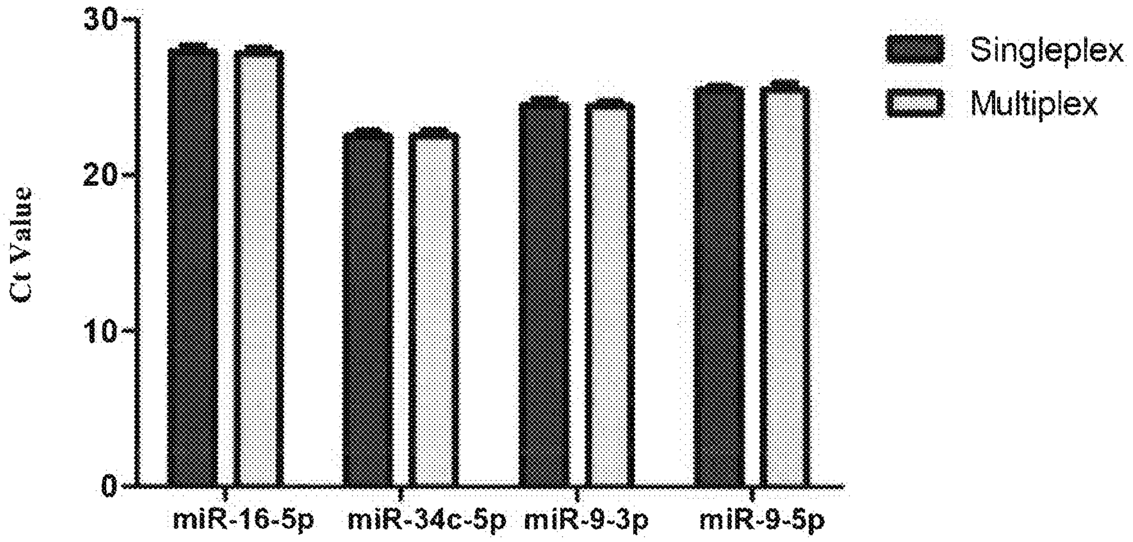
Figure 6A:
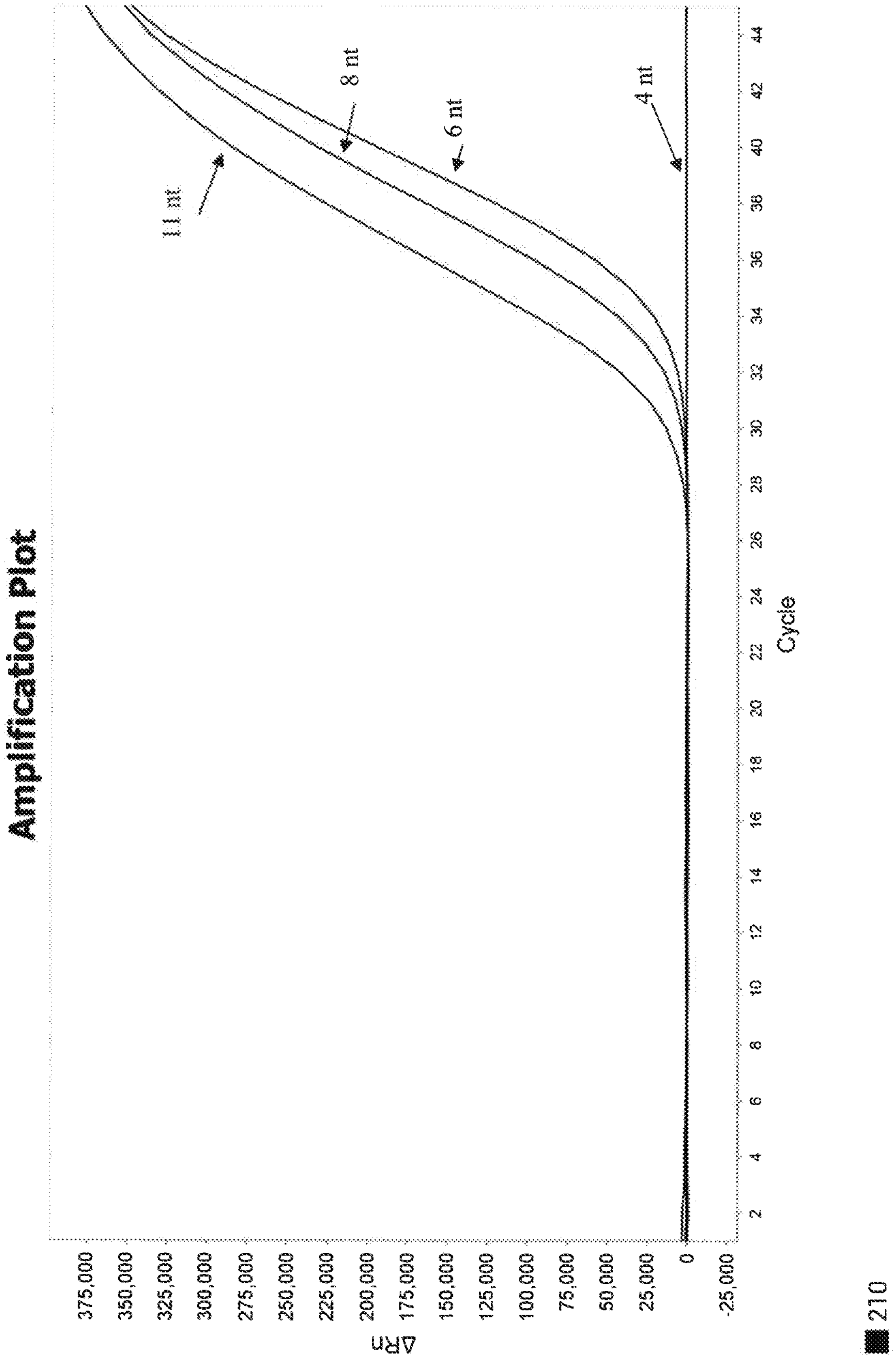
FIGS. 6A-H show amplification plots of singleplex RT-qPCR using each of the stem-loop reverse transcription primers with different anchor sequence lengths (4/6/8/11 nt) and a mixed template of the target miRNAs or negative control, respectively.
Figure 6B:
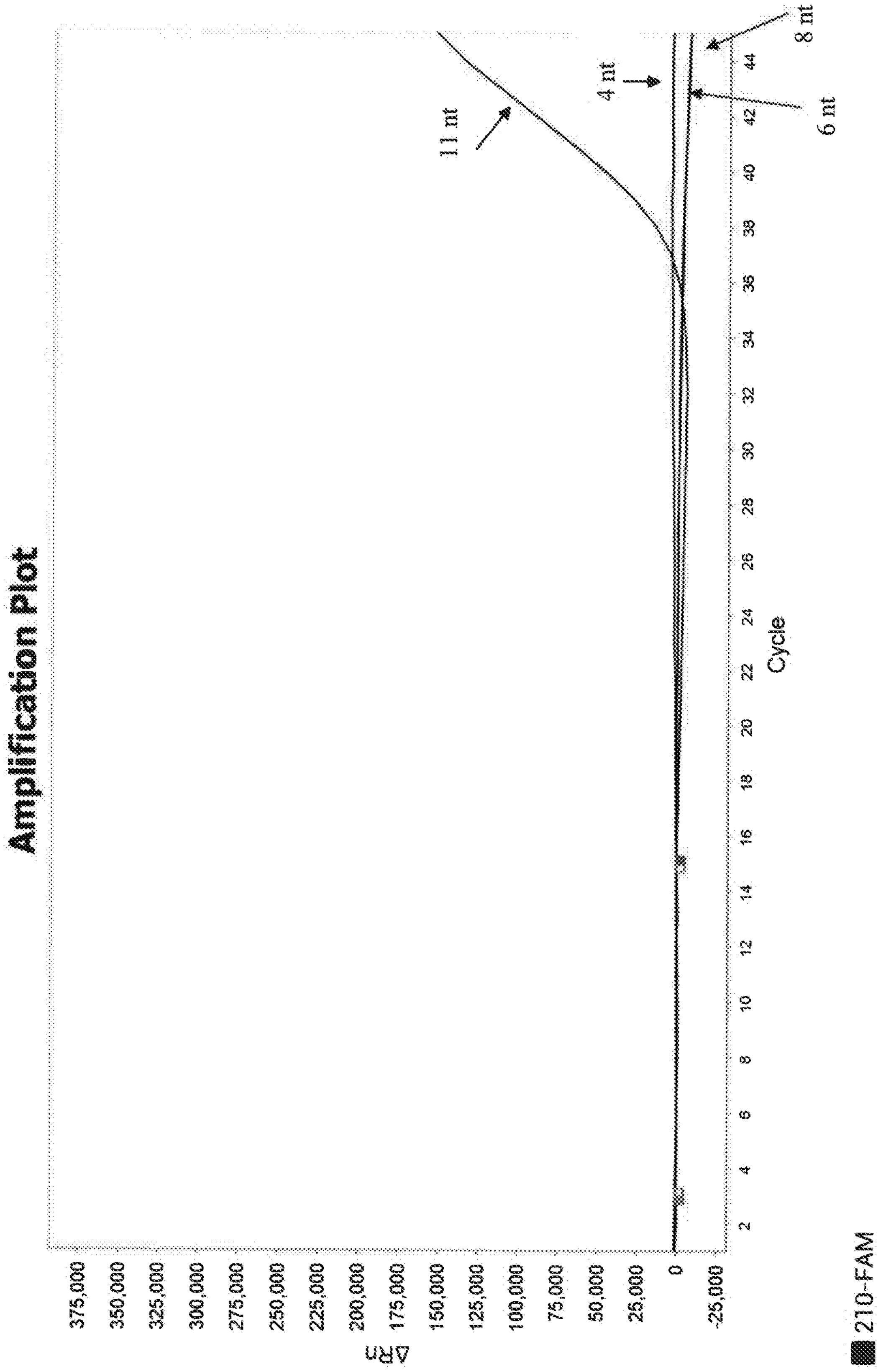
Figure 6C:
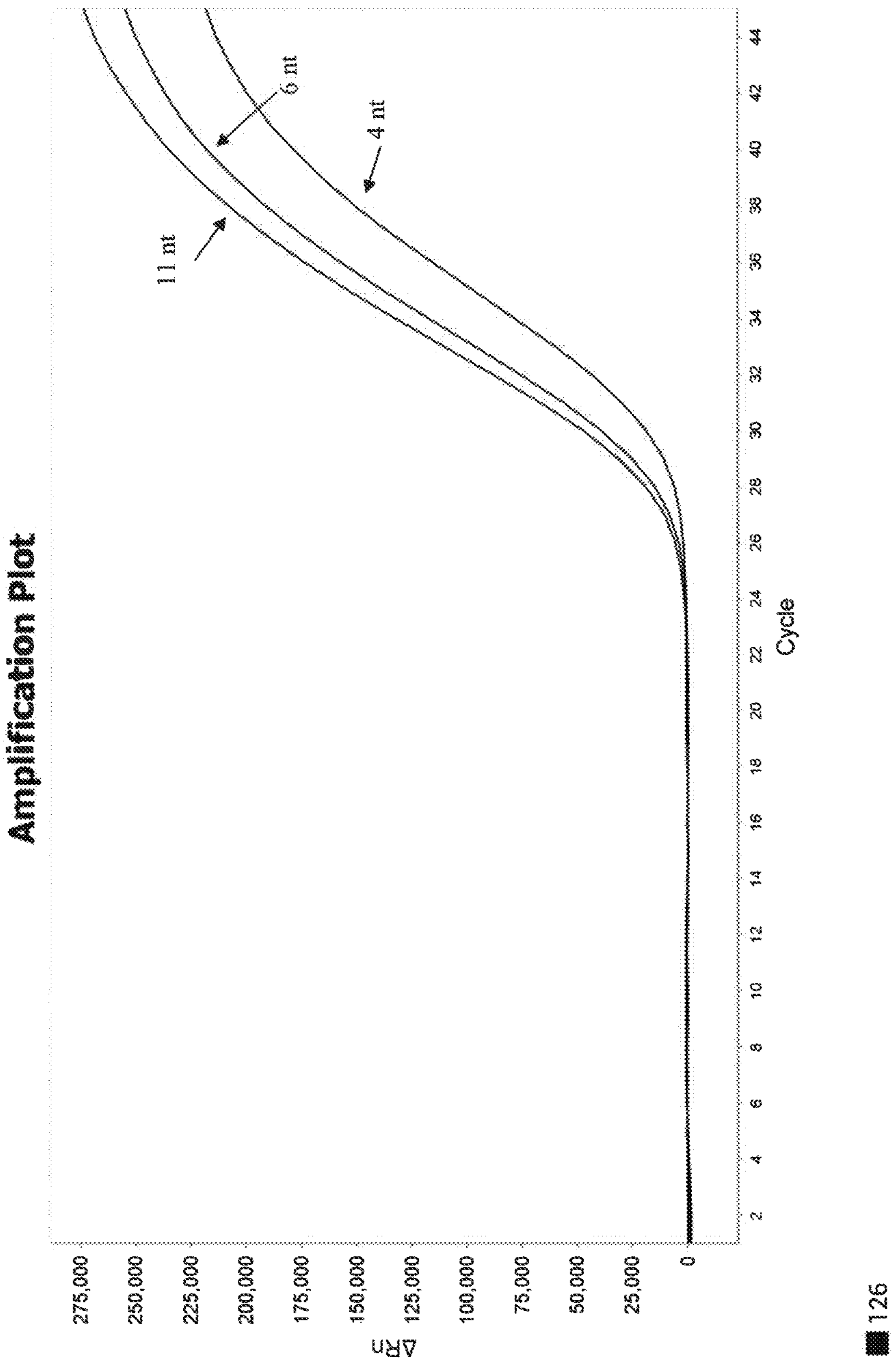
Figure 6D:
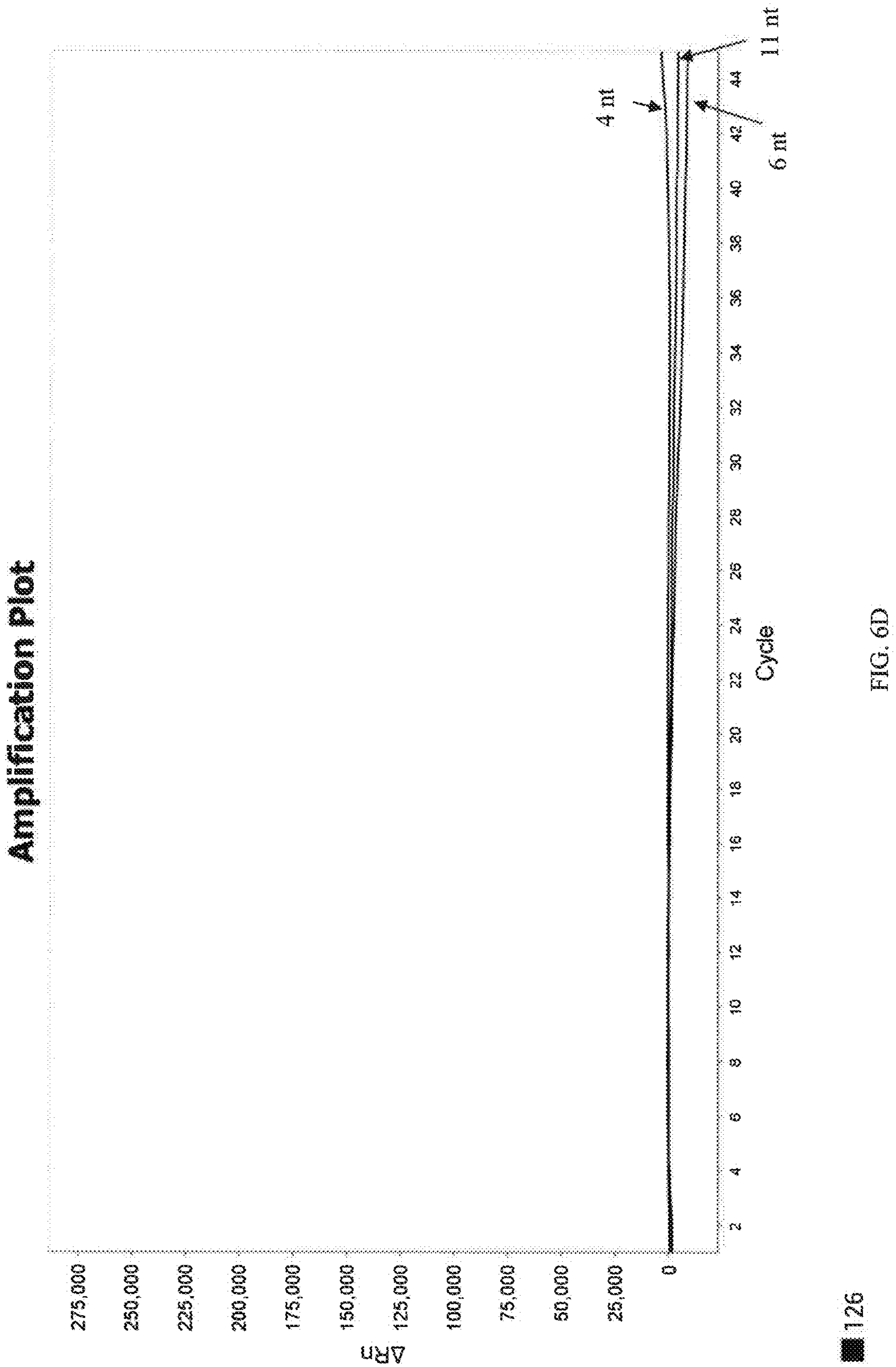
Figure 6E:
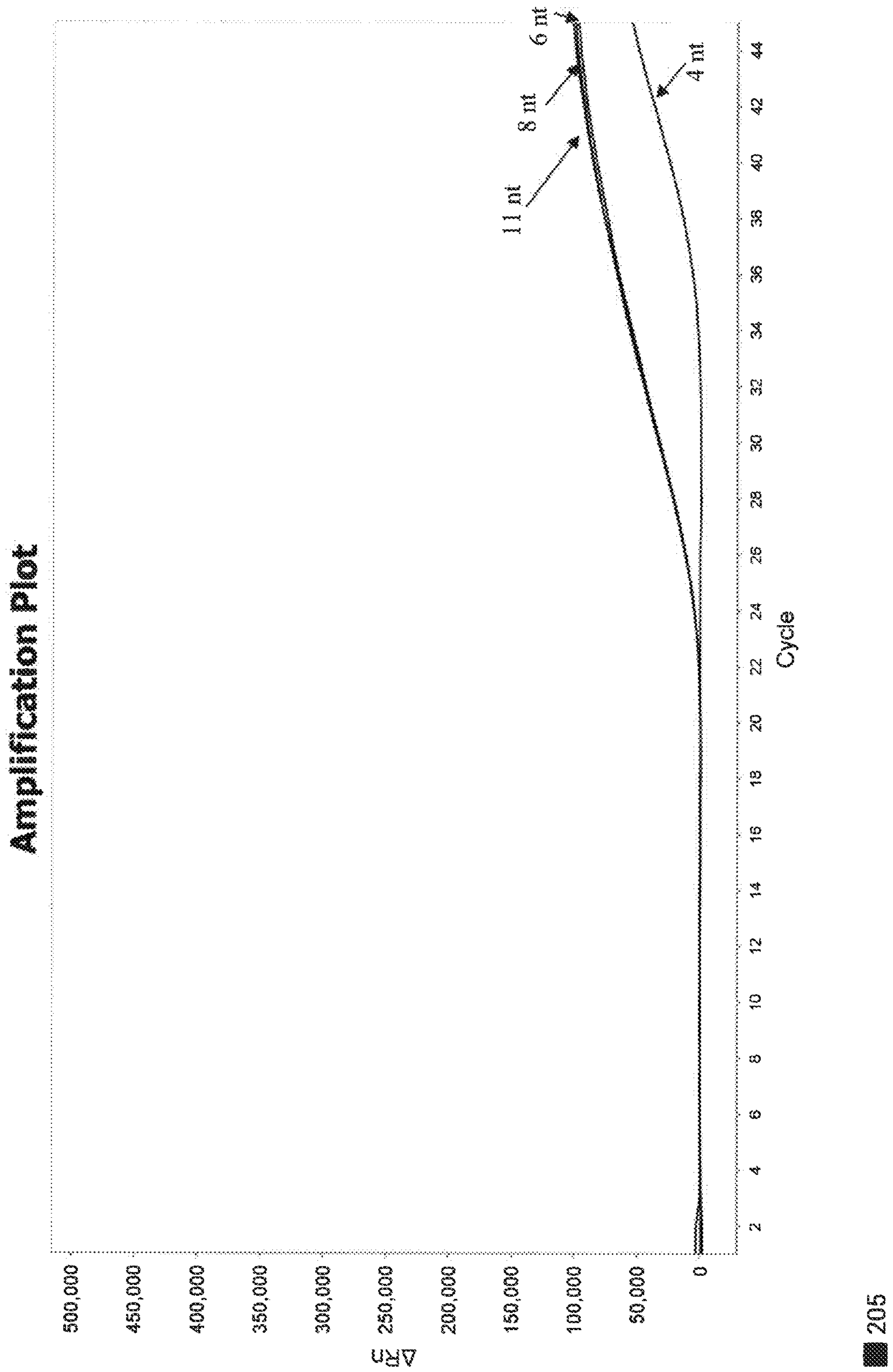
Figure 6F:
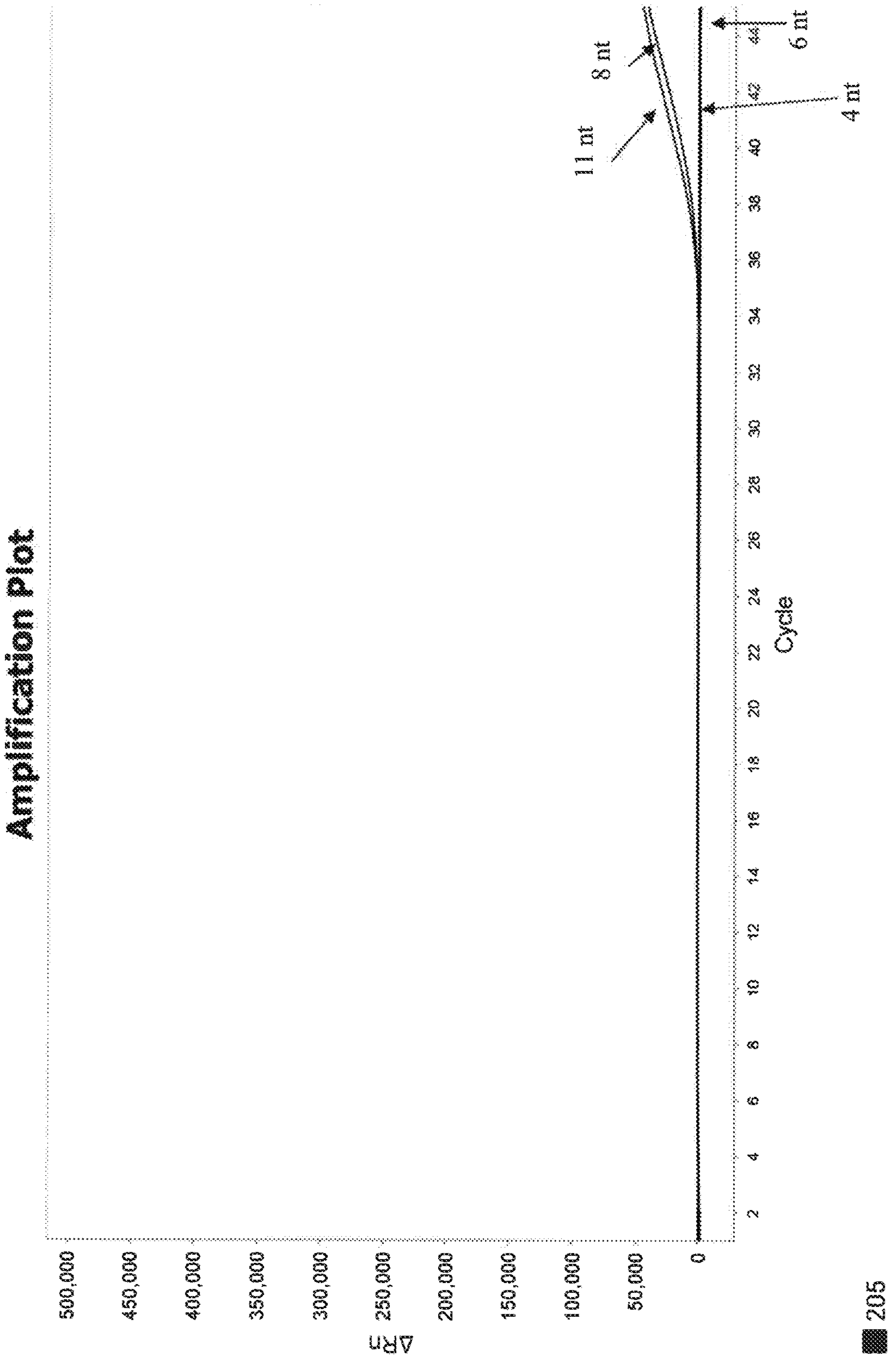
Figure 6G:
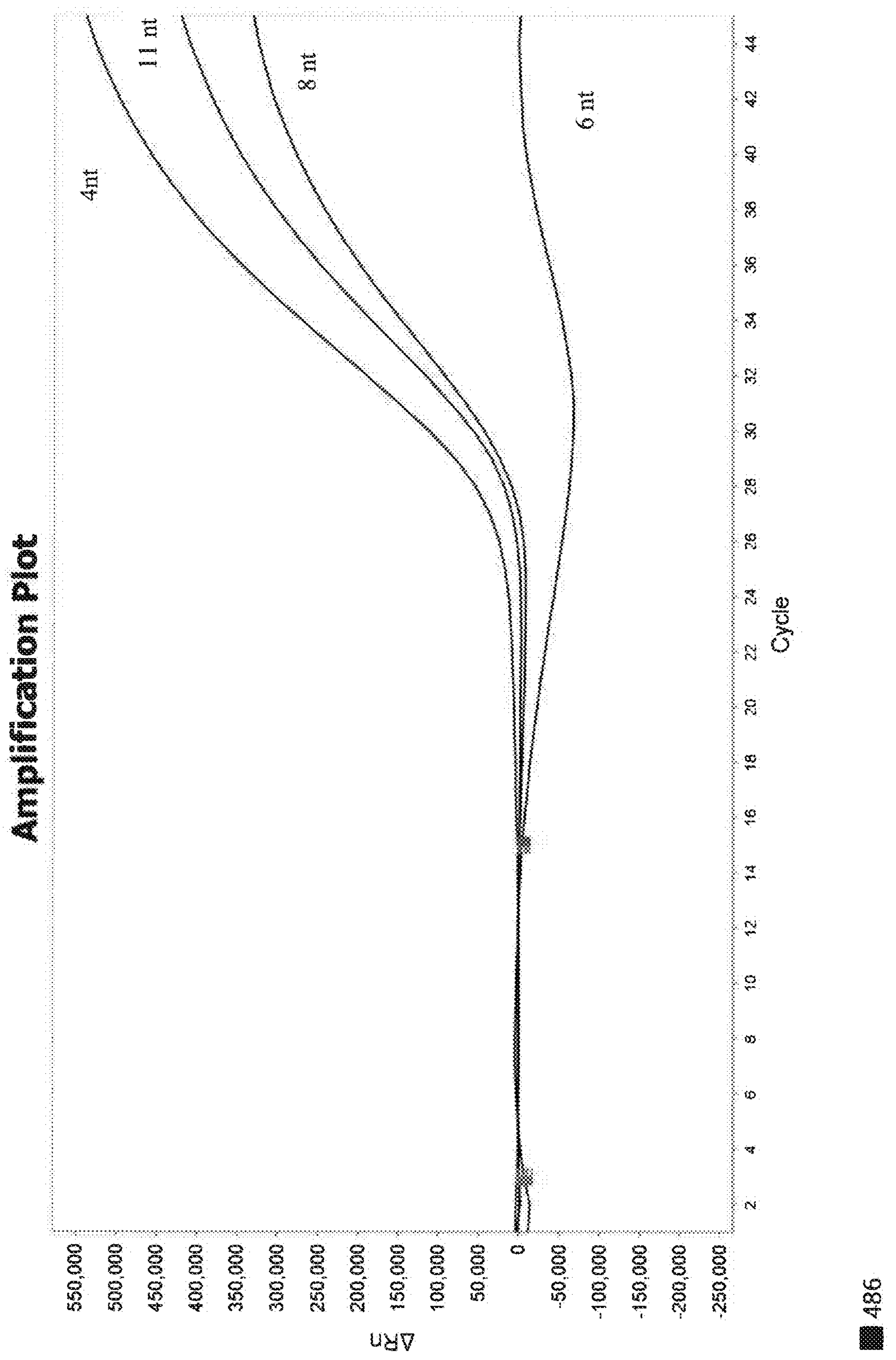
Figure 6H:
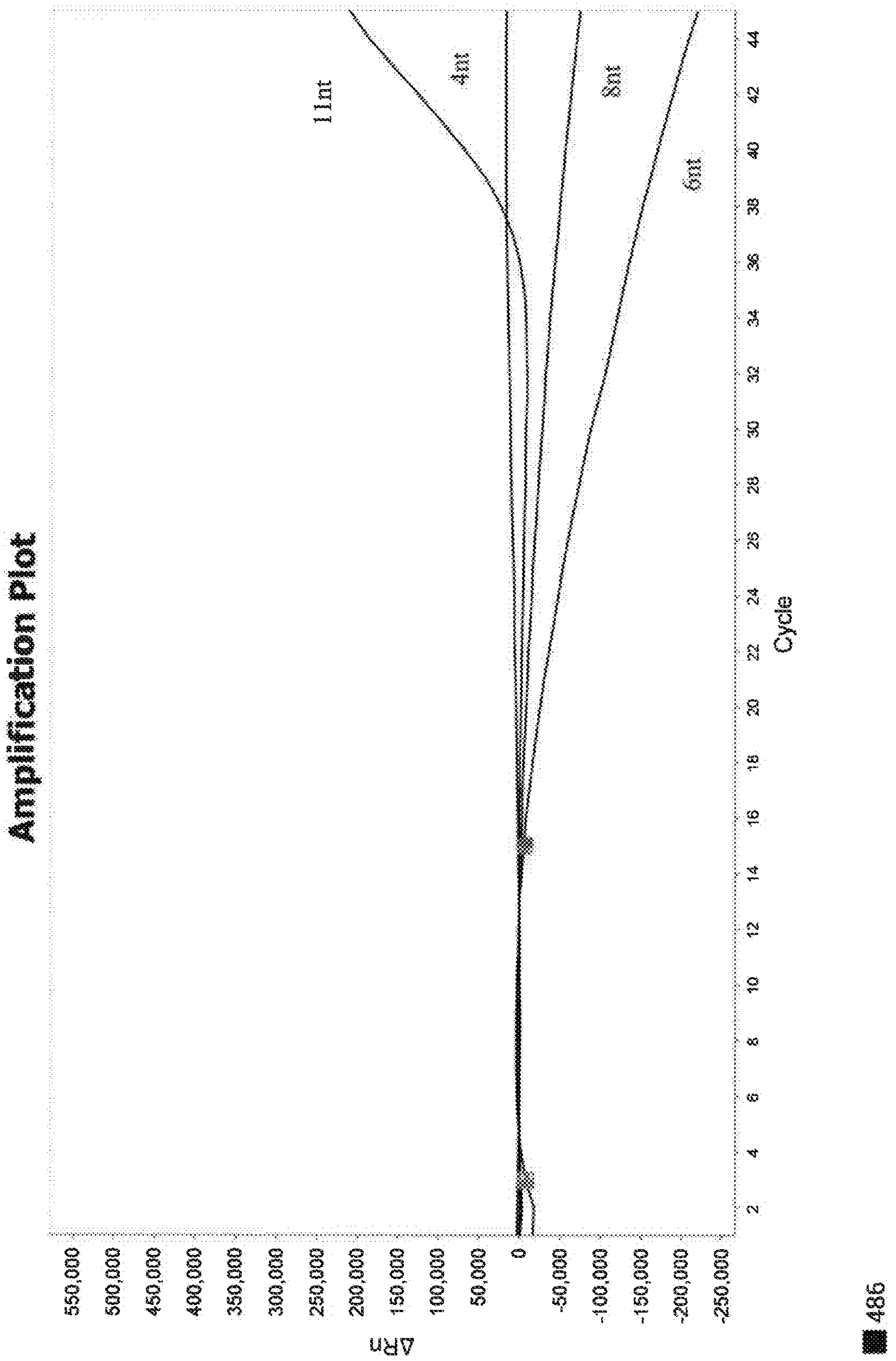
Figure 7A:
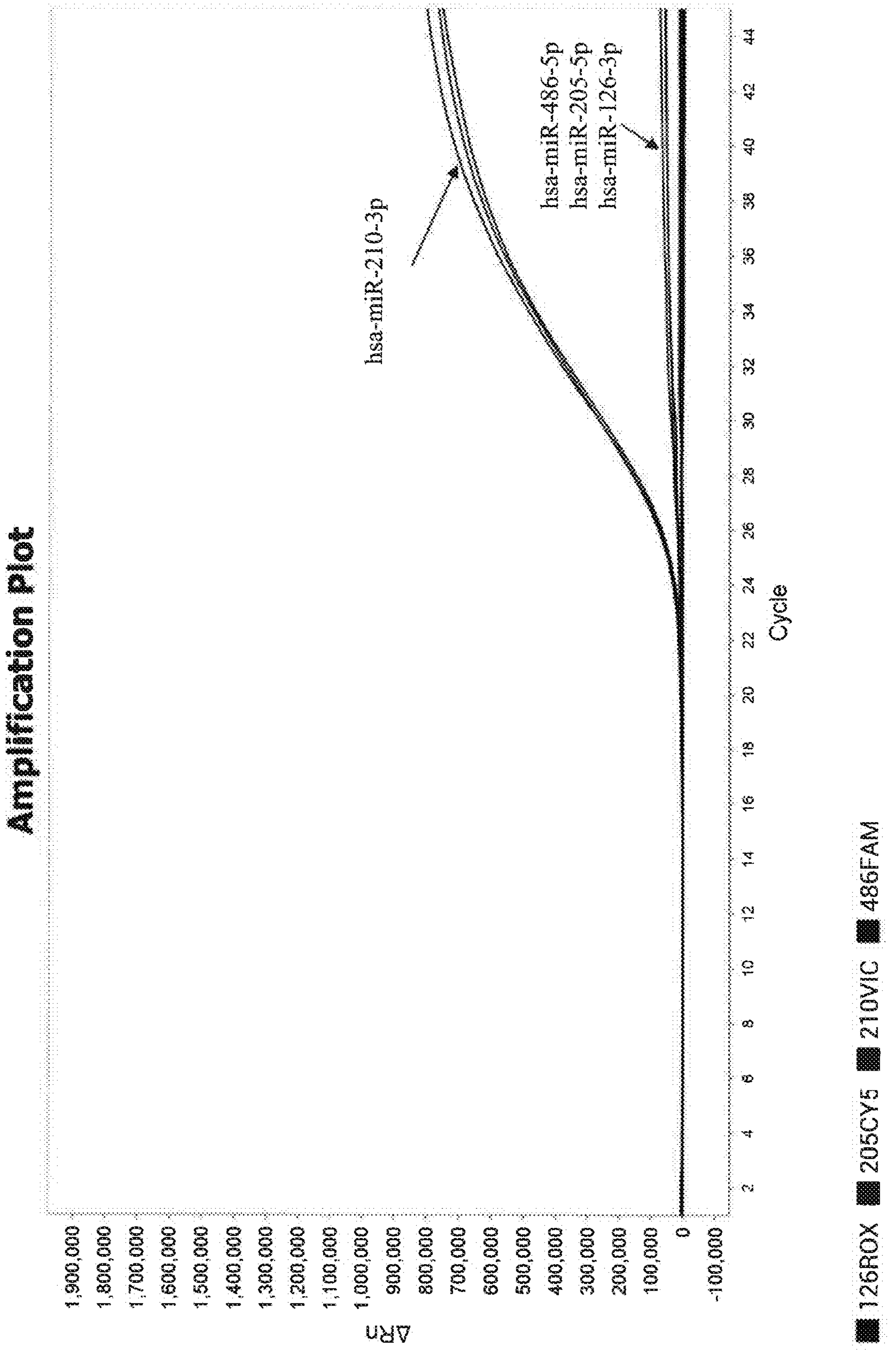
FIGS. 7A-D show amplification plots of singleplex RT-multiplex qPCR with each of the screened stem-loop reverse transcription primers for the mixed target miRNA templates, as well as amplification plots of singleplex RT-multiplex qPCR using $ddH_2O$ and negative control, respectively.
Figure 7B:
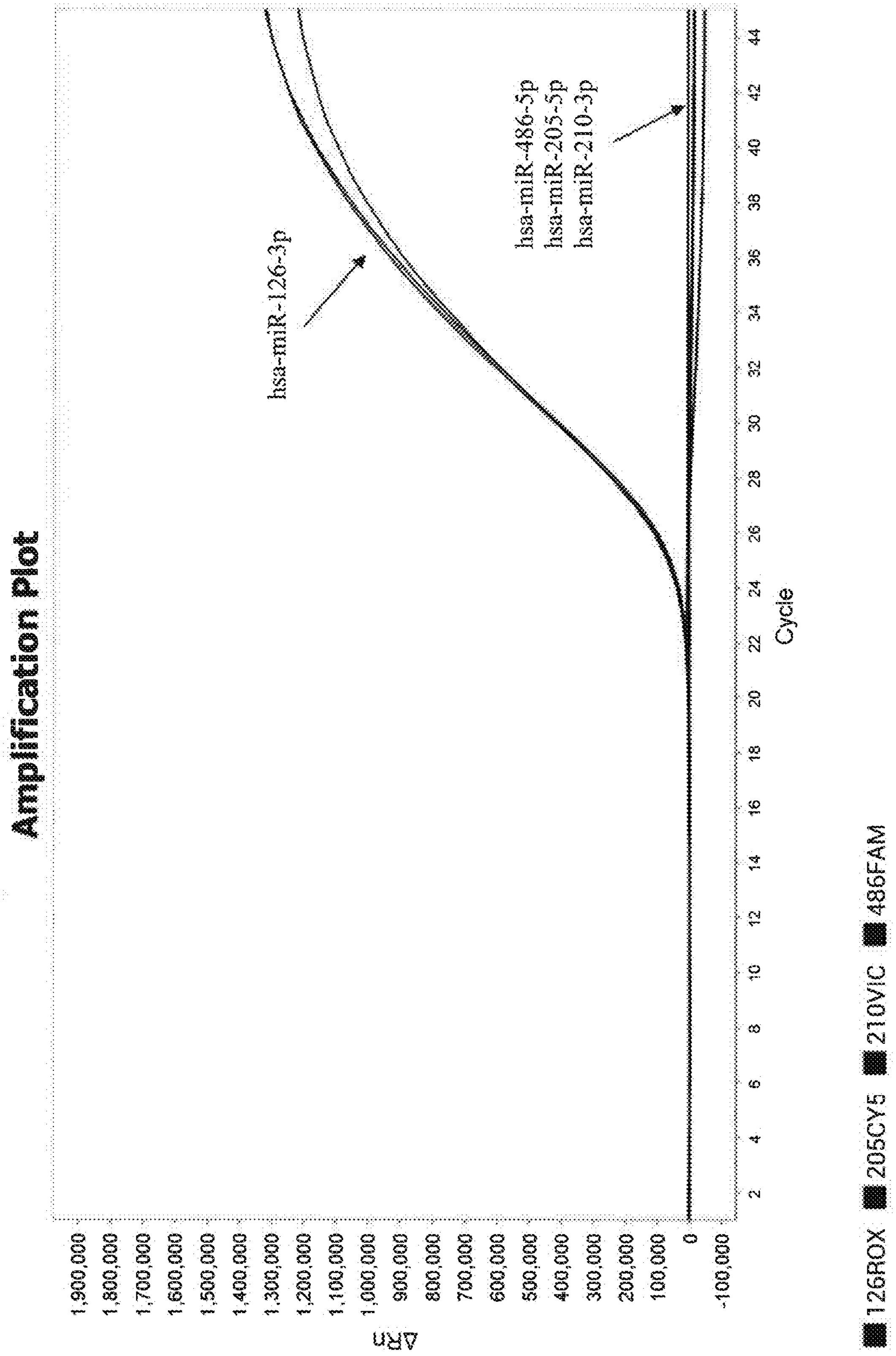
Figure 7C:
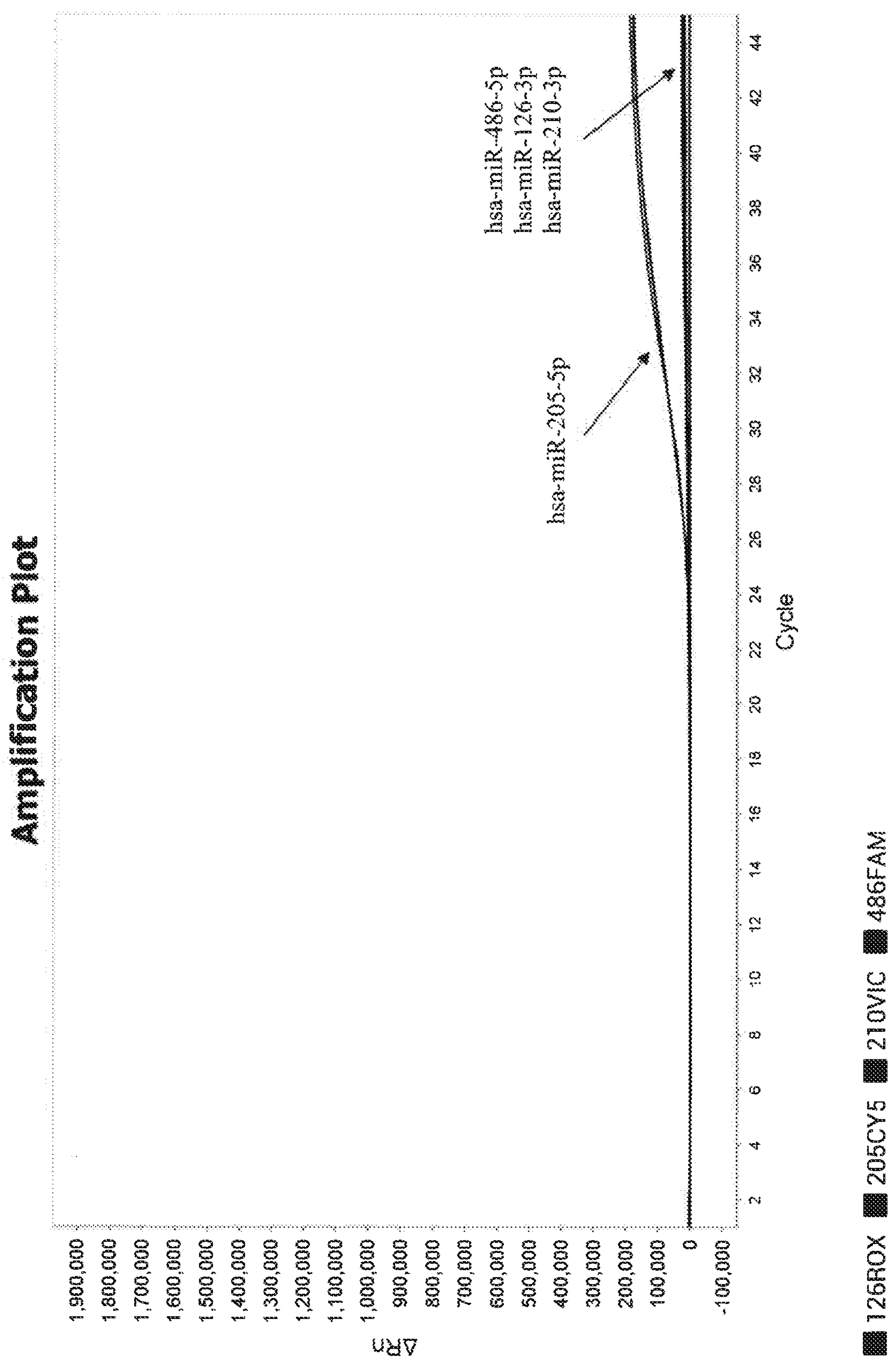
Figure 7D:
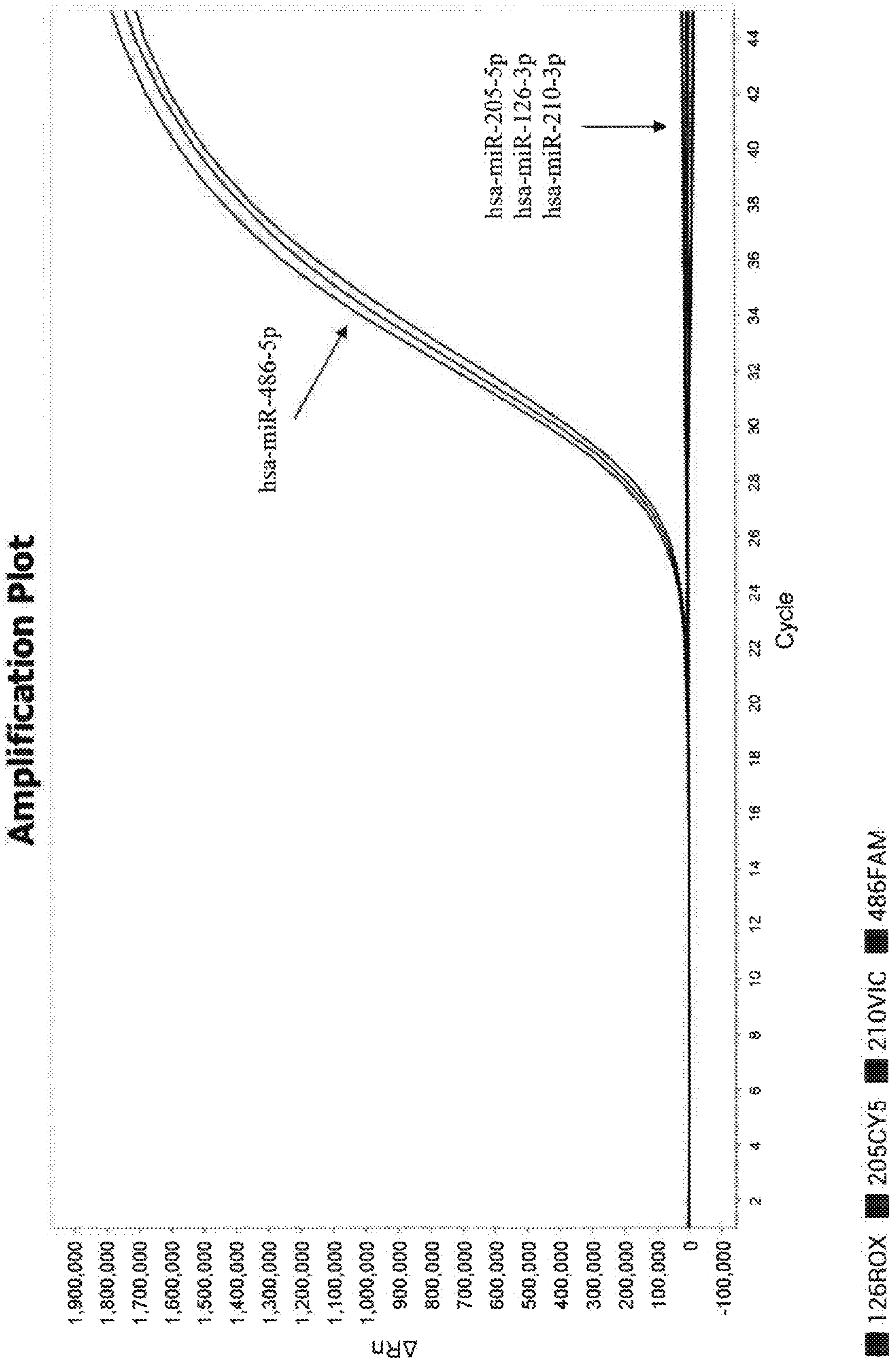
Figure 8A:
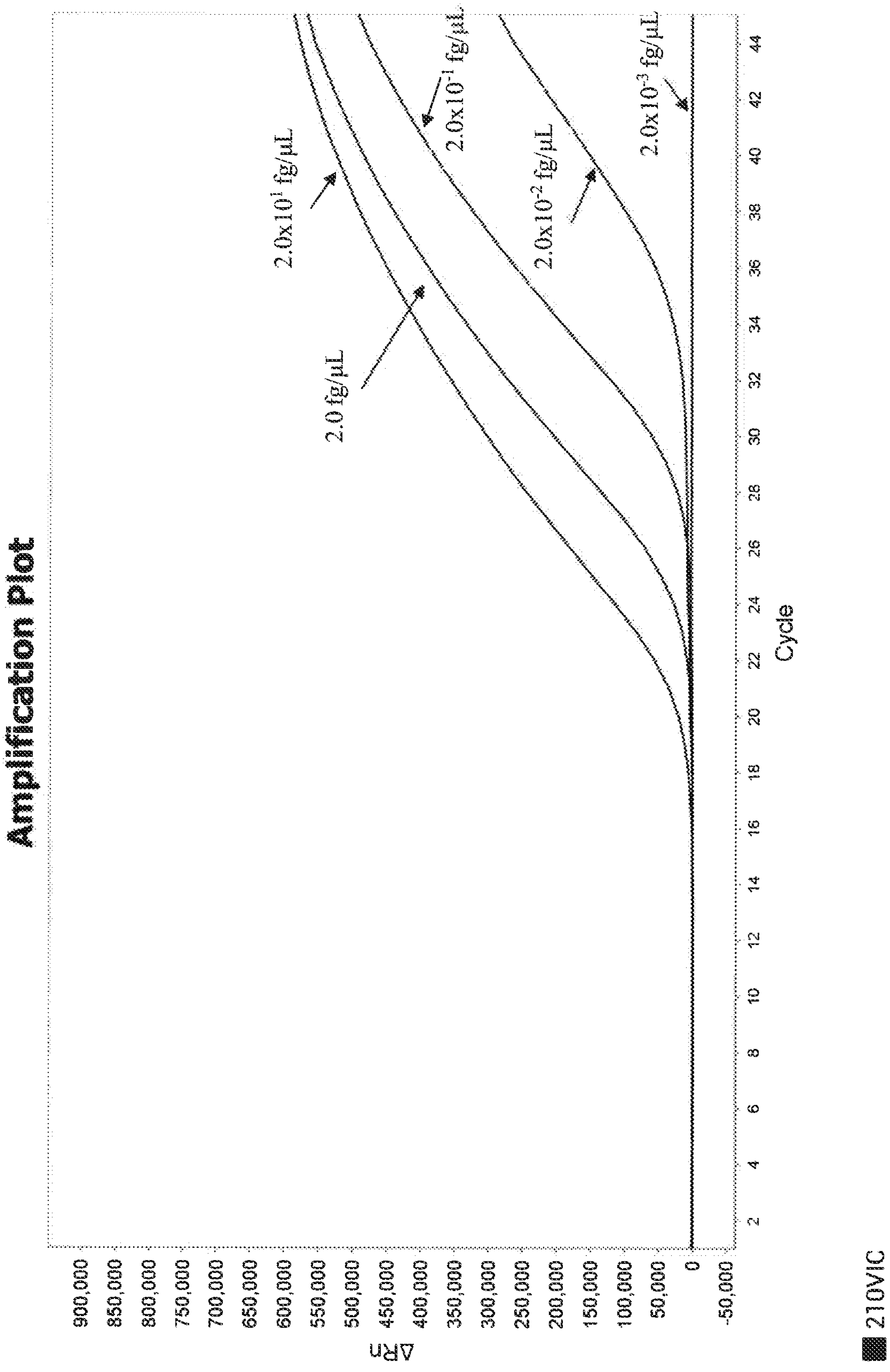
FIGS. 8A-D show sensitivity testing results of each of the target miRNAs.
Figure 8B:
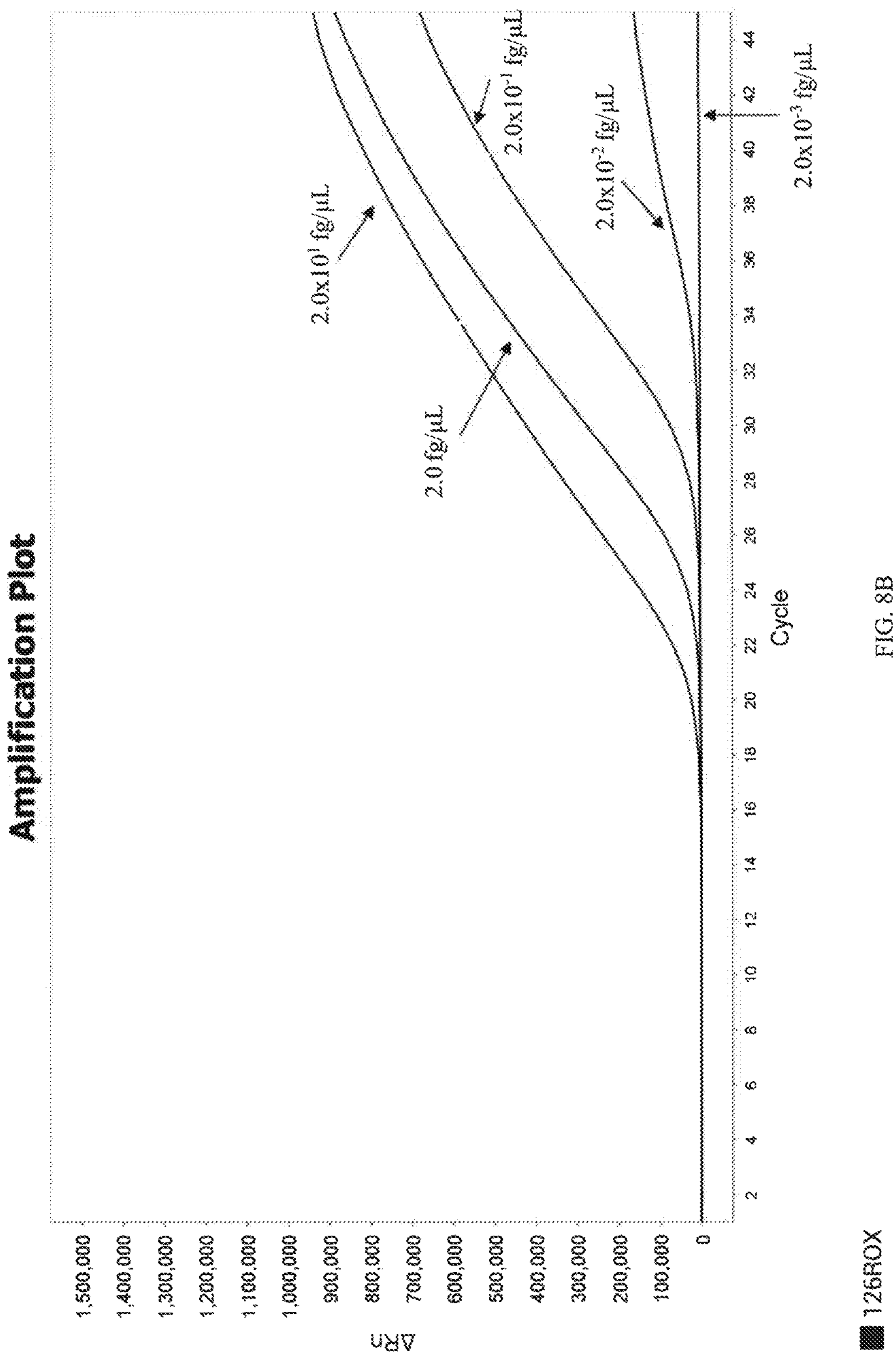
Figure 8C:
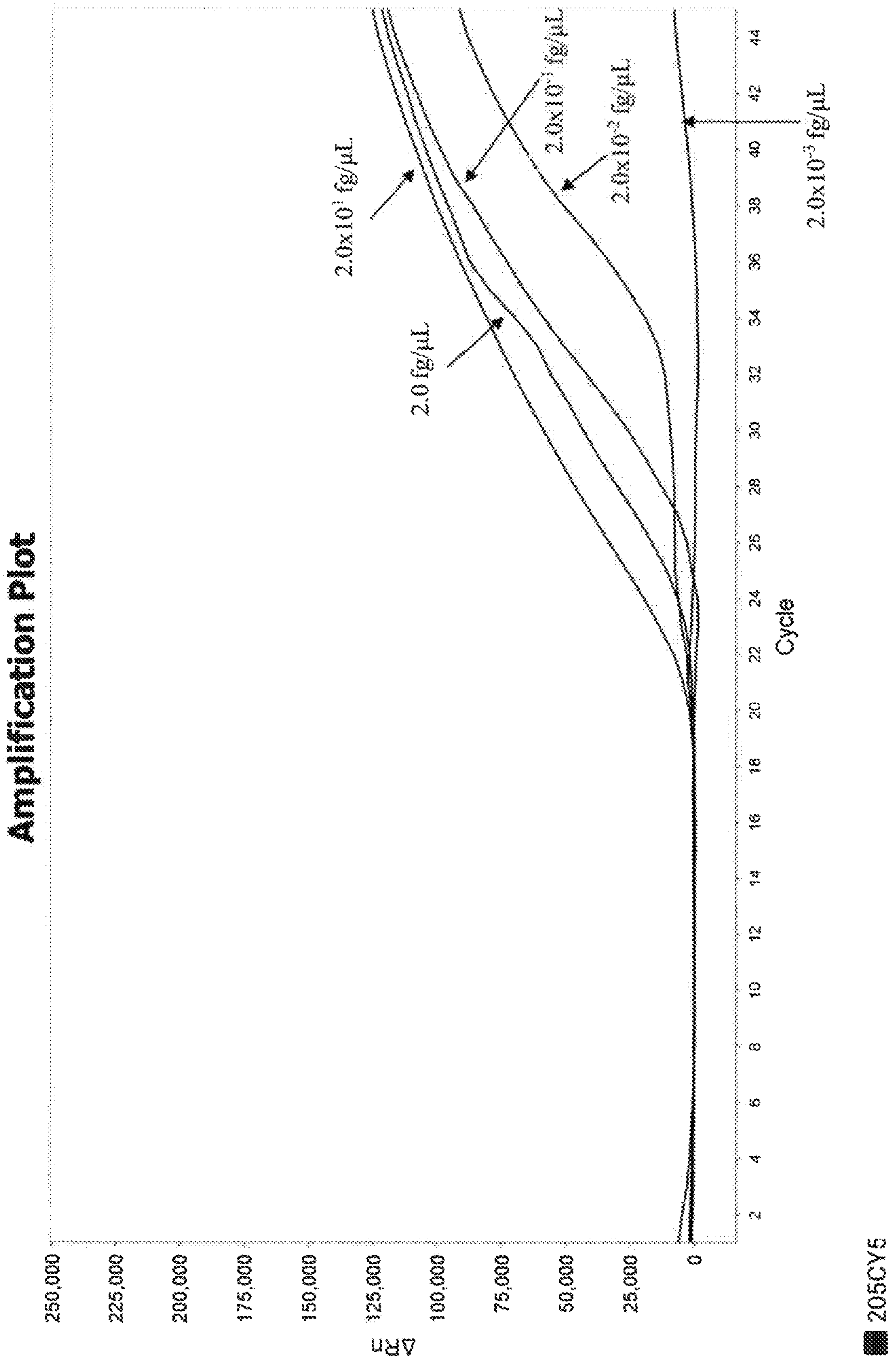
Figure 8D:
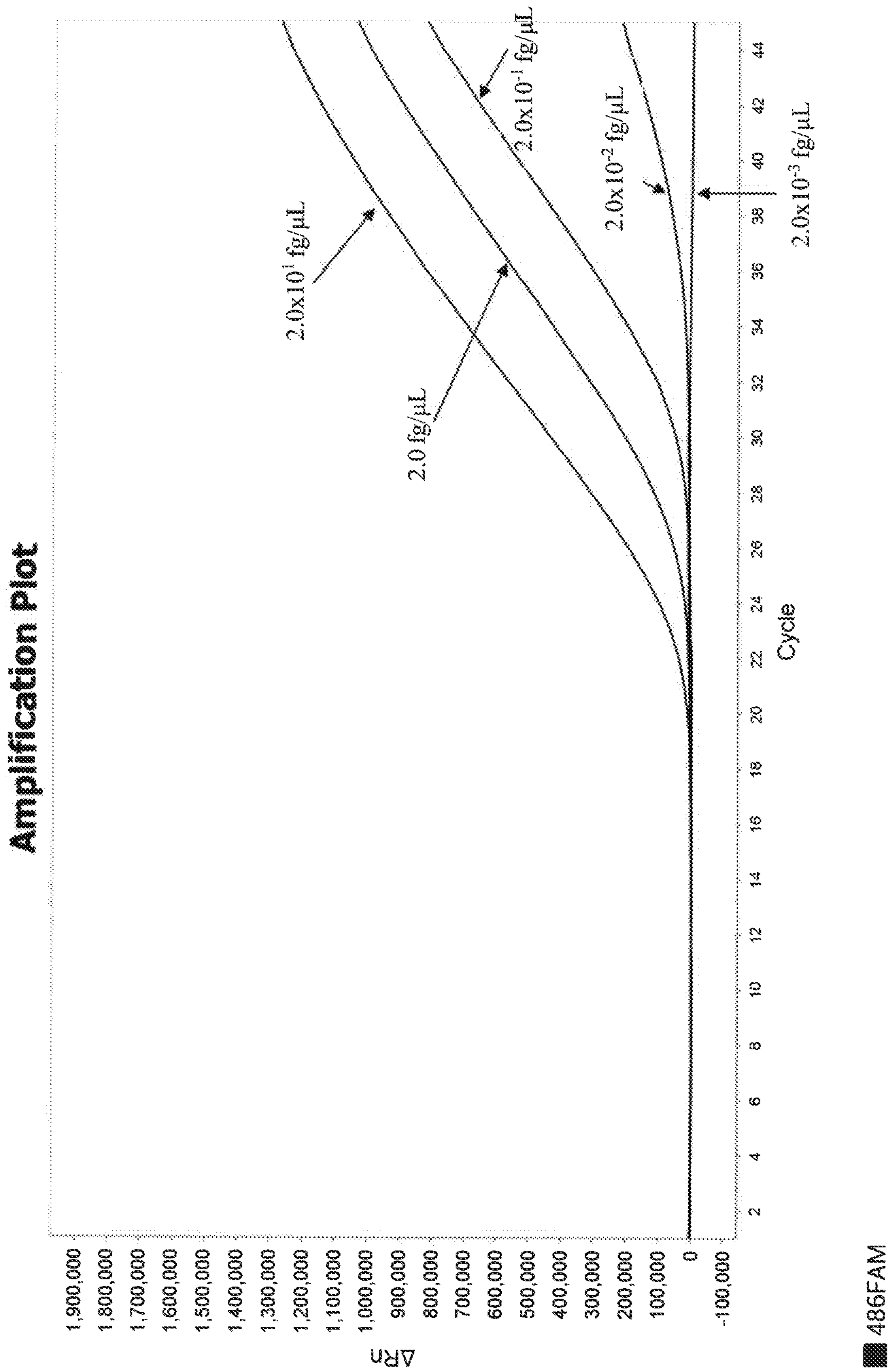

The best forward/reverse primers and probes combination from the experimental results mentioned above was selected, and the singleplex RT-qPCR and the multiplex RT-qPCR for serum miRNA samples was separately performed according to the reaction system and the thermal cycle(s) mentioned above. The results are shown in the FIGS. 5A-F. There was no significant difference in amplification curves and Ct values between the singleplex and multiplex RT-qPCR, as shown particularly in FIG. 5F.

Stability Test of the Multiplex RT-qPCT

Stability test was performed by expanding the sample size to 20 individuals, and the results are shown in Table 12. It is concluded from the result that the multiplex stem-loop reverse transcription primers in this embodiment can accurately detect miR-34c-5p, miR-9-3p, miR-16-5p, and miR-9-5p in the human serum samples collected.

TABLE 12

Ct value for the target miRNAs using singleplex/multiplex RT-qPCR in 20 individuals

| Sample No. | miR-9-3p (Singleplex) | miR-9-3p (Multiplex) | miR-9-5p (Singleplex) | miR-9-5p (Multiplex) | miR-34C-5p (Singleplex) | miR-34C-5p (Multiplex) | miR-16-5p (Singleplex) | miR-16-5p (Multiplex) |
|---|---|---|---|---|---|---|---|---|
| 1 | 23.626 | 23.794 | 23.618 | 23.727 | 23.618 | 23.727 | 23.618 | 23.727 |
| 2 | 23.618 | 23.727 | 31.567 | 31.334 | 31.567 | 31.334 | 29.695 | 31.334 |
| 3 | 23.085 | 23.702 | 30.9 | 31.545 | 30.79 | 31.645 | 29.67 | 29.335 |
| 4 | 31.306 | 31.832 | 31.285 | 31.165 | 30.58 | 31.64 | 29.655 | 29.585 |
| 5 | 31.42 | 31.31 | 32.005 | 31.58 | 31.08 | 31.895 | 29.945 | 30.01 |
| 6 | 23.618 | 23.727 | 32.145 | 30.495 | 31.18 | 31.935 | 29.835 | 30.135 |
| 7 | 31.567 | 31.334 | 31.35 | 31.235 | 31.09 | 31.925 | 29.99 | 29.605 |
| 8 | 31.2 | 30.9 | 32.39 | 32.145 | 31.3 | 31.525 | 29.83 | 29.93 |
| 9 | 29.45 | 29.335 | 30.15 | 30.135 | 31.46 | 31.055 | 31.05 | 31.08 |
| 10 | 32.04 | 31.645 | 32.06 | 31.935 | 30.94 | 31.175 | 29.79 | 29.93 |
| 11 | 31.43 | 31.285 | 31.26 | 31.35 | 31.33 | 31.525 | 31.3 | 31.175 |
| 12 | 29.73 | 29.585 | 29.67 | 29.605 | 31.11 | 31.165 | 26.167 | 26.04 |
| 13 | 32.04 | 31.64 | 31.96 | 31.925 | 29.73 | 29.67 | 25.042 | 25.364 |
| 14 | 32.14 | 32.005 | 31.71 | 31.545 | 31.12 | 31.18 | 25.374 | 25.991 |
| 15 | 29.9 | 30.01 | 29.72 | 29.695 | 31.76 | 31.58 | 24.178 | 26.04 |
| 16 | 32.39 | 31.895 | 31.1 | 31.235 | 29.6 | 29.655 | 23.384 | 25.364 |
| 17 | 31.04 | 30.94 | 29.67 | 29.835 | 31.15 | 31.09 | 22.14 | 25.991 |
| 18 | 30.64 | 30.58 | 31.09 | 31.46 | 30.52 | 30.495 | 24.444 | 22.809 |
| 19 | 29.83 | 29.83 | 30.79 | 30.79 | 29.81 | 29.945 | 23.195 | 21.262 |
| 20 | 31.47 | 31.055 | 29.7 | 29.99 | 31.42 | 31.3 | 24.153 | 23.989 |
| Mean | 29.577 | 29.5065 | 30.707 | 30.6363 | 30.5577 | 30.7730 | 27.1227 | 27.4348 |

Example 2—Multiplex Stem-Loop Reverse Transcription Primers Quantifying Hsa-miR-210-3p, Hsa-miR-126-3p, Hsa-miR-205-5p, and Hsa-miR-486-5p In one embodiment, the method of the present invention screens the stem-loop reverse transcription primer combination for detection multiple target miRNAs including hsa-miR-210-3p, hsa-miR-126-3p, hsa-miR-205-5p, and hsa-miR-486-5p. The sequences of these target miRNAs and other miRNAs mentioned in this article are reported in the microRNA database www.mirbase.org. Specifically, the sequence of hsa-miR-210-3p is shown as SEQ ID No. 29, the sequence of hsa-miR-126-3p is shown as SEQ ID No. 30, the sequence of hsa-miR-205-5p is shown as SEQ ID No. 31, and the sequence of hsa-miR-486-5p is shown as SEQ ID No. 32.

Multiple stem-loop reverse transcription primers each with different anchor sequence lengths (6/8/11 nt) were designed for each of the above target miRNAs. The length of each of the stem-loop reverse transcription primers is about 40-60 nucleotides. From its 5' to its 3' end, each of the stem-loop reverse transcription primers has a stem-loop sequence and an anchor sequence, sequentially. In one embodiment, the stem-loop structures of all of the stem-loop reverse transcription primers have the same sequence, while the anchor sequence of each of the stem-loop reverse transcription primers is complementary to a 3' sequence of each of the target miRNAs, with a selected length ranges between 3-12 nt. The sequences of the stem-loop reverse transcription primers in the Example 2 are shown in Table 13.

TABLE 13

Sequences of stem-loop reverse transcription primers for quantifying the multiple target miRNAs including hsa-miR-210-3p, hsa-miR-126-3p, hsa-miR-205-5p, and hsa-miR-486-5p

| miRNA | Name of the stem-loop reverse transcription primer | Sequence | Anchor sequence Length/nt |
|---|---|---|---|
| hsa-miR-210-3p | miR-210-3p-RT11 | SEQ ID NO. 51 | 11 |
| | miR-210-3p-RT8 | SEQ ID NO. 33 | 8 |
| | miR-210-3p-RT6 | SEQ ID NO. 52 | 6 |
| | miR-210-3p-RT4 | SEQ ID NO. 53 | 4 |
| hsa-miR-126-3p | miR-126-3p-RT11 | SEQ ID NO. 54 | 11 |
| | miR-126-3p-RT6 | SEQ ID NO. 34 | 6 |
| | miR-126-3p-RT4 | SEQ ID NO. 55 | 4 |
| hsa-miR-205-5p | miR-205-5p-RT11 | SEQ ID NO. 56 | 11 |
| | miR-205-5p-RT8 | SEQ ID NO. 57 | 8 |
| | miR-205-5p-RT6 | SEQ ID NO. 35 | 6 |
| | miR-205-5p-RT4 | SEQ ID NO. 58 | 4 |
| hsa-miR-486-5p | miR-486-5p-RT11 | SEQ ID NO. 59 | 11 |
| | miR-486-5p-RT8 | SEQ ID NO. 36 | 8 |
| | miR-486-5p-RT6 | SEQ ID NO. 60 | 6 |
| | miR-486-5p-RT4 | SEQ ID NO. 61 | 4 |

In this embodiment, the stem-loop sequences of all the stem-loop reverse transcription primers are the same and is shown as SEQ ID No. 37.

The forward and reverse primers for the reverse transcription products including cDNA were designed for the multiplex qPCR. From its 5' to 3' end, the forward primer has a $T_m$-enhancing tail and a specific complementary binding sequence, sequentially. The $T_m$-enhancing tail comprises randomly arranged A, T, C, or G to increase its $T_m$ value. The specific binding sequence has a 8-12 nucleotide sequence, and is the same as a DNA equivalent of a 5' sequence of the target miRNA. The DNA equivalent of a target miRNA has the same sequence of the target miRNA while replacing any U in the target miRNA with a T. The length of the forward primer is about 15-22 nucleotides.

The sequence of the reverse primer is the same to a portion of the stem-loop sequence of the stem-loop reverse transcription primer. In this embodiment, the reverse primer is a universal primer. In one embodiment, the universal reverse primer is located on the stem-loop sequence which has about 16-25 nucleotides, while the length of the reverse primer ranges from 15-22 nucleotides. In one embodiment, the universal primer has a sequence same as a portion of the "loop" in the stem-loop sequence. The sequences of the primers are shown in Table 14.

TABLE 14

The forward and reverse primers for cDNA produced in the reverse transcription of the multiple target miRNAs including hsa-miR-210-3p, hsa-miR-126-3p, hsa-miR-205-5p, and hsa-miR-486-5p

| miRNA | Primer | Sequence |
|---|---|---|
| hsa-miR-210-3p | Forward primer | SEQ ID NO. 42 |
| hsa-miR-126-3p | Forward primer | SEQ ID NO. 43 |
| hsa-miR-205-5p | Forward primer | SEQ ID NO. 44 |
| hsa-miR-486-5p | Forward primer | SEQ ID NO. 45 |
| | Universal reverse primer | SEQ ID No. 50 |

The sequence of each of the probes is partially identical to a portion of the DNA equivalent of each of the target miRNAs to be detected. Each of the specific probe contains 12-25 nucleotides, with a quencher group MGB labeled at the 3' end and a fluorescent reporter group labeled at the 5' end. Different fluorescent groups, such as FAM™, VIC®, CY5®, or ROX™, are used to label probes targeting different target miRNAs. In this embodiment, an MGB probe is used as a quencher group. The MGB group labeled at the 3' end of the MGB probe has a quenching effect on fluorescence of the reporter group and can increase the $T_m$ value of the probe itself. This enables the probe to bind preferentially and selectively to the groove of the double-stranded DNA molecule, forming a stable hybrid complex. This further improves the specificity of the detection method. The structure and sequence of each of the probes is shown in Table 15.

TABLE 15

Structure of the probes used in the multiplex qPCR for detection of the multiple target miRNAs including hsa-miR-210-3p, hsa-miR-126-3p, hsa-miR-205-5p, and hsa-miR-486-5p

| miRNA | Probe | Sequence | Fluoro-phore | Quencher group |
|---|---|---|---|---|
| hsa-miR-210-3p | miR-210-3p-VIC | SEQ ID NO. 46 | VIC® | MGB |
| hsa-miR-126-3p | miR-126-3p-ROX | SEQ ID NO. 47 | ROX™ | MGB |
| hsa-miR-205-5p | miR-205-5p-CY5 | SEQ ID NO. 48 | CY5® | MGB |
| hsa-miR-486-5p | miR-486-5p-FAM | SEQ ID NO. 49 | FAM™ | MGB |

Specificity Test of Primers and Probes Using the Target miRNA Template and $ddH_2O$ Singleplex reverse transcription was performed for each of the target miRNAs using its corresponding stem-loop reverse transcription primer. The reverse transcription system is shown in Table 16.

TABLE 16

Systems for the singleplex reverse transcription for each of the target miRNAs

| Reagent | 20 μL system |
|---|---|
| 10X RT MIX | 2 μL |
| HiScript II Enzyme Mix | 2 μL |
| RNA synthesis template/water | 10 pg-1 μg |
| Stem-loop reverse transcription primer (2 μM) | 0.5 μL |
| $ddH_2O$ | To 20 μL |

The reverse transcription thermal cycle is shown in Table 17:

TABLE 17

| Thermal cycle for reverse transcription | | |
|---|---|---|
| Cycle | Temperature | Time |
| 1 | 25° C. | 5 min |
| 1 | 50° C. | 15 min |
| 1 | 85° C. | 5 min |

The reverse transcription products produced in each of the singleplex reverse transcription undergo the multiplex qPCR, separately. The designed forward/reverse primers and probes for each of the target miRNAs were used in the multiplex qPCR. The multiplex qPCR amplification system is shown in Table 18:

TABLE 18

| Multiplex qPCR amplification system | |
|---|---|
| Reagent | 20 μL system |
| Reverse transcription product | 2 μL μL |
| 2X Taq Pro HS U Probe Master Mix | 10 μL |
| MGB probe (10 μM) | 0.2 μL |
| Forward primer (10 μM) | 0.4 μL |
| Universal reverse primer (10 μM) | 0.4 μL |
| $ddH_2O$ | To 20 μL |

The qPCR thermal cycles are shown in Table 19:

TABLE 19

| The qPCR thermal cycles | | |
|---|---|---|
| Cycle | Temperature | Time |
| 1X | 37° C. | 2 min |
| | 95° C. | 30 s |
| 45X | 95° C. | 10 s |
| | 60° C. | 30 s |

The results of the multiplex qPCR are shown in FIGS. 6A-H. Each of the multiple target miRNAs undergoes the singleplex reverse transcription with a stem-loop reverse transcription primer having a specific length for its anchor sequence, and the anchor sequence length of each stem-loop reverse transcription primer may be different from the others. Specificity and sensitivity tests of each of the stem-loop reverse transcription primers are accomplished. According to FIGS. 6A and 6B, miR-210-3p can be detected using the reverse transcription primers with the anchor sequence of 6/8 nt. According to FIGS. 6C and 6D, miR-126-3p can be detected using the reverse transcription primers with the anchor sequences of Apr. 6, 2011 nt. According to FIGS. 5E and 5F, miR-205-5p can be detected using the reverse transcription primers with the anchor sequences of 4/6 nt. According to FIGS. 5G and 5F, miR-486-5p can be detected using the reverse transcription primers with the anchor sequences of 4/8 nt.

Construction of the miRNA Multiplex System

Each of the stem-loop reverse transcription primers is selected for each of the target miRNAs. The length of the anchor sequence of each of the stem-loop reverse transcription primers can be adjusted so as to form more than one possible combinations of the stem-loop reverse transcription primers. In one embodiment, the stem-loop sequences of all the stem-loop reverse transcription primers are the same. In another embodiment, the stem-loop sequence of each of the stem-loop reverse transcription primers is different from the others. Multi-specificity and sensitivity are tested for each combination of the stem-loop reverse transcription primers. When a combination passes the specificity test, it is considered a potential combination for the multiplex RT-qPCR quantifying the multiple target miRNAs. Sensitivity test can be done thereafter to determine the detection limit for the target miRNAs. In order to increase the efficiency of screening, the selection of stem-loop reverse transcription primers can stop once the multi-specificity for a particular combination was confirmed. This combination is then used for the multiplex RT-qPCR detection of the target miRNAs combination. To obtain an optimized stem-loop reverse transcription primer combination, the lengths of anchor sequences of the stem-loop reverse transcription primers are adjusted and more combinations with different anchor sequence lengths are formed. Multi-specificity and sensitivity tests are accomplished for these combinations with different anchor sequences, such that an optimized combination of primers with the best specificity and sensitivity can be obtained.

In the embodiments of Example 2, miR-210-3p was detected using a reverse transcription primer having an anchor sequence of 8 nt, miR-126-3p was detected using a reverse transcription primer having an anchor sequence of 6 nt, miR-205-5p was detected using a reverse transcription primer having an anchor sequence of 6 nt, and miR-486-5p was detected using a reverse transcription primer having an anchor sequence of 8 nt. These were combined to form a stem-loop reverse transcription primer combination, as shown in Table 20.

TABLE 20

| Stem-loop reverse transcription primer combination for detection of miR-210-3p, miR-126-3p, miR-205-5p, miR-486-5p. | | | | |
|---|---|---|---|---|
| miRNA | Stem-loop reverse transcription primer | Primer Sequence | Stem-loop sequence | Anchor Sequence |
| miR-210-3p | miR-210-3p-RT8 | SEQ ID No. 33 | SEQ ID No. 37 | TCAGCCGC SEQ ID No. 38 |
| miR-126-3p | miR-126-3p-RT6 | SEQ ID No. 34 | SEQ ID No. 37 | CGCATT SEQ ID No. 39 |

TABLE 20-continued

| Stem-loop reverse transcription primer combination for detection of miR-210-3p, miR-126-3p, miR-205-5p, miR-486-5p. | | | | |
|---|---|---|---|---|
| miRNA | Stem-loop reverse transcription primer | Primer Sequence | Stem-loop sequence | Anchor Sequence |
| miR-205-5p | miR-205-5p-RT6 | SEQ ID No. 35 | SEQ ID No. 37 | CAGACT SEQ ID No. 40 |
| miR-486-5p | miR-486-5p-RT8 | SEQ ID No. 36 | SEQ ID No. 37 | CTCGGGGC SEQ ID No. 41 |

This combination of the stem-loop reverse transcription primers was set as an example for the multi-specificity, sensitivity and stability tests.

Multi-Specificity Test of the Stem-Loop Reverse Transcription Primer Combination Each stem-loop reverse transcription primer in the combination was used in the singleplex RT of the mixed target miRNAs template (miR-210-3p, miR-126-3p, miR-205-5p and miR-486-5p). Each of the singleplex RT system is shown in Table 21:

TABLE 21

| Singleplex RT system | |
|---|---|
| Reagent | 20 μL system |
| 10X RT MIX | 2 μL |
| HiScript II Enzyme Mix | 2 μL |
| Mixed RNA template | 10 pg-1 μL |
| Stem-loop reverse transcription primer (2M) | 0.5 μL |
| ddH2O | To 20 μL |

The reverse transcription products obtained from the singleplex RT were subjected to the multiplex-qPCR to determine whether there existed any cross-reaction in the quantification of the four target miRNAs, so as to verify the multi-specificity of the stem-loop reverse transcription primer combination. The qPCR system is shown in Table 22:

TABLE 22

| qPCR system | |
|---|---|
| Reagent | 20 μL system |
| Reverse transcription product | 2 μL |
| 2X Taq Pro HS U Probe Master Mix | 10 μL |
| TaqMan® probe combination (10 μM) | 0.2 μL |
| Forward primer combination (10 μM) | 0.4 μL |
| Universal reverse primer (10 μM) | 0.4 μL |
| $ddH_2O$ | To 20 μL |

Among them, the forward primers and reverse primer combination are the combinations of the four forward primers and one universal reverse primer as shown in Table 14, while the probes combination is the combination of the four probes as shown in Table 3. As shown in FIGS. 7A-D, there was no cross-reaction in the quantification of each of the target miRNAs, and the stem-loop reverse transcription primers, forward/reverse primers, and probes all showed good multi-specificity. Therefore, this combination can be used for the multiplex RT-qPCR detection of the four target miRNAs, namely, miR-210-3p, miR-126-3p, miR-205-5p, and miR-486-5p.

Based on the multi-specificity of the stem-loop reverse transcription primer combination detecting the four target miRNAs, any two or three of the stem-loop reverse transcription primers can form a sub-combination which has the multi-specificity for detection of two or three of the target miRNAs, respectively.

Sensitivity Test for the Screened Stem-Loop Reverse Transcription Primer Combination To test the sensitivity of the screened stem-loop reverse transcription primer combination, the mixed target miRNA template (miR-210-3p, miR-126-3p, miR-205-5p, miR-486-5p) are made into gradient dilution. Each template having a different concentration of the mixed target miRNA template undergoes the multiplex RT and then the multiplex qPCR using the screened stem-loop reverse transcription primer combination to determine the lowest detection limit, i.e., sensitivity.

Specifically, the target miRNAs template at a concentration of $2.0\times10^{3}$ fg/μL was diluted in 10-fold gradient to $2.0\times10^{1}$ fg/μL, $2.0\times10^{0}$ fg/L, $2.0\times10^{-1}$ fg/μL, $2.0\times10^{-2}$ fg/μL, and $2.0\times10^{-3}$ fg/μL, and then subjected to the multiplex RT-qPCR amplification of all obtained reverse transcription products.

The results are shown in FIGS. 8A-D. The detection limit for miR-210-3p, miR-126-3p, miR-205-5p, and miR-486-5p were $2.0\times10^{-2}$ fg/μL.

Comparison of the Singleplex and Multiplex RT-qPCR of the Target miRNAs

Total RNA, including miRNA, were extracted from individuals using MolPure® Serum/Plasma miRNA Kit (Yeasen, Shanghai China).

Figure 9:
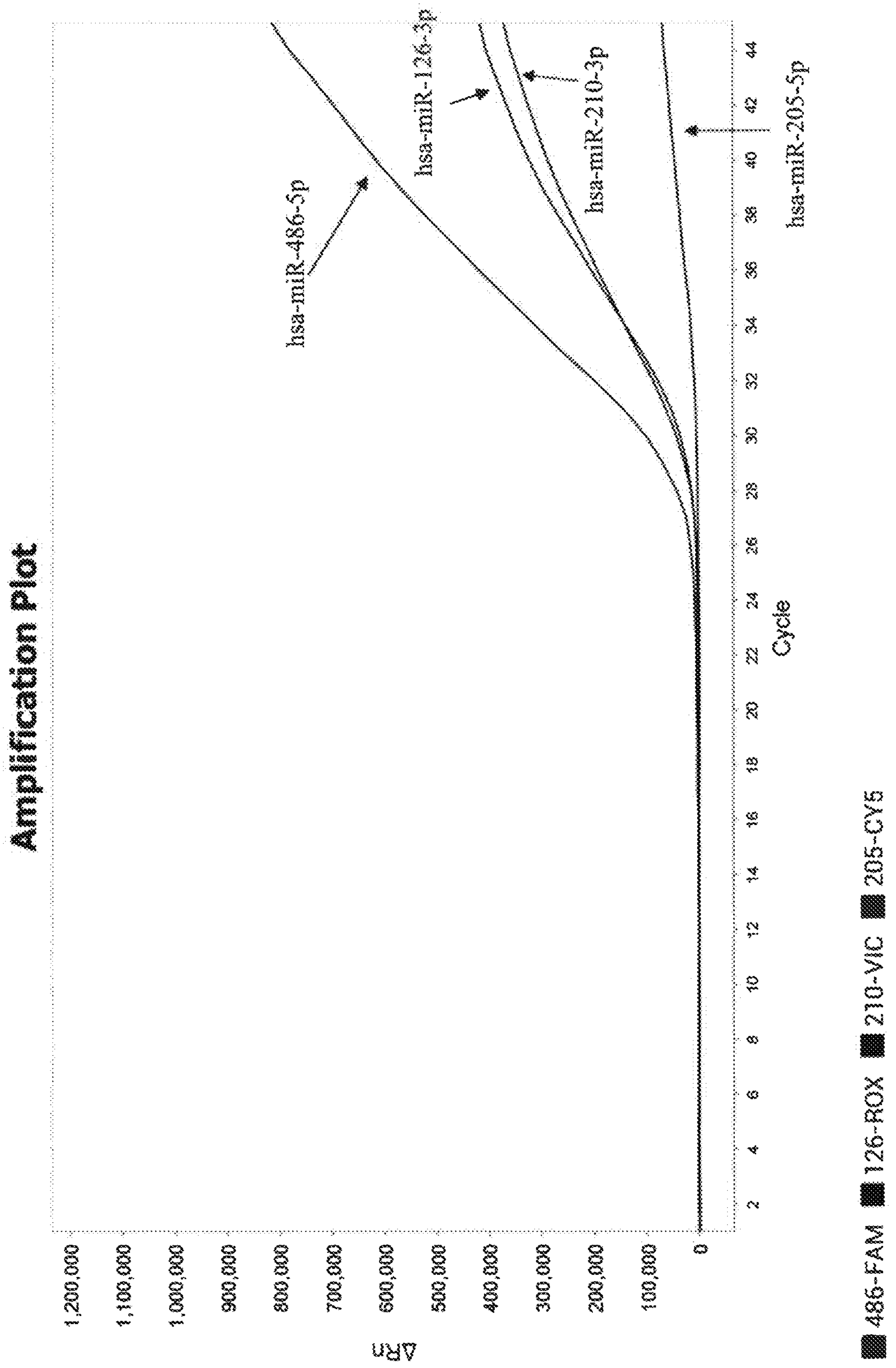
FIG. 9 is a schematic diagram showing multiplex detection of the target miRNA combination of hsa-miR-210-3p; hsa-miR-126-3p, hsa-miR-205-5p, and hsa-miR-486-5p by multiplex RT-qPCR using the screened multiplex stem-loop reverse transcription primers.

Using the best forward/reverse primers combination and probes combination discovered in the Example 2, and using the qPCR system presented above to accomplish the multiplex RT-qPCR for the target miRNAs in the total RNA sample, and the result is shown in FIG. 9.

In particular, the screened stem-loop reverse transcription primer combination for miR-210-3p, miR-126-3p, miR-205-5p, miR-486-5p has promising multi-specificity and sensitivity so as to correctly quantifying the target miRNAs through the multiplex RT-qPCR.

Optimization of Multiplex RT-qPCR by Adjusting the Anchor Sequences' Lengths

A mixed target miRNAs template including hsa-miR-210-3p, hsa-miR-126-3p, hsa-miR-205-5p, and hsa-miR-486-5p was used. Each of the target miRNAs to be quantified was separately subjected to the multiplex RT with the combinations of the stem-loop reverse transcription primers with different anchor sequence lengths shown in Table 23; then the multiplex reverse transcription products were subjected to the multiplex qPCR to screen a combination with good sensitivity and specificity.

TABLE 23

| Groups of combination of the stem-loop reverse transcription primers with varied anchor sequence lengths | | | | |
|---|---|---|---|---|
| Group | Combination of the stem-loop reverse transcription primers | | | |
| Group 1 | miR-210-3p-RT6 | miR-126-3p-RT4 | miR-205-5p-RT4 | miR-486-5p-RT4 |
| Group 2 | miR-210-3p-RT6 | miR-126-3p-RT6 | miR-205-5p-RT6 | miR-486-5p-RT8 |
| Group 3 | miR-210-3p-RT8 | miR-126-3p-RT4 | miR-205-5p-RT6 | miR-486-5p-RT8 |
| Group 4 | miR-210-3p-RT8 | miR-126-3p-RT6 | miR-205-5p-RT4 | miR-486-5p-RT8 |
| Group 5 | miR-210-3p-RT8 | miR-126-3p-RT6 | miR-205-5p-RT6 | miR-486-5p-RT4 |
| Group 6 | miR-210-3p-RT8 | miR-126-3p-RT6 | miR-205-5p-RT6 | miR-486-5p-RT8 |

Figure 10A:
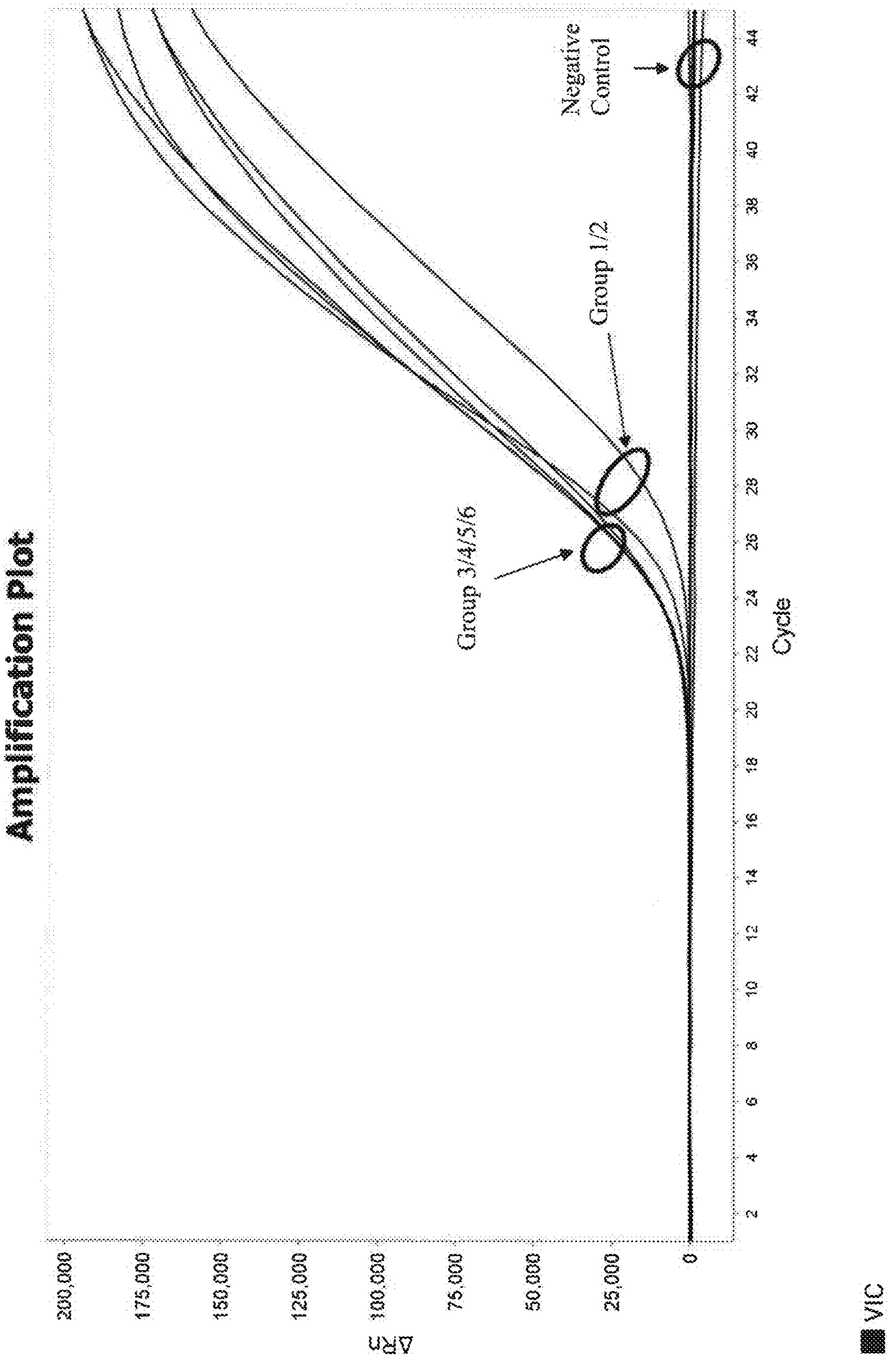
FIGS. 10A-D show amplification plots of quadruplex RT-qPCR of a mixed target miRNAs template using the stem-loop reverse transcription primer combination according to Table 23.
Figure 10B:
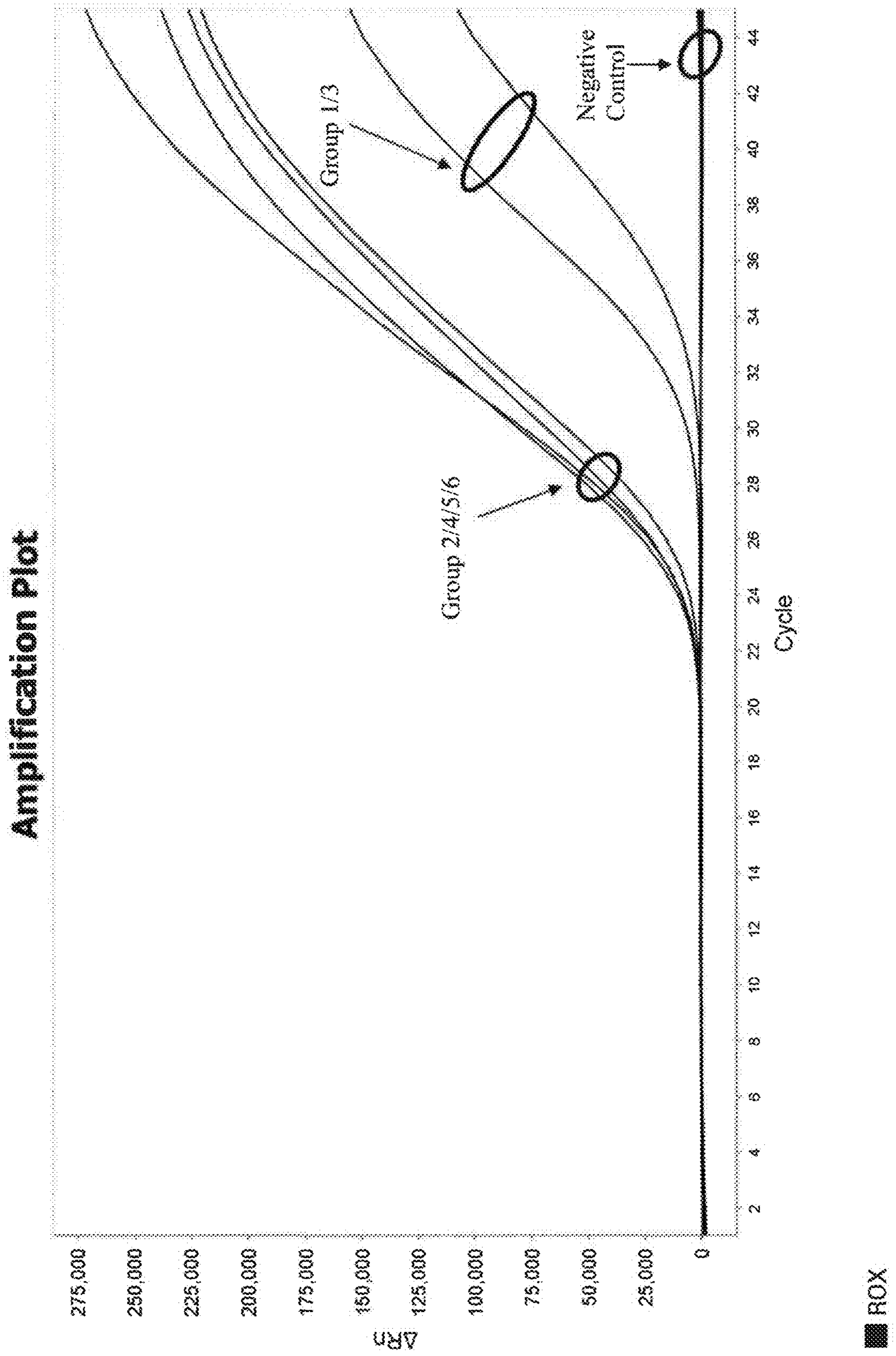
Figure 10C:
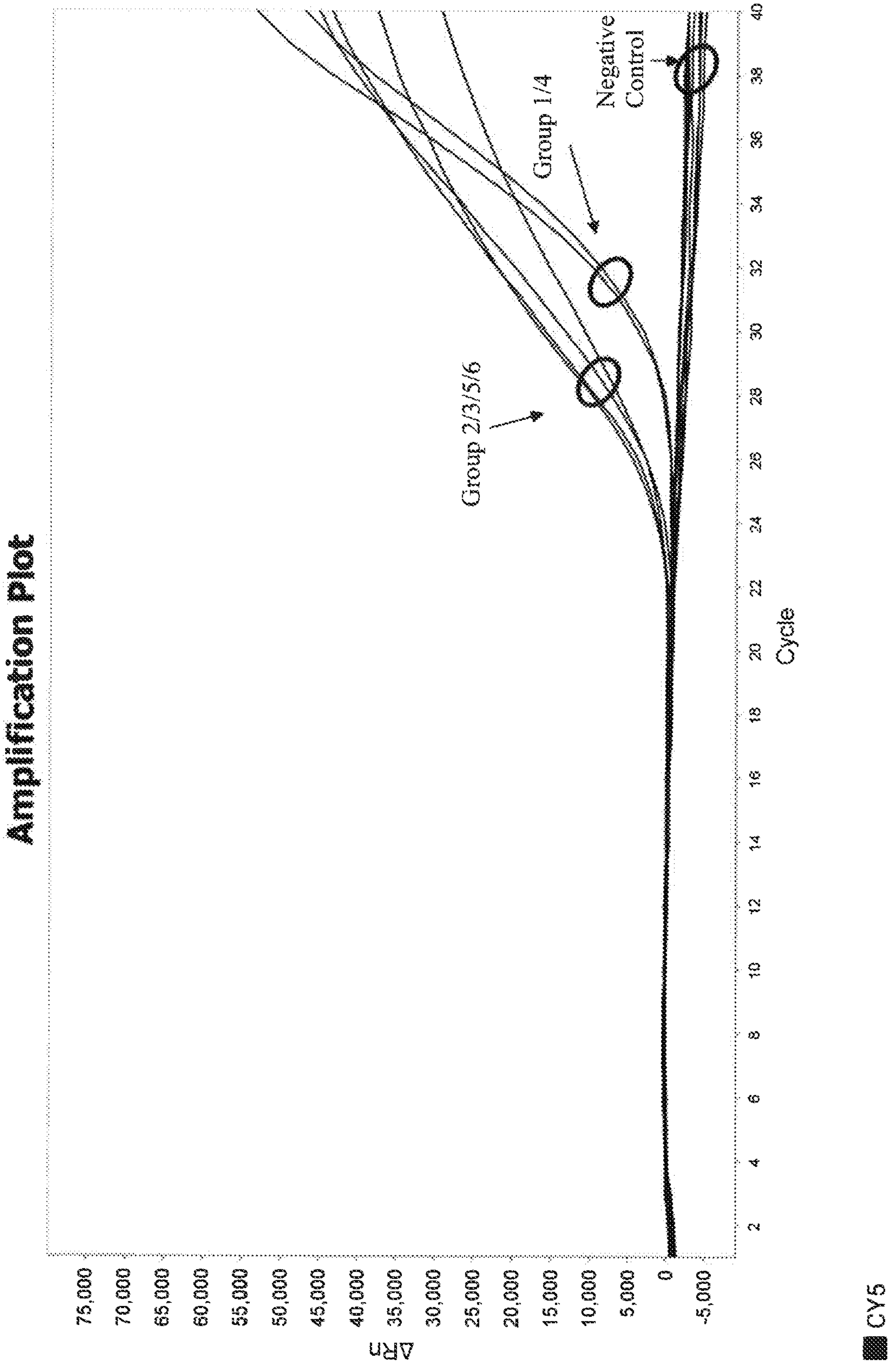
Figure 10D:
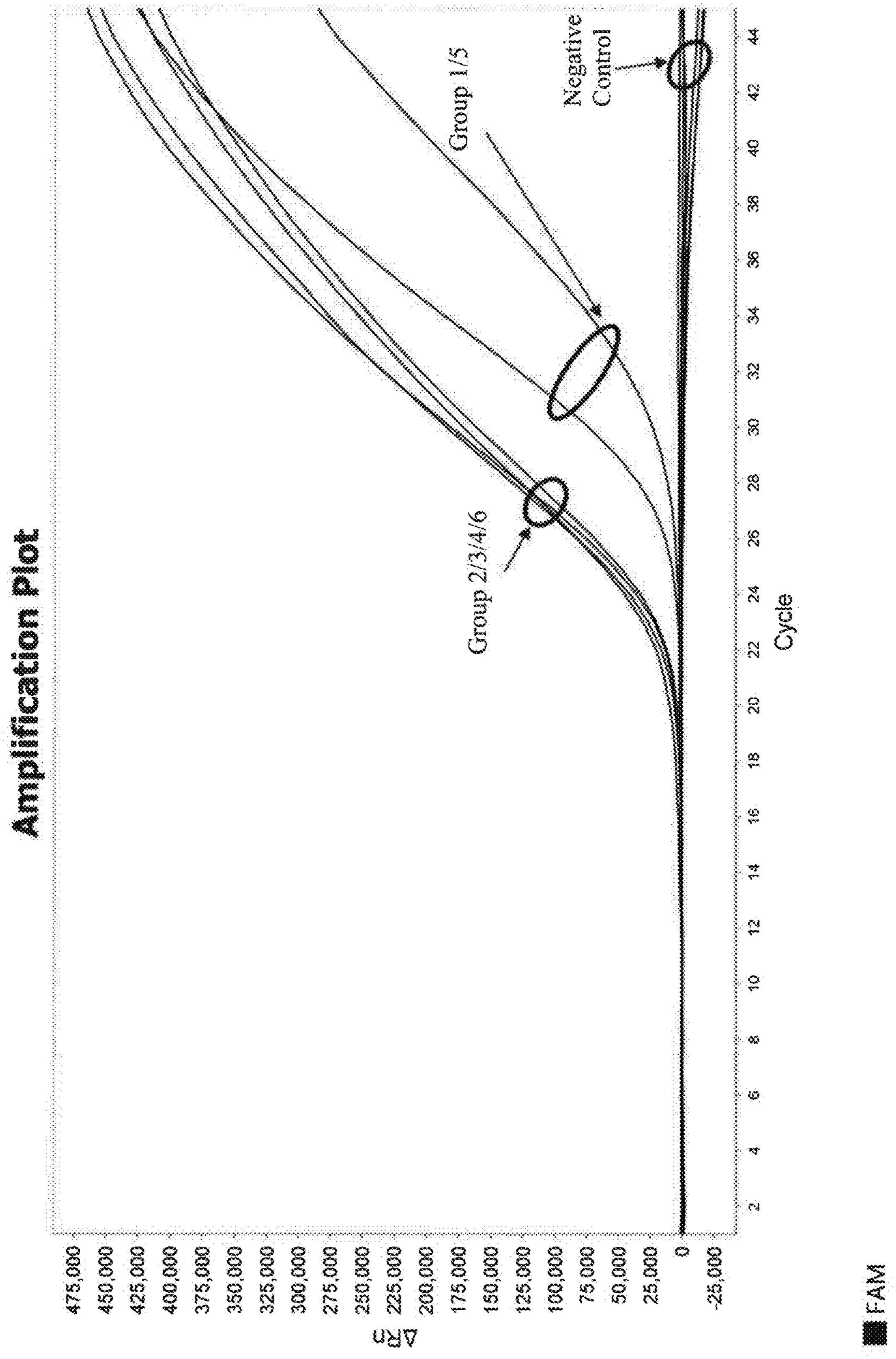

FIGS. 10A-D show amplification plots of the multiplex RT-qPCR of a mixed target miRNAs template using the stem-loop reverse transcription primer combination according to Table 23, so as to optimize the anchor sequence lengths for each of the stem-loop reverse transcription primers. FIG. 10A shows the qPCR result using fluorescent reporter group VIC®. FIG. 10B shows the qPCR result using fluorescent reporter group ROX™ FIG. 10C shows the qPCR result using fluorescent reporter group CY5®. FIG. 10D shows the qPCR result using fluorescent reporter group FAM™.

According to FIGS. 10A-D and Table 23, the group 6 demonstrated the best multi-specificity and sensitivity by showing the lowest or relative low Ct value for each of the target miRNAs. Thus, the stem-loop reverse transcription primer with 8 nt anchor sequence length is selected for miR-210-3p. The stem-loop reverse transcription primer with 6 nt anchor sequence length is selected for miR-126-3p. The stem-loop reverse transcription primer with 6 nt anchor sequence length is selected for miR-205-5p. The stem-loop reverse transcription primer with 8 nt anchor sequence length is selected for miR-486-5p.

Any two or three of hsa-miR-210-3p, hsa-miR-126-3p, hsa-miR-205-5p and hsa-miR-486-5p were mixed to form a mixed RNA template, and multiplex reverse transcription was separately performed with the screened combination of stem-loop reverse transcription primers; the multiplex reverse transcription products was then subjected to multiplex qPCR, so as to validate the specificity and sensitivity of the screened combination of stem-loop reverse transcription primers.

To summarize the Example 1, the sequences of the stem-loop reverse transcription primers, forward/reverse primers, and probes for the multiplex RT-qPCR quantification of miR-16-5p, miR-34c-5p, miR-9-3p, and miR-9-5p are listed below in Table 24.

TABLE 24

| Primers and probes used for the multiplex RT-qPCR | | | | | | | |
|---|---|---|---|---|---|---|---|
| Target miRNA | miRNA Seq' (5'-3') | Stem-loop reverse transcription primer (5'-3') | Stem-loop Seq' (5'-3') | Anchor Seq' | Forward primer (5'-3') | Probe (5'-3') | Reverse primer (5'-3') |
| miR-16-5p | UAGCAGCACGUAAAUAUUGGCG (SEQ ID No. 1) | GTCGTATCCAGTGCAGGGTCCGAGGTATTCGCACTGGATACGACCGCCAATA (SEQ ID No. 5) | GTCGTATCCAGTGCAGGGTCCGAGGTATTCGCACTGGATACGAC (SEQ ID No. 9) | CGCCAATA (SEQ ID No. 13) | CGCGCGTCTTTGGTTATCT (SEQ ID No. 17) | VIC-GTGCAGGGTCCGAGGT-BHQ1 (SEQ ID No. 21) | TGGCGGTCGTATCCAGTGCGAA (SEQ ID No. 25 |
| miR-34c-5p | AGGCAGUGUAGUUAGCUGAUUGC (SEQ ID No. 2) | GTCTGTATGGTTGGATAGGGATGTGAACCAGTCGTGAACAACCATACAGACGCAATC (SEQ ID No. 6) | GTCTGTATGGTTGGATAGGGATGTGAACCAGTCGTGAACAACCATACAGAC (SEQ ID No. 10) | GCAATC (SEQ ID No. 14) | GCGCGAGGCAGTGTAGTTA (SEQ ID No. 18) | CY5-TTGGATAGGGATGTGAACCAG-BHQ3 (SEQ ID No. 22) | CTGATTGCGTCTGTATGGTTGTTCACG (SEQ ID No. 26) |
| miR-9-3p | AUAAAGCUAGAUAACCGAAAGU (SEQ ID No. 3) | GTTGGCTCTGGTGCAGGGTCCGAGGTATTCGCACCAGAGCCAACACTTTC (SEQ ID ) No. 7 | GTTGGCTCTGGTGCAGGGTCCGAGGTATTCGCACCAGAGCCAAC (SEQ ID No. 11) | ACTTTC (SEQ ID No. 15) | TTGCGCGCATAAAGCTAGAT (SEQ ID No. 19) | ROX-GTGCAGGGTCCGAGGT-BHQ2 (SEQ ID No. 23) | ACCGAAAGTGTTGGCTCTGGTGC (SEQ ID No. 27) |
| miR-9-5p | UCUUUGGUUAUCUAGCUGUAUGA (SEQ ID No. 4) | GGTCGTATGCAAAGCAGGGTCCGAGGTATCCATCGCACGCATCGCACTGCATACGACCTCATACAGCTA (SEQ ID No. 8) | GGTCGTATGCAAAGCAGGGTCCGAGGTATCCATCGCACGCATCGCACTGCATACGACC (SEQ ID No. 12) | TCATACAGCTA (SEQ ID No. 16) | CGCGCGTCTTTGGTTATCTAG (SEQ ID No. 20) | FAM-AGCAGGGTCCGAGGTATC-BHQ1 (SEQ ID No. 24) | TGTATGAGGTCGTATGCAGTGCGAT (SEQ ID No. 28) |

To summarize the Example 2, the sequences of the stem-loop reverse transcription primers, forward/reverse primers, and probes for the multiplex RT-qPCR quantification of hsa-miR-210-3p, hsa-miR-126-3p, hsa-miR-205-5p and hsa-miR-486-5p are listed below in Table 25.

TABLE 25

Primers and probes used for multiplex RT-qPCR

| Target miRNA | miRNA Seq' (5'-3') | Stem-loop reverse transcription Seq' (5'-3') | Stem-loop Seq' (5'-3') | Anchor Seq' (5'-3') | Forward Primer (5'-3') | Probe (5'-3') | Reverse primer (5'-3') |
|---|---|---|---|---|---|---|---|
| hsa-miR-210-3p | CUGUGCGUGUGACAGCGGCUGA (SEQ ID No. 29) | GTCGTATCCAGTGCAGGGTCCGAGGTATTCGCACTGGATACGACTCAGCCGC (SEQ ID No. 33) | GTCGTATCCAGTGCAGGGTCCGAGGTATTCGCACTGGATACGAC (SEQ ID No. 37) | TCAGCCGC (SEQ ID No. 38) | ATGCCTGTGCGTGTGAC (SEQ ID No. 42) | VIC-AGCGGCTGAGTCGTAT-MGB (SEQ ID No. 46) | GTGCAGGGTCCGAGGT (SEQ ID No. 50) |
| hsa-miR-126-3p | UCGUACCGUGAGUAAUAAUGCG (SEQ ID No. 30) | GTCGTATCCAGTGCAGGGTCCGAGGTATTCGCACTGGATACGACCGCATT (SEQ ID No. 34) | GTCGTATCCAGTGCAGGGTCCGAGGTATTCGCACTGGATACGAC (SEQ ID No. 37) | CGCATT (SEQ ID No. 39) | TTCGCGCTCGTACCGT(SEQ ID No. 43) | ROX-AGTAATAATGCGGTCGTATCC-MGB (SEQ ID No. 47) | GTGCAGGGTCCGAGGT (SEQ ID No. 50) |
| hsa-miR-205-5p | UCCUUCAUUCCACCGGAGUCUG (SEQ ID No. 31) | GTCGTATCCAGTGCAGGGTCCGAGGTATTCGCACTGGATACGACCAGACT (SEQ ID No. 35) | GTCGTATCCAGTGCAGGGTCCGAGGTATTCGCACTGGATACGAC (SEQ ID No. 37) | CAGACT (SEQ ID No. 40) | TTGCCGCCTCCTTCATTC(SEQ ID No. 44) | CY5-CCGGAGTCTGGTCGTATC-MGB (SEQ ID No. 48) | GTGCAGGGTCCGAGGT (SEQ ID No. 50) |
| hsa-miR-486-5p | UCCUGUACUGAGCUGCCCCGAG (SEQ ID No. 32) | GTCGTATCCAGTGCAGGGTCCGAGGTATTCGCACTGGATACGACCTCGGGGC (SEQ ID No. 36) | GTCGTATCCAGTGCAGGGTCCGAGGTATTCGCACTGGATACGAC (SEQ ID No. 37) | CTCGGGGC (SEQ ID No. 41) | GCCGCCTCCTGTACTGA (SEQ ID No. 45) | FAM-TGCCCCGAGGTCGTATC-MGB (SEQ ID No. 49) | GTGCAGGGTCCGAGGT (SEQ ID No. 50) |

The stem-loop reverse transcription primers with different anchor lengths are listed in Tables 26 and 27.

TABLE 26

Stem-loop primer variants with different anchor lengths for miR-16-5p, miR-34c-5p, miR-9-3p, and miR-9-5p

| Anchor Seq' Length | Stem-loop primer for miR-16-5p | Stem-loop primer for miR-34c-5p | Stem-loop primer for miR-9-3p | Stem-loop primer for miR-9-5p |
|---|---|---|---|---|
| 11 nt | GTCGTATCCAGTGCAGGGTCCGAGGTATTCGCACTGGATACGACCGCCAATATTT (SEQ ID No. 62) | GTCTGTATGGTTGGATAGGGATGTGAACCAGTCGTGAACAACCATACAGACGCAATCAGCTA (SEQ ID No. 64) | GTTGGCTCTGGTGCAGGGTCCGAGGTATTCGCACCAGAGCCAACACTTTCGGTTA (SEQ ID No. 66) | GGTCGTATGCAAAGCAGGGTCCGAGGTATCCATCGCACGCATCGCACTGCATACGACCTCATACAGCTA (SEQ ID No. 8) |
| 8 nt | GTCGTATCCAGTGCAGGGTCCGAGGTATTCGCACTGGATACGACCGCCAATA (SEQ ID No. 5) | GTCTGTATGGTTGGATAGGGATGTGAACCAGTCGTGAACAACCATACAGACGCAATCAG (SEQ ID No. 65) | GTTGGCTCTGGTGCAGGGTCCGAGGTATTCGCACCAGAGCCAACACTTTCGG (SEQ ID No. 67) | GGTCGTATGCAAAGCAGGGTCCGAGGTATCCATCGCACGCATCGCACTGCATACGACCTCATACAG (SEQ ID No. 68) |
| 6 nt | GTCGTATCCAGTGCAGGGTCCGAGGTATTCGCACTGGATACGACCGCCAA (SEQ ID No. 63) | GTCTGTATGGTTGGATAGGGATGTGAACCAGTCGTGAACAACCATACAGACGCAATC (SEQ ID No. 6) | GTTGGCTCTGGTGCAGGGTCCGAGGTATTCGCACCAGAGCCAACACTTTC (SEQ ID No. 7) | GGTCGTATGCAAAGCAGGGTCCGAGGTATCCATCGCACGCATCGCACTGCATACGACCTCATAC (SEQ ID No. 69) |

TABLE 27

Stem-loop primer variants with different anchor lengths for miR-210-3p, miR-126-3p, miR-205-5p, and miR-486-5p

| Anchor Sequence length | Stem-loop primer for hsa-miR-210-3p | Stem-loop primer for hsa-miR-126-3p | Stem-loop primer for hsa-miR-205-5p | Stem-loop primer for hsa-miR-486-5p |
|---|---|---|---|---|
| 11 nt | GTCGTATCCA GTGCAGGGTC CGAGGTATTC GCACTGGATA CGACTCAGCC GCTGT (SEQ ID NO. 51) | GTCGTATCCA GTGCAGGGTC CGAGGTATTC GCACTGGATA CGACCGCATT ATTAC (SEQ ID NO. 54) | GTCGTATCCA GTGCAGGGTC CGAGGTATTC GCACTGGATA CGACCAGACT CCGGT (SEQ ID NO. 56) | GTCGTATCCA GTGCAGGGTC CGAGGTATTC GCACTGGATA CGACCTCGGG GCAGC (SEQ ID NO. 59) |
| 8 nt | GTCGTATCCA GTGCAGGGTC CGAGGTATTC GCACTGGATA CGACTCAGCC GC (SEQ ID NO. 33) | NA | GTCGTATCCA GTGCAGGGTC CGAGGTATTC GCACTGGATA CGACCAGACT CC (SEQ ID NO. 57) | GTCGTATCCA GTGCAGGGTC CGAGGTATTC GCACTGGATA CGACCTCGGG GC (SEQ ID NO. 36) |
| 6 nt | GTCGTATCCA GTGCAGGGTC CGAGGTATTC GCACTGGATA CGACTCAGCC (SEQ ID NO. 52) | GTCGTATCCA GTGCAGGGTC CGAGGTATTC GCACTGGATA CGACCGCATT (SEQ ID NO. 34) | GTCGTATCCA GTGCAGGGTC CGAGGTATTC GCACTGGATA CGACCAGACT (SEQ ID NO. 35) | GTCGTATCCA GTGCAGGGTC CGAGGTATTC GCACTGGATA CGACCTCGGG (SEQ ID NO. 60) |
| 4 nt | GTCGTATCCA GTGCAGGGTC CGAGGTATTC GCACTGGATA CGACTCAG (SEQ ID NO. 53) | GTCGTATCCA GTGCAGGGTC CGAGGTATTC GCACTGGATA CGACCGCA (SEQ ID NO. 55) | GTCGTATCCA GTGCAGGGTC CGAGGTATTC GCACTGGATA CGACCAGA (SEQ ID NO. 58) | GTCGTATCCA GTGCAGGGTC CGAGGTATTC GCACTGGATA CGACCTCG (SEQ ID NO. 61) |

Figure 11:
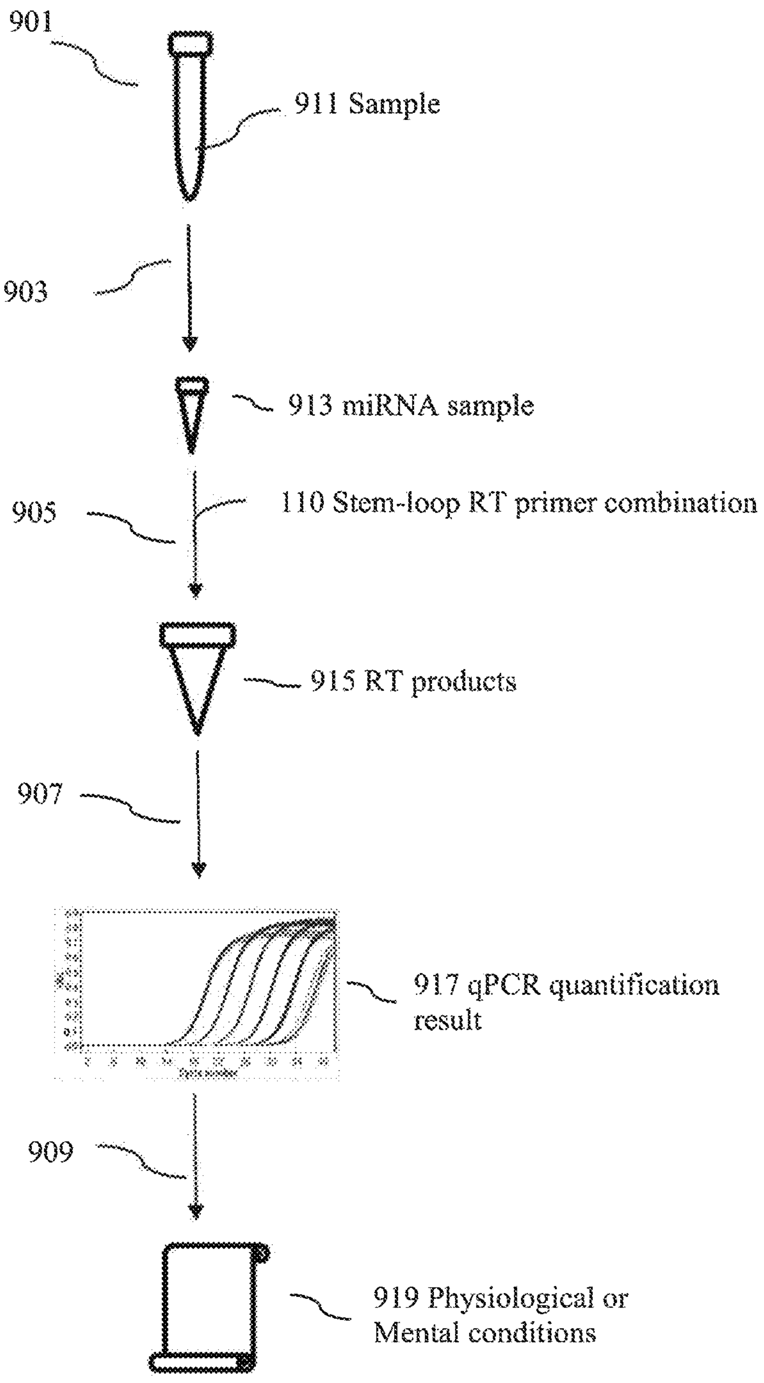
FIG. 11 shows a diagram of multiplex RT-qPCR process for determining a physiological or mental condition of a living subject.

In another embodiment of the invention, as shown in FIG. 11, a multiplex stem-loop reverse transcription primer combination is used for determining a physiological or mental condition of a living subject by quantifying multiple target miRNAs in the living subject. This permits the multiplex stem-loop reverse transcription primer combination to be used in clinical settings such as hospitals for diagnosis of diseases.

First, a biological sample 911 is collected from the living subject in a collection process 901. A miRNA sample 913 having the multiple target miRNAs is extracted 903 from the biological sample 911. A multiplex RT-qPCR 905 is then performed on the miRNA sample 913. In particular, a reverse transcription process 905 is performed on the miRNA sample 913 using the multiplex stem-loop reverse transcription primer combination 110, and a collection of multiplex reverse transcription products 915 is collected. Next, a multiplex qPCR 907 is performed for the collection of reverse transcription products 915 so as to obtain a quantification result for each of the multiple target miRNAs, and a collection of quantification results of the multiple target miRNAs 917 is formed.

The physiological or mental condition 919 of the living subject is determined by comparing the collection of quantification results of the multiple target miRNAs with a set of standard values, e.g. quantification results of the multiple target miRNAs in one or more healthy human individuals.

In one embodiment, the multiple targets miRNAs are selected based on the physiological or mental condition to be determined. In one embodiment, the multiple targets miRNAs have two target miRNAs. In one embodiment, the multiple targets miRNAs have three target miRNAs. In one embodiment, the multiple targets miRNAs have four target miRNAs. In one embodiment, the multiple targets miRNAs have five target miRNAs. In one embodiment, the multiple targets miRNAs have six target miRNAs. In one embodiment, the multiple targets miRNAs have seven target miRNAs. In one embodiment, the multiple targets miRNAs have eight target miRNAs. In one embodiment, the multiple targets miRNAs have nine target miRNAs. In one embodiment, the multiple targets miRNAs have ten target miRNAs.

The foregoing description of illustrative embodiments of the invention has been presented for purposes of illustration and of description. It is not intended to be exhaustive or to limit the invention to the precise form disclosed, and modifications and variations are possible in light of the above teachings or may be acquired from practice of the invention. The embodiments were chosen and described in order to explain the principles of the invention and as practical applications of the invention to enable one skilled in the art to utilize the invention in various embodiments and with various modifications as suited to the particular use contemplated. It is intended that the scope of the invention be defined by the claims appended hereto and their equivalents.

What is claimed is:

1. A method for screening a multiplex stem-loop reverse transcription primer combination demonstrating multi-specificity for quantifying a plurality of target miRNAs simultaneously, the method comprising:

(A) providing the plurality of target miRNAs of a human subject, wherein each of the plurality of target miRNAs associated with the health condition has a unique 3' sequence; wherein each of the plurality of target miRNAs has a length between about 18-25 nt; and the plurality of target miRNAs includes 2-10 target miRNAs;

(B) providing a plurality of stem-loop reverse transcription primers, wherein each of the plurality of stem-loop reverse transcription primers has a stem-loop sequence forming a stem-loop structure and an anchor sequence complimentary to the unique 3' sequence of one of the plurality of target miRNAs, wherein the plurality of stem-loop reverse transcription primers are selected by a selection process comprising:

a) selecting the stem-loop sequence for each of the plurality of stem-loop reverse transcription primers; and b) selecting a certain length for the anchor sequence of each of the plurality of stem-loop reverse transcription primers, wherein the length of the anchor sequence is selected between 3 nt to 12 nt; and wherein the lengths of the anchor sequences of each of the plurality of stem-loop reverse transcription primers is different from the others;

(C) screening the plurality of stem-loop reverse transcription primers by a screening process for determining the multi-specificity of the plurality of stem-loop reverse transcription primers, wherein the screening process comprises:

i) separately performing a process of singleplex reverse transcription for each of the plurality of stem-loop reverse transcription primers using a mixed target miRNAs template comprising the plurality of target miRNAs to be quantified;

ii) separately collecting a collection of reverse transcription products from each of the separate singleplex reverse transcription processes of step i);

iii) separately performing a process of multiplex qPCR amplification for each of the collections of reverse transcription products from step ii) to form a collection of multiplex qPCR products for each of the collections of reverse transcription products;

iv) separately obtaining a quantification result of each of the plurality of target miRNAs based on each of the collections of multiplex qPCR products and obtaining a collection of the quantification results of the plurality of target miRNAs; and v) determining the multi-specificity of the plurality of stem-loop reverse transcription primers based on the collection of quantification results formed in step iv), wherein the multi-specificity of the plurality of stem-loop reverse transcription primers is confirmed when the collection of quantification results shows that each of the plurality of stem-loop reverse transcription primers specifically reverse transcribes the target miRNA to which the anchor sequence of each of the plurality of stem-loop reverse transcription primer is complimentary; and (D) modifying, if the multi-specificity of the plurality of stem-loop reverse transcription primers is not confirmed by the collection of quantification results, the plurality of stem-loop reverse transcription primers by a repeat process comprising:

providing a modified plurality of stem-loop reverse transcription primers by repeating step b) of the selection process to select a new length for the anchor sequence of each of those of the plurality of stem-loop reverse transcription primers which fail to specifically reverse transcribe the target miRNA to which the anchor sequence of each of the plurality of stem-loop reverse transcription primers is complimentary, wherein the length of the anchor sequence is selected between 3 nt to 12 nt; wherein, after the modification, the lengths of the anchor sequences of each of the modified plurality of stem-loop reverse transcription primers is different from the others; and repeating steps i)-v) of the screening process to determine the multi-specificity of the modified plurality of stem-loop reverse transcription primers, until the modified plurality of stem-loop reverse transcription primers demonstrates the multi-specificity and quantifies the plurality of target miRNAs simultaneously.

2. The method according to claim 1, wherein step i) of the screening process comprises:

a hybridization reaction wherein each of the plurality of stem-loop reverse transcription primers is hybridized to at least one of the plurality of target miRNA to form a collection of at least one type of miRNA-stem-loop reverse transcription primer complex; and an extension reaction wherein at least one type of cDNA is formed by extending a 3' of the stem-loop reverse transcription primer in the collection of at least one type of miRNA-stem-loop reverse transcription primer complex.

3. The method according to claim 2, wherein the step iii) of the screening process comprises:

adding a combination of forward primers and at least one reverse primer to each of the collections of reverse transcription products from step ii); wherein each of the forward primers has a sequence same to a 5' sequence of one of the plurality of target miRNAs;

adding a combination of probes to each of the collections of reverse transcription products from step ii); wherein each of the probes has a sequence same as a portion of one of the target miRNA, and each of the probes has a fluorescent reporter group different from the fluorescent reporter groups of the other probes, and each of the probes has a quencher group suppressing a fluorescent light produced by the fluorescent reporter group;

separately amplifying each of the collections of reverse transcription products from step ii) with the combination of forward primers, the at least one reverse primer, and the combination of probes to separately form a collection of multiplex qPCR products for each of the collections of reverse transcription products;

detecting a strength of the fluorescent light produced by the fluorescent reporter groups of the combination of probes in each of the collections of multiplex qPCR products; and quantifying each of the plurality of target miRNAs based on the strength of the fluorescent light detected in each of the collections of multiplex qPCR products.

4. The method according to claim 3, wherein the quantification result of each of the plurality of target miRNA comprises a Ct value.

5. The method according to claim 1, wherein the stem-loop sequences of at least two of the plurality of stem-loop reverse transcription primers selected in step a) are the same.

6. A method for screening a multiplex reverse transcription primer combination demonstrating multi-specificity for quantifying a plurality of target miRNAs of a human subject simultaneously, the method comprising:

providing the plurality of target miRNAs, wherein each of the plurality of target miRNAs has a unique 3' sequence; wherein each of the plurality of target miRNAs has a length between about 18-25 nt; and the plurality of target miRNAs includes 2-10 target miRNAs;

providing a plurality of stem-loop reverse transcription primers, wherein each of the plurality of stem-loop reverse transcription primers has a stem-loop sequence forming a stem-loop structure and an anchor sequence complimentary to the unique 3' sequence of one of the plurality of target miRNAs, wherein the plurality of stem-loop reverse transcription primers are selected by a selection process comprising:

a) selecting the stem-loop sequence for each of the plurality of stem-loop reverse transcription primers; and b) selecting a certain length for the anchor sequence of each of the plurality of stem-loop reverse transcription primers, wherein the lengths of the anchor sequences of each of the plurality of stem-loop reverse transcription primers is different from the others;

screening the plurality of stem-loop reverse transcription primers by a screening process for determining the multi-specificity of the plurality of stem-loop reverse transcription primers; wherein the screening process comprises:

separately performing a process of singleplex reverse transcription for each of the plurality of stem-loop reverse transcription primers using a mixed target miRNAs template comprising the plurality of target miRNAs to be quantified;

separately collecting a collection of reverse transcription products from each of the separate singleplex reverse transcription processes;

separately performing a process of multiplex qPCR amplification for each of the collections of reverse transcription products to form a collection of multiplex qPCR products for each of the collections of reverse transcription products;

separately obtaining a quantification result of each of the plurality of target miRNAs based on each of the collections of multiplex qPCR products and obtaining a set of the quantification results of the plurality of target miRNAs; and determining the multi-specificity of the plurality of stem-loop reverse transcription primers based on the set of quantification results, wherein the multi-specificity of the plurality of stem-loop reverse transcription primers is confirmed when the set of quantification results shows that each of the plurality of stem-loop reverse transcription primers specifically reverse transcribes the target miRNA to which the anchor sequence of each of the plurality of stem-loop reverse transcription primer is complimentary.

7. The method according to claim 6, wherein if the multi-specificity of the plurality of stem-loop reverse transcription primers is not confirmed by the collection of quantification results, the plurality of stem-loop reverse transcription primers are modified by a repeat process comprising:

providing a modified plurality of stem-loop reverse transcription primers by repeating the step b) of the selection process to select a new length for the anchor sequence of each of those of the plurality of stem-loop reverse transcription primers which fail to specifically reverse transcribe the target miRNA to which the anchor sequence of each of the stem-loop reverse transcription primer is complimentary; and repeating the screening process to determine the multi-specificity of the modified plurality of stem-loop reverse transcription primers, until the modified plurality of stem-loop reverse transcription primers demonstrates the multi-specificity and quantifies each of the plurality of target miRNAs simultaneously.

8. The method according to claim 6, wherein the step of performing the singleplex reverse transcription process comprises:

a hybridization reaction, wherein each of the plurality of stem-loop reverse transcription primers is hybridized to at least one of the plurality of target miRNAs to form a collection of at least one type of miRNA-stem-loop reverse transcription primer complex; and an extension reaction, wherein at least one type of cDNA is formed by extending a 3' of the stem-loop reverse transcription primer against the at least one of the plurality of target miRNAs in the at least one type of miRNA-stem-loop reverse transcription primer complex.

9. The method according to claim 6, wherein the step of performing the multiplex qPCR amplification process comprises:

adding a combination of forward primers and at least one reverse primer to each of the collections of reverse transcription products; wherein each of the forward primers has a sequence same to a 5' sequence of one of the plurality of target miRNAs;

adding a combination of probes to each of the collections of reverse transcription products; wherein each of the probes has a sequence same as a portion of one of the target miRNA, and each of the probes has a fluorescent reporter group different from the fluorescent reporter groups of the other probes, and each of the probes has a quencher group suppressing a fluorescent light produced by the fluorescent reporter group;

separately amplifying each of the collections of reverse transcription products with the combination of forward primers, the at least one reverse primer, and the combination of probes to separately form a collection of multiplex qPCR products for each of the collections of reverse transcription products;

detecting a strength of the fluorescent light produced by the fluorescent reporter groups of the combination of probes in each of the collections of multiplex qPCR products; and quantifying each of the plurality of target miRNAs based on the strength of the fluorescent light detected in each of the collections of multiplex qPCR products.

10. The method according to claim 7 further comprising a sensitivity test of the plurality of stem-loop reverse transcription primers, wherein the sensitivity test comprises:

1) preparing a plurality templates of mixed target miRNAs having a concentration gradient, wherein each of the plurality templates of mixed target miRNAs has a concentration different from the other templates of mixed target miRNAs;

2) separately performing a process of singleplex reverse transcription on each of the plurality templates of mixed target miRNAs with each of the plurality of stem-loop reverse transcription primers and collecting a collection of reverse transcription products from each of the processes of singleplex reverse transcription;

3) separately performing a process of multiplex qPCR using each of the collections of reverse transcription products from step 2), and obtaining a collection of quantification results of the plurality templates of mixed target miRNAs from the processes of multiplex qPCR;

4) arranging the collection of quantification results by each of the plurality of stem-loop reverse transcription primers; and 5) determining the lowest concentration of the mixed target miRNAs template for each of the plurality of stem-loop reverse transcription primers based on the arranged quantification results.

11. The method according to claim 6, wherein the stem-loop sequence of at least two of the plurality of stem-loop reverse transcription primers are the same.

12. The method according to claim 6, wherein the stem-loop sequence of all the plurality of stem-loop reverse transcription primers are the same.

13. The method according to claim 6, wherein the plurality of target miRNAs comprises a combination of any two or more of hsa-miR-210-3p, hsa-miR-126-3p, hsa-miR-205-5p and hsa-miR-486-5p.

14. The method according to claim 6, wherein the plurality of target miRNAs comprises a combination of any two or more of miR-16-5p, miR-34c-5p, miR-9-3p and miR-9-5p.

15. A method for screening a multiplex stem-loop reverse transcription primer combination demonstrating multi-specificity for quantifying a plurality of target miRNAs of a human subject simultaneously, comprising the steps of:

(A) providing the plurality of target miRNAs wherein each of the plurality of target miRNAs has a unique 3' sequence; wherein each of the plurality of target miRNAs has a length between about 18-25 nt; and the plurality of target miRNAs includes 2-10 target miRNAs;

(B) providing a plurality of stem-loop reverse transcription primers, wherein each of the plurality of stem-loop reverse transcription primers has a stem-loop sequence forming a stem-loop structure and an anchor sequence complimentary to the unique 3' sequence of one of the plurality of target miRNAs, and wherein the lengths of the anchor sequences of at least two of the plurality of stem-loop reverse transcription primers are different from each other;

(C) screening the plurality of stem-loop reverse transcription primers to determine the multi-specificity of the plurality of stem-loop reverse transcription primers, wherein the multi-specificity of the plurality of stem-loop reverse transcription primers is confirmed when each of the plurality of stem-loop reverse transcription primers specifically reverse transcribes the target miRNA to which the anchor sequence of each of the plurality of stem-loop reverse transcription primer is complimentary; and (D) modifying, if the multi-specificity of the plurality of stem-loop reverse transcription primers is not confirmed, the plurality of stem-loop reverse transcription primers by a repeat process until the modified plurality of stem-loop reverse transcription primers demonstrates the multi-specificity and operatively quantifies the plurality of target miRNAs simultaneously.

16. The method according to claim 15, wherein the plurality of stem-loop reverse transcription primers are selected by a selection process comprising:

a) selecting the stem-loop sequence for each of the plurality of stem-loop reverse transcription primers; and b) selecting a certain length for the anchor sequence of each of the plurality of stem-loop reverse transcription primers such that the lengths of the anchor sequences of at least two of the plurality of stem-loop reverse transcription primers are different from each other.

17. The method according to claim 16, wherein the screening step comprises:

i) separately performing a process of singleplex reverse transcription for each of the plurality of stem-loop reverse transcription primers using a mixed target miRNAs template comprising the plurality of target miRNAs to be quantified;

ii) separately collecting a collection of reverse transcription products from each of the separate singleplex reverse transcription processes of step i);

iii) separately performing a process of multiplex qPCR amplification for each of the collections of reverse transcription products from step ii) to form a collection of multiplex qPCR products for each of the collections of reverse transcription products;

iv) separately obtaining a quantification result of each of the plurality of target miRNAs based on each of the collections of multiplex qPCR products and obtaining a collection of the quantification results of the plurality of target miRNAs; and v) determining the multi-specificity of the plurality of stem-loop reverse transcription primers based on the collection of quantification results formed in step iv), wherein the multi-specificity of the plurality of stem-loop reverse transcription primers is confirmed when the collection of quantification results shows that each of the plurality of stem-loop reverse transcription primers specifically reverse transcribes the target miRNA to which the anchor sequence of each of the plurality of stem-loop reverse transcription primer is complimentary.

* * * * *